US008012167B2

(12) United States Patent
Zhu et al.

(10) Patent No.: US 8,012,167 B2
(45) Date of Patent: Sep. 6, 2011

(54) VASCULAR WOUND CLOSURE DEVICE AND METHOD

(75) Inventors: Yong Hua Zhu, Redlands, CA (US); Wolff M. Kirsch, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 1380 days.

(21) Appl. No.: 10/919,939

(22) Filed: Aug. 16, 2004

(65) Prior Publication Data

US 2005/0107826 A1   May 19, 2005

Related U.S. Application Data

(60) Provisional application No. 60/495,424, filed on Aug. 14, 2003, provisional application No. 60/547,154, filed on Feb. 23, 2004.

(51) Int. Cl.
*A61B 17/08* (2006.01)
*A61D 1/00* (2006.01)
*A61F 13/20* (2006.01)
*A61M 5/178* (2006.01)

(52) U.S. Cl. .................. 606/213; 604/11; 604/165.01
(58) Field of Classification Search ............. 606/198, 606/213; 604/11, 15–18, 27, 103, 103.03, 604/117, 164.04, 164.07, 165.01, 165.02, 604/93.01, 164.01, 533; 600/201, 213, 215, 600/239, 566, 567; 128/887
See application file for complete search history.

(56) References Cited

U.S. PATENT DOCUMENTS

| 1,064,307 | A | 6/1913 | Fleming |
|---|---|---|---|
| 3,518,993 | A | 7/1970 | Blake |
| 3,653,388 | A | 4/1972 | Tenckhoff |
| 3,677,244 | A | 7/1972 | Hassinger |
| 3,893,454 | A | 7/1975 | Hagelin |
| 4,166,469 | A | 9/1979 | Littleford |
| 4,306,562 | A | 12/1981 | Osborne |
| 4,394,373 | A | 7/1983 | Malette et al. |
| 4,412,832 | A | 11/1983 | Kling et al. |
| 4,451,256 | A | 5/1984 | Weikl et al. |
| 4,530,698 | A | 7/1985 | Goldstein et al. |
| 4,532,134 | A | 7/1985 | Malette et al. |
| 4,585,437 | A | 4/1986 | Simms |

(Continued)

FOREIGN PATENT DOCUMENTS

CA           2334226           4/2005

(Continued)

OTHER PUBLICATIONS

Angio-Seal, Hemostasis Puncture Closure Device Brochure, Sherwood Medical Co., Jun. 11, 1997.

(Continued)

*Primary Examiner* — Darwin P Erezo
*Assistant Examiner* — Dianne Dornbusch
(74) *Attorney, Agent, or Firm* — Knobbe, Martens, Olson & Bear, LLP

(57) ABSTRACT

A method and apparatus for closing a vascular wound includes an apparatus that can be threaded over a guidewire into place at or adjacent the wound. The apparatus includes a chamber that encloses a hemostatic material therein. When the apparatus is positioned adjacent the wound as desired, the hemostatic material is deployed from the chamber. Blood contacts the hemostatic material, and blood clotting preferably is facilitated by a hemostatic agent within the material. Thus, the vascular puncture wound is sealed by blood clot formation.

38 Claims, 45 Drawing Sheets

U.S. PATENT DOCUMENTS

| | | | |
|---|---|---|---|
| 4,622,970 A | 11/1986 | Wozniak | |
| 4,651,725 A | 3/1987 | Kifune et al. | |
| 4,738,658 A | 4/1988 | Magro et al. | |
| 4,744,363 A | 5/1988 | Hasson | |
| 4,772,266 A | 9/1988 | Groshong | |
| 4,865,593 A | 9/1989 | Ogawa et al. | |
| 4,889,112 A | 12/1989 | Schachner et al. | |
| 4,890,612 A | 1/1990 | Kensey | |
| 4,900,303 A | 2/1990 | Lemelson | |
| 4,921,479 A | 5/1990 | Grayzel | |
| 4,930,674 A | 6/1990 | Barak | |
| 4,961,729 A | 10/1990 | Vaillancourt | |
| 4,984,564 A | 1/1991 | Yuen | |
| 5,002,557 A | 3/1991 | Hasson | |
| 5,015,239 A | 5/1991 | Browne | |
| 5,057,083 A | 10/1991 | Gellman | |
| 5,125,904 A | 6/1992 | Lee | |
| 5,129,882 A | 7/1992 | Weldon | |
| 5,176,128 A | 1/1993 | Andrese | |
| 5,176,129 A | 1/1993 | Smith | |
| 5,183,464 A | 2/1993 | Dubrul et al. | |
| 5,192,301 A | 3/1993 | Kamiya et al. | |
| 5,192,302 A | 3/1993 | Kensey et al. | |
| 5,222,974 A | 6/1993 | Kensey et al. | |
| 5,242,387 A | 9/1993 | Loughlin | |
| 5,250,033 A | 10/1993 | Evans et al. | |
| 5,257,979 A | 11/1993 | Jagpal | |
| 5,259,835 A | 11/1993 | Clark et al. | |
| 5,282,827 A | 2/1994 | Kensey et al. | |
| 5,290,310 A | 3/1994 | Makower et al. | |
| 5,292,332 A | 3/1994 | Lee | |
| 5,300,065 A | 4/1994 | Anderson | |
| 5,306,254 A | 4/1994 | Nash et al. | |
| 5,306,259 A | 4/1994 | Fischell et al. | |
| 5,312,355 A | 5/1994 | Lee | |
| 5,318,542 A | 6/1994 | Hirsch et al. | |
| 5,324,306 A | 6/1994 | Makower et al. | |
| 5,342,393 A | 8/1994 | Stack | |
| 5,350,399 A | 9/1994 | Erlebacher et al. | |
| 5,352,207 A | 10/1994 | Nussbaum | |
| 5,360,397 A | 11/1994 | Pinchuk | |
| 5,370,660 A | 12/1994 | Weinstein et al. | |
| 5,383,896 A | 1/1995 | Gershony et al. | |
| 5,383,899 A | 1/1995 | Hammerslag | |
| 5,391,183 A | 2/1995 | Janzen et al. | |
| 5,397,311 A | 3/1995 | Walker et al. | |
| 5,407,427 A | 4/1995 | Zhu et al. | |
| 5,411,520 A | 5/1995 | Nash et al. | |
| 5,417,699 A | 5/1995 | Klein et al. | |
| 5,419,765 A | 5/1995 | Weldon et al. | |
| 5,431,639 A | 7/1995 | Shaw | |
| 5,437,631 A | 8/1995 | Janzen | |
| 5,443,484 A | 8/1995 | Kirsch et al. | |
| 5,445,597 A | 8/1995 | Clark et al. | |
| 5,480,380 A | 1/1996 | Martin | |
| 5,529,577 A | 6/1996 | Hammerslag | |
| 5,531,759 A | 7/1996 | Kensey et al. | |
| 5,545,178 A | 8/1996 | Kensey et al. | |
| 5,577,993 A | 11/1996 | Zhu et al. | |
| 5,580,344 A | 12/1996 | Hasson | |
| 5,620,461 A | 4/1997 | Muijs Van De Moer et al. | |
| 5,626,601 A * | 5/1997 | Gershony et al. | 606/194 |
| 5,632,727 A | 5/1997 | Tipton et al. | |
| 5,643,318 A | 7/1997 | Tsukernik et al. | |
| 5,645,566 A | 7/1997 | Brenneman et al. | |
| 5,649,911 A | 7/1997 | Trerotola | |
| 5,649,959 A | 7/1997 | Hannam et al. | |
| 5,653,730 A | 8/1997 | Hammerslag | |
| 5,658,298 A | 8/1997 | Vincent et al. | |
| 5,662,681 A | 9/1997 | Nash et al. | |
| 5,665,106 A | 9/1997 | Hammerslag | |
| 5,665,107 A | 9/1997 | Hammerslag | |
| 5,674,231 A | 10/1997 | Green et al. | |
| 5,676,689 A * | 10/1997 | Kensey et al. | 606/213 |
| 5,725,551 A | 3/1998 | Myers et al. | |
| 5,728,114 A | 3/1998 | Evans | |
| 5,728,132 A | 3/1998 | Van Tassel et al. | |
| 5,755,693 A | 5/1998 | Walker et al. | |
| 5,759,194 A | 6/1998 | Hammerslag | |
| 5,810,810 A | 9/1998 | Tay et al. | |
| 5,836,970 A | 11/1998 | Pandit | |
| 5,843,124 A | 12/1998 | Hammerslag | |
| 5,906,631 A | 5/1999 | Imran | |
| 5,910,155 A | 6/1999 | Ratcliff et al. | |
| 5,928,266 A | 7/1999 | Kontos | |
| 5,944,730 A | 8/1999 | Nobles et al. | |
| 5,971,956 A | 10/1999 | Epstein | |
| 6,007,563 A | 12/1999 | Nash et al. | |
| 6,048,358 A | 4/2000 | Barak | |
| 6,056,760 A * | 5/2000 | Koike et al. | 606/148 |
| 6,056,768 A | 5/2000 | Cates et al. | |
| 6,060,461 A | 5/2000 | Drake | |
| 6,159,178 A | 12/2000 | Sharkawy et al. | |
| 6,197,042 B1 | 3/2001 | Ginn et al. | |
| 6,198,016 B1 | 3/2001 | Lucast et al. | |
| 6,277,140 B2 | 8/2001 | Ginn et al. | |
| 6,287,322 B1 * | 9/2001 | Zhu et al. | 606/213 |
| 6,287,323 B1 | 9/2001 | Hammerslag | |
| 6,315,753 B1 * | 11/2001 | Cragg et al. | 604/15 |
| 6,325,789 B1 | 12/2001 | Janzen et al. | |
| 6,346,093 B1 | 2/2002 | Allman et al. | |
| 6,371,974 B1 | 4/2002 | Brenneman | |
| 6,391,048 B1 | 5/2002 | Ginn et al. | |
| 6,425,901 B1 | 7/2002 | Zhu et al. | |
| 6,461,364 B1 | 10/2002 | Ginn et al. | |
| 6,508,828 B1 | 1/2003 | Akerfeldt et al. | |
| 6,524,326 B1 | 2/2003 | Zhu et al. | |
| 6,589,269 B2 | 7/2003 | Zhu et al. | |
| 6,613,070 B2 | 9/2003 | Redmond et al. | |
| 6,632,238 B2 | 10/2003 | Ginn et al. | |
| 6,649,162 B1 | 11/2003 | Biering et al. | |
| 6,890,342 B2 | 5/2005 | Zhu et al. | |
| 6,964,675 B2 | 11/2005 | Zhu et al. | |
| 6,966,896 B2 | 11/2005 | Kurth et al. | |
| 7,201,725 B1 | 4/2007 | Cragg et al. | |
| 7,303,552 B1 | 12/2007 | Chu et al. | |
| 7,331,981 B2 | 2/2008 | Cates et al. | |
| 2001/0004710 A1 | 6/2001 | Felt et al. | |
| 2001/0018598 A1 | 8/2001 | Cruise et al. | |
| 2002/0002386 A1 | 1/2002 | Ginn et al. | |
| 2002/0022822 A1 | 2/2002 | Cragg et al. | |
| 2002/0072767 A1 * | 6/2002 | Zhu | 606/213 |
| 2002/0072768 A1 | 6/2002 | Ginn | |
| 2002/0077656 A1 | 6/2002 | Ginn | |
| 2002/0077657 A1 | 6/2002 | Ginn et al. | |
| 2002/0147479 A1 | 10/2002 | Aldrich | |
| 2003/0023267 A1 | 1/2003 | Ginn | |
| 2003/0044380 A1 | 3/2003 | Zhu et al. | |
| 2003/0045893 A1 | 3/2003 | Ginn | |
| 2003/0050590 A1 | 3/2003 | Kirsch | |
| 2003/0050665 A1 | 3/2003 | Ginn | |
| 2003/0078598 A1 | 4/2003 | Ginn et al. | |
| 2003/0109820 A1 * | 6/2003 | Gross et al. | 604/11 |
| 2003/0158577 A1 | 8/2003 | Ginn et al. | |
| 2003/0158578 A1 | 8/2003 | Pantaged et al. | |
| 2003/0167050 A1 | 9/2003 | Prosl et al. | |
| 2004/0054346 A1 | 3/2004 | Zhu et al. | |
| 2005/0095275 A1 | 5/2005 | Zhu et al. | |
| 2005/0118238 A1 | 6/2005 | Zhu et al. | |
| 2005/0123588 A1 | 6/2005 | Zhu et al. | |
| 2005/0142172 A1 | 6/2005 | Kirsch et al. | |
| 2005/0209637 A1 | 9/2005 | Zhu et al. | |
| 2005/0240137 A1 | 10/2005 | Zhu et al. | |
| 2006/0064124 A1 | 3/2006 | Zhu et al. | |
| 2007/0123816 A1 | 5/2007 | Zhu et al. | |

FOREIGN PATENT DOCUMENTS

| | | |
|---|---|---|
| CA | 2274066 | 2/2006 |
| EP | 0 482 350 A2 | 4/1992 |
| EP | 0 646 350 A1 | 4/1995 |
| EP | 0 493 810 B1 | 11/1995 |
| EP | 0 745 350 A1 | 12/1996 |
| EP | 0 788 769 A1 | 8/1997 |
| EP | 0 818 178 A2 | 1/1998 |
| EP | 0 955 900 | 7/2005 |
| GB | 2318295 A | 4/1998 |
| JP | 11-128360 | 5/1999 |

| | | | |
|---|---|---|---|
| JP | 10-211206 | | 8/1999 |
| JP | 2002-360585 | | 12/2002 |
| WO | WO 93/25148 | | 12/1993 |
| WO | WO 94 21306 | A1 | 9/1994 |
| WO | WO 95/05206 | | 2/1995 |
| WO | WO 96 24291 | A1 | 8/1996 |
| WO | WO 97 20505 | A1 | 6/1997 |
| WO | WO 98 24374 | A1 | 6/1998 |
| WO | WO 99 62405 | A1 | 12/1999 |
| WO | WO 00 02488 | A1 | 1/2000 |
| WO | WO 00 07640 | A2 | 2/2000 |
| WO | WO 00 19912 | A1 | 4/2000 |
| WO | WO 00 33744 | A1 | 6/2000 |
| WO | WO 01 34238 | A1 | 5/2001 |
| WO | WO 01 62159 | A2 | 8/2001 |
| WO | WO 02/05865 | A2 | 1/2002 |
| WO | WO 02 05865 | A2 | 1/2002 |
| WO | WO 02 09591 | A2 | 2/2002 |
| WO | WO 03 008002 | A1 | 1/2003 |
| WO | WO 03 008003 | A1 | 1/2003 |
| WO | WO 03/011154 | * | 2/2003 |
| WO | WO 03/105697 | A1 | 12/2003 |
| WO | WO 03 105697 | A1 | 12/2003 |
| WO | WO 2004/110284 | A1 | 12/2004 |
| WO | WO 2005/016152 | A3 | 2/2005 |
| WO | WO 2007/044510 | | 4/2007 |

OTHER PUBLICATIONS

Gershony, Gary, M.D., A Novel Femoral Access Site Closure Device: Duet, Early European Clinical Trials, Los Angeles Cardiology Associates, Seminar, Coronary Interventions, Oct. 16-18, 1997.

Written Opinion of the International Searching Authority for Application No. PCT/US2004/026609.

Medafor, Inc. Adds Two management Team Members, Press Release, Jun. 7, 2001, http://www.medafor.com/news0601.html.

"Microporous Polysaccharide Hemispheres Provides Effective Topical Hemostasis in a Human Modified Bleeding Time Incision Model" by MEDAFORE, Sep. 2002.

* cited by examiner

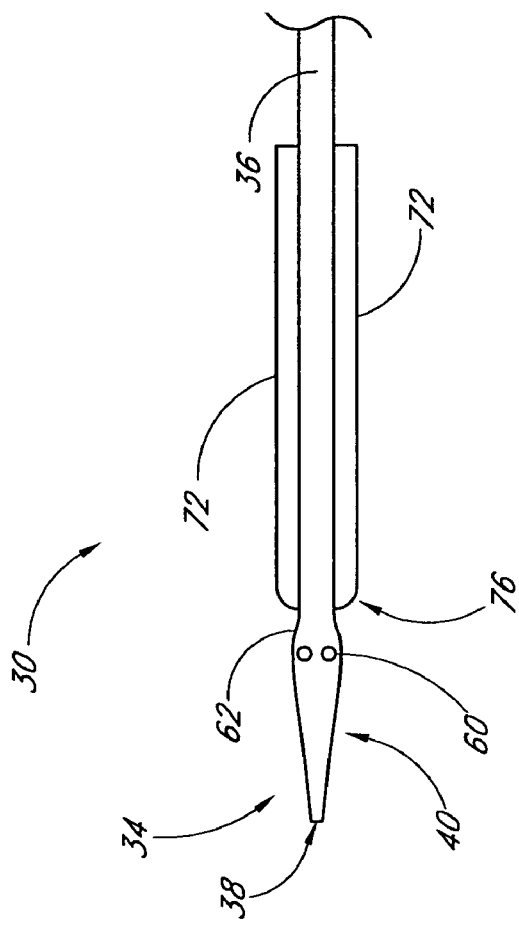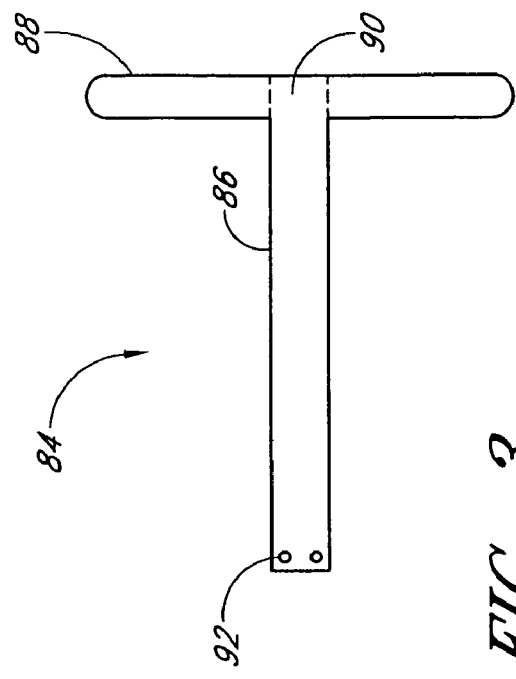

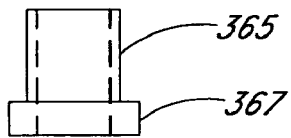
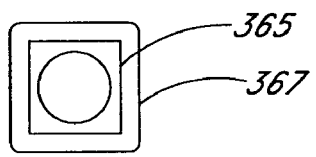
FIG. 32A   FIG. 32B
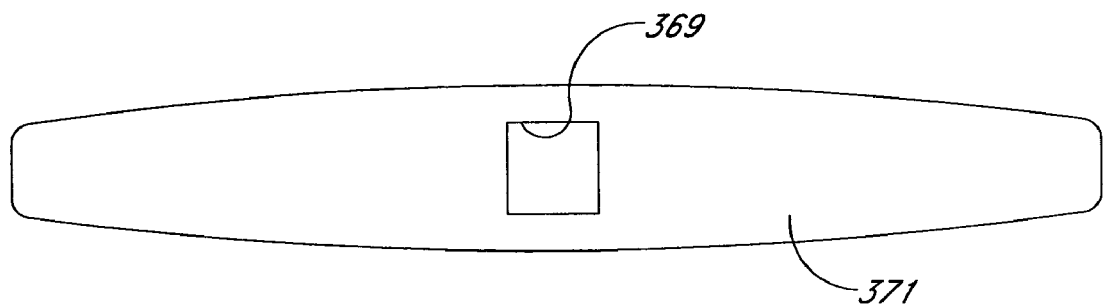
FIG. 33
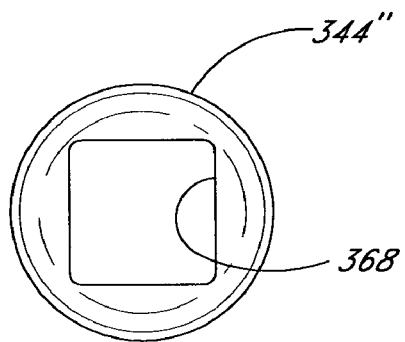
FIG. 34

VASCULAR WOUND CLOSURE DEVICE AND METHOD

RELATED APPLICATIONS

This application claims priority to U.S. Application Ser. No. 60/495,424, which was filed Aug. 14, 2003, and also claims priority to U.S. Application Ser. No. 60/547,154, which was filed on Feb. 23, 2004. The entirety of each of these applications is hereby incorporated by reference.

BACKGROUND OF THE INVENTION

1. Field of the Invention

The present invention generally relates to a system that facilitates closure of openings in blood vessels. More specifically, the present invention delivers a material adjacent a vessel.

2. Description of the Related Art

In many medical procedures, it is necessary to locate an opening in tissue so that some form of treatment, diagnosis or revision, can be applied to that opening. For example, in order to perform transluminal balloon angioplasty, an opening must be created in an artery in order to insert a balloon. This opening must later be closed.

Transluminal balloon angioplasty is used in the treatment of peripheral vascular disease to increase or restore blood flow through a significantly narrowed artery in a limb; it is also used in the treatment of blockage of the coronary arteries. In fact, coronary angioplasty has emerged as a major viable alternative to bypass surgery for revascularization of stenotic and occluded coronary arteries. Unlike bypass surgery, angioplasty does not require general anesthesia, opening of the chest wall, use of a heart-lung machine, or transfusion of blood. Angioplasty is not only less invasive and less traumatic to the patient, but is also less expensive because of the shorter hospital stay and shorter recovery time.

Transluminal balloon angioplasty is performed by first inserting a hollow needle through the skin and surrounding tissues and into the patient's femoral artery. A guidewire is advanced through the hollow needle and into the artery, then along the patient's vasculature toward the site of the blocked blood vessel or valve to be treated. X-ray imaging is used to help guide the guidewire through the vascular system and into position adjacent the stenosis to be treated. A balloon catheter is then threaded over the guidewire and advanced until the deflated balloon is within the stenosis. The balloon is then repeatedly inflated to widen the narrowed blood vessel. After the procedure is complete, the catheter and guidewire are withdrawn from the blood vessels and the patient.

After the catheter used during angioplasty is removed, the puncture wound in the femoral artery must be closed and the bleeding through the puncture site in the artery stopped. Often, ice packs and/or pressure are applied to the area surrounding the wound for a period lasting up to several hours in an attempt to stop the bleeding. There exists, however, a significant chance that the wound will reopen and begin bleeding again when the patient moves. Another possible complication is the development of a false aneurysm, which increases the risks of both infection and reopening.

Efforts have been made to close the puncture wound using staples, clips, collagen plugs, and sutures. These efforts, and the devices incident thereto, tend to be cumbersome and achieve only limited success.

Other wounds in the vasculature of a patient can also be difficult to locate, access and close. Thus, a device and method to facilitate locating and closing such wounds in the vasculature of a patient would be beneficial. A device having the ability to consistently and reliably locate, isolate and close the puncture wound would eliminate the prolonged bleeding currently associated with such wounds.

SUMMARY OF THE INVENTION

Accordingly, there is a need in the art for a device and method for precisely locating a blood vessel wound and sealing the wound.

In accordance with one embodiment, an apparatus is provided for subcutaneously delivering a material. The apparatus comprises an elongate delivery tube having a chamber configured to accommodate a material therewithin, an elongate pusher member having a distal portion configured to slidably extend through at least a portion of the delivery tube so as to push at least a portion of the material out of the delivery tube, and a flexible locking member configured to fit at least partially around the pusher member and adapted to expand in a transverse direction when subjected to generally longitudinal compression. The flexible locking member is disposed adjacent the pusher member so that when the locking member is subjected to generally longitudinal compression, the locking member expands transversely to engage the pusher member to increase friction between the pusher member and the locking member.

In accordance with another embodiment, the pusher member has at least one protuberance. The flexible locking member is disposed adjacent the protuberance so that when the locking member is subjected to longitudinal compression, the locking member expands transversely to engage the pusher member protuberance so that the pusher member is restrained from moving relative to the locking member.

In accordance with yet another embodiment, the present invention describes an assembly for closing a vascular wound. The assembly includes a delivery tube configured to accommodate a hemostatic material therewithin, an apparatus configured to position a distal end of the delivery tube adjacent the vascular wound, a pusher member having a distal portion configured to fit at least partially through the proximal end of the delivery tube, and an adjustable stopper disposed about a surface of the pusher member. A portion of the pusher member has a diameter larger than the diameter of at least a portion of the delivery tube. The adjustable stopper is configured to engage the surface of the pusher member and to selectively move proximally or distally along the surface of the pusher member to adjustably couple the apparatus and the delivery tube.

In accordance with yet another embodiment a surgical method is provided comprising accessing a subcutaneous blood vessel by forming a puncture through a wall of the blood vessel, advancing at least one surgical implement through the blood vessel puncture, and closing the puncture. A major surgical implement of the at least one surgical implement has a diameter advanced through the puncture that is greater than or equal to a diameter advanced through the puncture of any other of the at least one surgical implement. Closing the puncture comprises providing a vessel wound closure device comprising a catheter, a hemostatic material disposed on the catheter, and a pusher member configured to push the hemostatic material distally over the catheter. The catheter has a diameter greater than the diameter advanced through the puncture of the major surgical implement. As such, the catheter engages wound edges of the puncture in a manner to substantially plug the puncture and prevent hemostatic material from passing between the catheter and the wound edge and into the blood vessel.

For purposes of summarizing the preferred embodiments and the advantages achieved over the prior art, certain embodiments and advantages have been described herein above. Of course, it is to be understood that not necessarily all such advantages may be achieved in accordance with any particular embodiment. Thus, for example, those skilled in the art will recognize that the invention may be embodied or carried out in a manner that achieves or optimizes one advantage or group of advantages as taught herein without necessarily achieving other objects or advantages as may be taught or suggested herein.

The embodiments discussed above and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 2 is a side view of a distal portion of the apparatus of FIG. 1.

FIG. 3 is a side view of a push member having features in accordance with the present invention.

FIG. 32a shows a side view of a handle support for use in connection with the pusher member of FIG. 31.

FIG. 32b shows a top view of the handle support of FIG. 32a.

FIG. 33 shows a top view of the handle for use in connection with the pusher member of FIG. 31.

FIG. 34 shows a top view of the coupling member for use in connection with the pusher member of FIG. 31.

DETAILED DESCRIPTION OF PREFERRED EMBODIMENTS

The present embodiments are especially useful for closing vascular puncture wounds that are difficult to access and/or visualize. It is difficult to directly and accurately modify a wound in a blood vessel in order to close such wounds. Additionally, there are pitfalls associated with directly modifying the blood vessel. For example, since the clinician cannot see the wound, it is difficult to correctly place closure media such as sutures, staples, or clips. Incorrect placement of such closure media likely results in inadequate closure; the puncture wound remains open, perhaps without the clinician being aware. Additionally, incorrect placement of closure media may cause permanent damage to the vessel, including tearing and additional puncture wounds. Further, if closure media extends through the wound and into the blood flow, this media can increase the likelihood of thrombus formation or could introduce potentially toxic substances into the bloodstream. Of course, closure media inadvertently released into the bloodstream could lead to serious blood vessel blockage complications.

Figure 1:
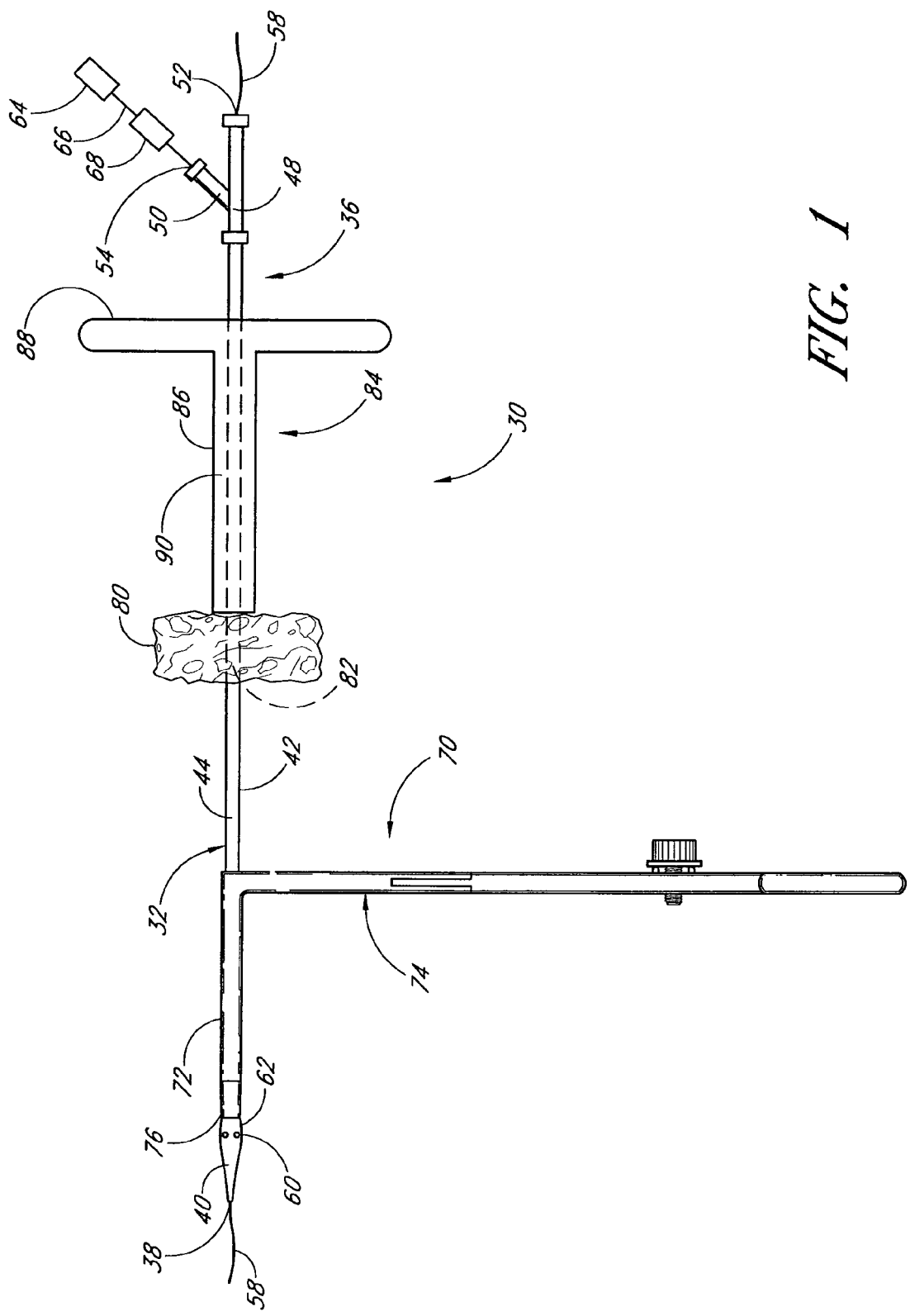
FIG. 1 is a side view of an embodiment of a vascular closure apparatus shown assembled and ready for use.

With reference to FIG. 1, a vascular wound closure assembly 30 includes an elongate catheter 32 having a distal end 34 and a proximal end 36 of the catheter 32. A distal opening 38 is formed through the distal end 34 of the catheter 32 and opens along a longitudinal axis of the catheter 32. The catheter 32 includes a tapered tip 40 at the distal end 34. An elongate main body 42 of the catheter 32 is disposed proximal the tapered tip 40. Preferably the main body 42 has a substantially uniform diameter along its length. A lumen 44 extends longitudinally within the catheter 32 from the distal opening 38 to the proximal end 36.

A connector portion 46 is provided on the proximal end 36. The connector portion 46 includes a main lumen 48 and a secondary lumen 50. The main lumen 48 extends along the longitudinal axis of the catheter 32 and is coextensive with the catheter lumen 44. The secondary lumen 50 extends outwardly from the main lumen 48, but communicates with the main lumen 48 and the catheter lumen 44. A proximal opening 52 is provided at the proximal end of the main lumen 48 and, like the distal opening 38, opens along the longitudinal axis. A secondary opening 54 opens into the secondary lumen 50.

The distal and proximal openings 38, 52 are sized and adapted to accommodate a guidewire 58 such as the guidewire used in angioplasty and other vascular surgeries. As such, the guidewire 58 can be threaded through the catheter 32 and the catheter can be advanced over the guidewire 58.

Holes 60 are formed through a side wall of the catheter 32 near the distal end 34 of the catheter 32. Preferably, at least two holes 60 are provided. All of the holes 60 preferably are disposed substantially the same distance from the distal end 34 of the catheter 32. Preferably, a raised portion 62 of the catheter 32 is provided in the region around the holes 60, which region is proximal of the tip 40 and distal of the main body 42. At the raised portion 62, the catheter 32 has an outer diameter that is slightly larger than the outer diameter throughout the catheter main body 42.

With continued reference to FIG. 1, a vacuum or other source of suction 64 is provided and communicates, through tubing 66, with the secondary lumen 50 of the catheter connector portion 46. Thus, a vacuum is drawn through the catheter lumen 44. Preferably, the distal and proximal openings 38, 52, which accommodate the guidewire 58, are sized so that the guidewire 58 substantially plugs the openings; thus, the vacuum is drawn through the holes 60. A viewing port 68 is arranged between the source of suction 64 and the catheter 32. The viewing port 68 is configured to allow a clinician to view the material that is drawn by suction through the holes 60 and through the catheter lumen 44. The viewing port 68 will be discussed in more detail below.

With reference to FIGS. 1 and 2, a retractor 70 preferably is mounted on the catheter 32. The retractor 70 includes opposing elongate retractor arms 72 that are aligned longitudinally on the catheter 32. A retractor body 74 is configured to selectively open and close the retractor arms 72 when operated by a clinician. The elongate retractor arms 72 of the retractor 70 are positioned on the catheter 32 so that distal ends 76 of the arms are positioned proximal of the catheter holes 60 a distance that is at least the same as the width of an artery wall, preferably at least about 0.5 to 2 millimeters.

It is to be understood that the present device can include structure that is somewhat different than the particular structure shown in FIGS. 1 and 2. For example, other catheter and retractor structures can appropriately be used. For example, some acceptable catheter and retractor embodiments are presented in U.S. application Ser. No. 09/325,982, filed on Jun. 4, 1999, now U.S. Pat. No. 6,287,322, which is hereby incorporated by reference in it entirety.

With reference again to FIG. 1, a hemostatic member 80 is arranged on the catheter 32 proximal of the retractor 70. As will be discussed in more detail below, the hemostatic member comprises a material that is made of or includes a hemostatic agent. The hemostatic agent is adapted to aid blood clotting. In one embodiment, the hemostatic member 80 comprises a sponge or sponge-like material. In this description, the term sponge is intended to be a broad term that is used in accordance with its ordinary meaning and refers to, without limitation, a material that is at least partially porous and is adapted to allow at least some blood to flow into and within the material so as to soak the material with blood. For example, a sponge may include a natural or artificial sponge, a woven or non-woven cloth, a fibrous puff or the like. Additionally, a sponge may comprise a material that soaks up at least a portion of blood that may come in contact with the material, or may comprise a material that doesn't soak up blood.

For purposes of this description, the hemostatic member 80 is referred to as the sponge 80. However, it is to be understood that use of the term "sponge" does not limit the scope of materials that can be used as the hemostatic member. In fact, any material that aids or facilitates blood clotting can be used as the hemostatic member.

Throughout this description, the term hemostatic agent is used as a broad term in its ordinary sense and refers to, without limitation, an agent that promotes blood clotting. Such an agent may take many forms, including liquid, powder, beads, etc. and can include or be combined with a substrate or carrier. The term hemostatic material is also used in this description as a broad term used in its ordinary sense. It refers to, without limitation, any material having properties that promote blood clotting. Thus, hemostatic material can include a hemostatic agent taken alone or in combination with a substrate or carrier that is formed separately from the agent. The term hemostatic material includes hemostatic sponges.

Preferably, the sponge 80 extends circumferentially around the catheter main body 42, and is arranged so that it can be slid longitudinally along the catheter 32. Most preferably, the catheter 32 extends through a passageway 82 through the sponge 80. The passageway 82 is formed as the catheter 32 is forced through the sponge 80.

A push member 84 is also arranged on the catheter 32 proximal of the sponge 80. With reference also to FIG. 3, the push member 84 comprises a body portion 86 and a proximal handle portion 88. An elongate lumen 90 is formed through the body portion 86. As shown in FIG. 1, the lumen 90 preferably encircles the catheter 32 so as to allow the push member 84 to slide relative to the catheter 32. A plurality of holes 92 are formed through the body portion 86 at a point near the distal end of the push member 84.

As will be discussed in more detail below in connection with FIG. 4, the vascular wound closure assembly 30 enables a clinician to precisely locate a subcutaneous vascular wound "w", access the wound w, and deliver the hemostatic sponge 80 to the wound site. The hemostatic sponge 80 includes a hemostatic agent that helps facilitate closure of the wound w.

In order to properly apply the hemostatic sponge 80, the vascular closure assembly 30 first precisely locates and provides access to the vascular wound w. It is to be understood that the present method and apparatus can be used to close various vascular and other wounds. FIGS. 1-11, and the accompanying discussion, present an example using an embodiment to close a puncture wound w in a patient's femoral artery 94.

With specific reference to FIGS. 1, 2, 4 and 5, in order to precisely locate and provide access to a femoral artery puncture wound w, the catheter 32 is first threaded over a guidewire 58 that has been previously inserted into the patient's femoral artery 94 through the puncture wound w. The lumen 44 is attached to the source of suction 64 and the assembly 30 is advanced over the guidewire 58 through a patient's tissue 96 so that the distal tip 40 of the catheter 32 extends through the vascular puncture wound w.

As the assembly 30 is advanced, the source of suction 64 draws bodily fluids through the holes 60. The fluids pass through the viewing port 68, which allows the clinician to identify the fluids being withdrawn. The viewing port 68 can have any suitable structure or location. For example, the viewing port can comprise clear tubing attached to the catheter, a substantially transparent syringe that functions as both a source of suction and a viewing port, or a portion of the catheter that is substantially transparent. Most preferably, the catheter 32 is formed of a transparent material so that the clinician becomes aware as soon as blood begins to be drawn through the catheter.

Figure 4:
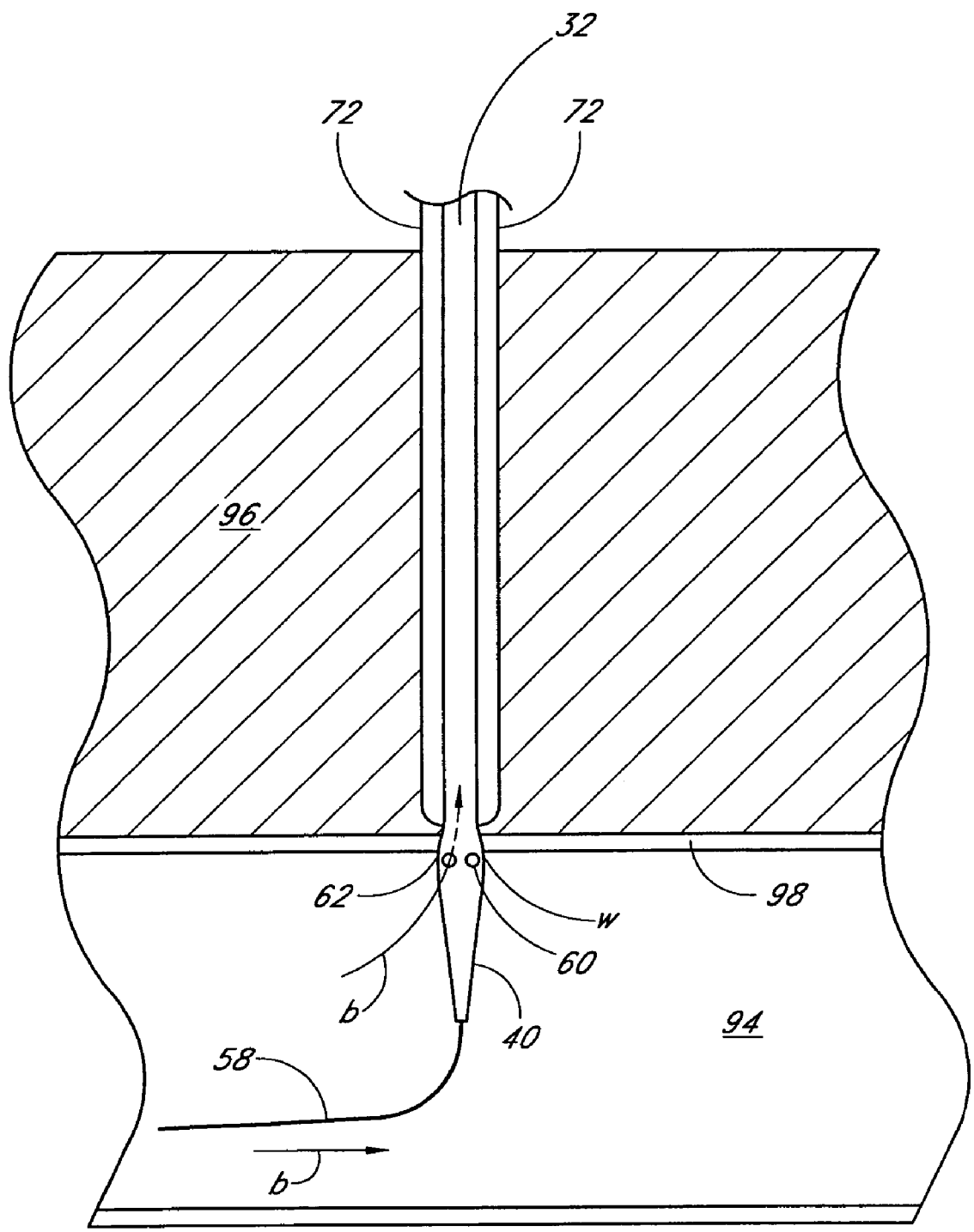
FIG. 4 shows the apparatus of FIG. 1 advanced over a guidewire into a blood vessel of a patient.
Figure 5:
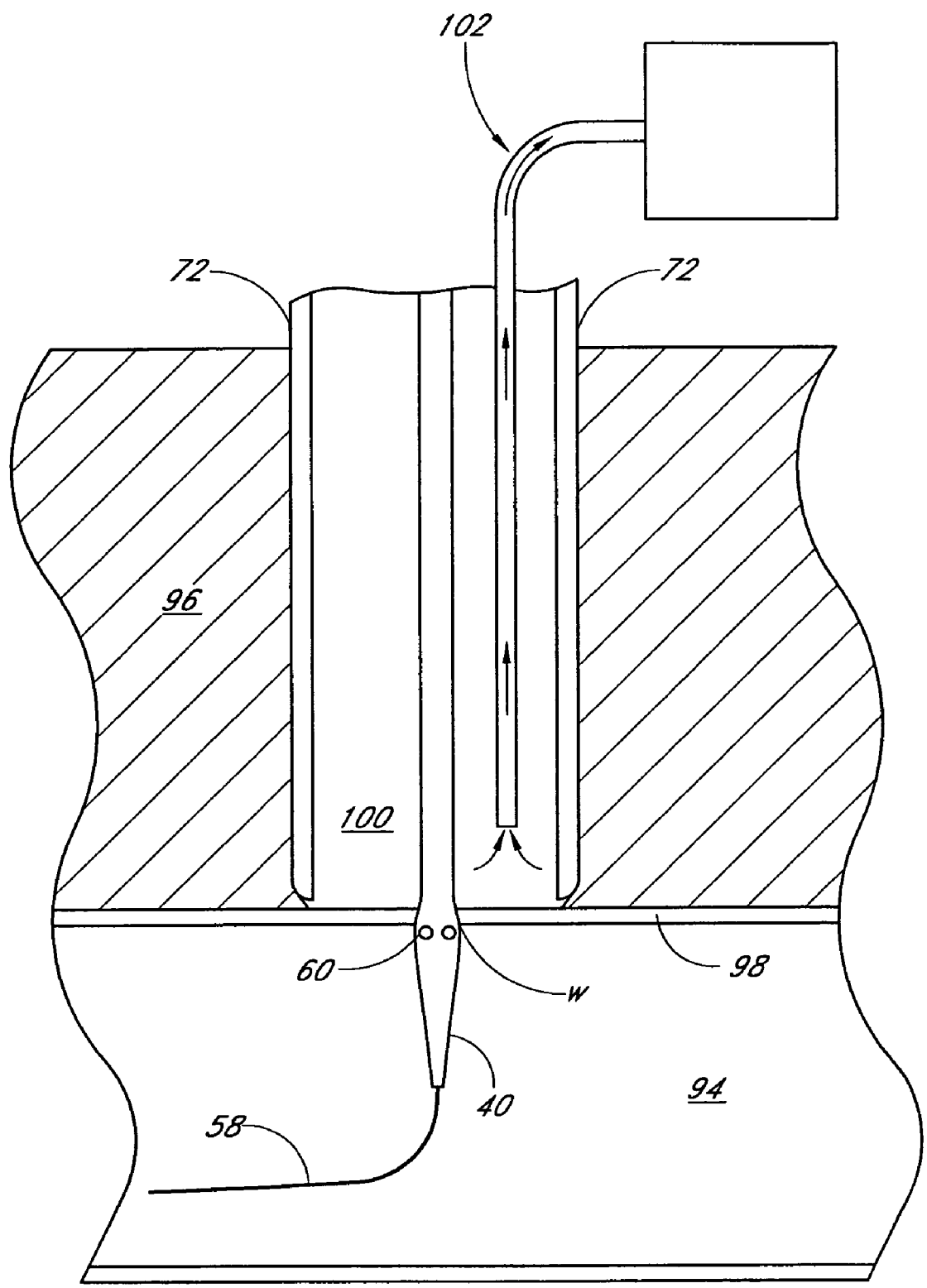
FIG. 5 shows the arrangement of FIG. 4 with the retractor arms open and a suction tool in use.

When the holes 60 pass the artery wall 98 and enter the blood vessel 94, as shown in FIG. 4, blood "b" begins to be drawn through the holes 60 into the catheter 32 and is conducted past the viewing port 68. Thus, when blood b is observed in the viewing port 68, the clinician will know that the holes 60 have just passed into the puncture wound w and that the distal ends 76 of the retractor arms 72 are thus positioned adjacent the outer wall 98 of the artery 94, preferably within about 2 mm of the artery wall 98. The retractor arms 72 are then separated as shown in FIG. 5, thus drawing surrounding tissue 96 away from the wound w and creating a field 100 around the puncture wound w. The catheter 32 remains disposed partially within the puncture wound w, effectively plugging the wound and preventing blood from flowing through the wound. The raised portion 62 flexes the edges of the wound w to enhance the seal between the catheter 32 and the puncture wound edges.

With continued reference to FIG. 5, a suction tool 102 can be used to clear away bodily fluids and other matter that may be within the field 100 and to clean the wall 98 of the blood vessel 94 adjacent the puncture wound w.

Figure 6:
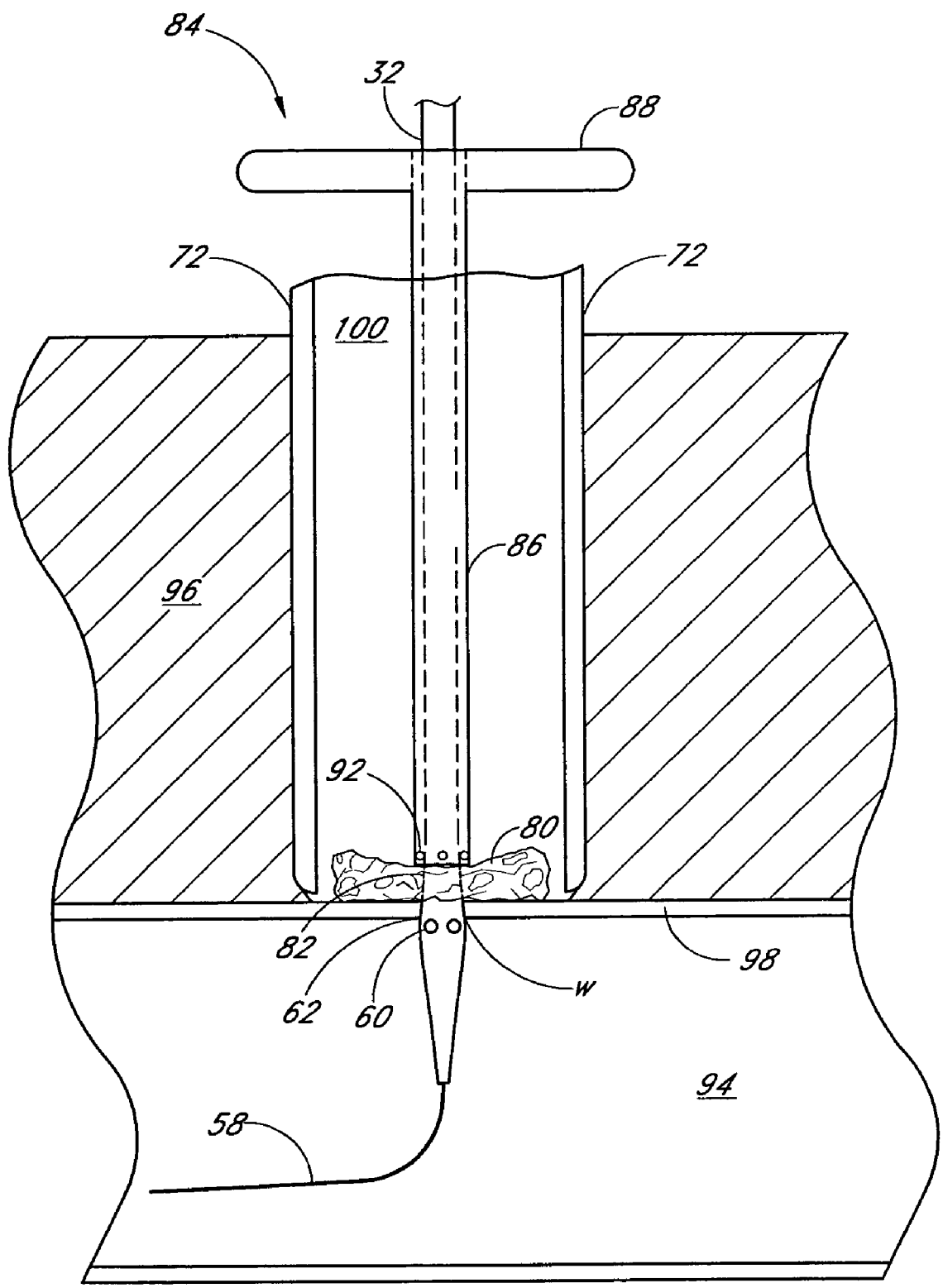
FIG. 6 shows the arrangement of FIG. 5, wherein a hemostatic sponge has been advanced into contact with the blood vessel wall.

With reference next to FIG. 6, once the puncture wound w has been precisely located, the push member 84 is advanced distally along the catheter 32, thus advancing the sponge 80 into contact with the vessel wall 98 so as to surround the puncture wound w. As mentioned above and discussed in more detail below, the sponge 80 comprises a hemostatic agent that will help accelerate blood clot formation at the wound site w in order to help the wound heal faster.

Preferably, the sponge 80 is at least partially coated with an adhesive so that the sponge will at least partially bond to the vessel wall 98. Alternatively, or in addition, flowable adhesive can be delivered into the field around the puncture wound before the sponge is advanced into contact with the vessel wall. Of course, the sponge can be delivered without using any adhesive.

Figure 7:
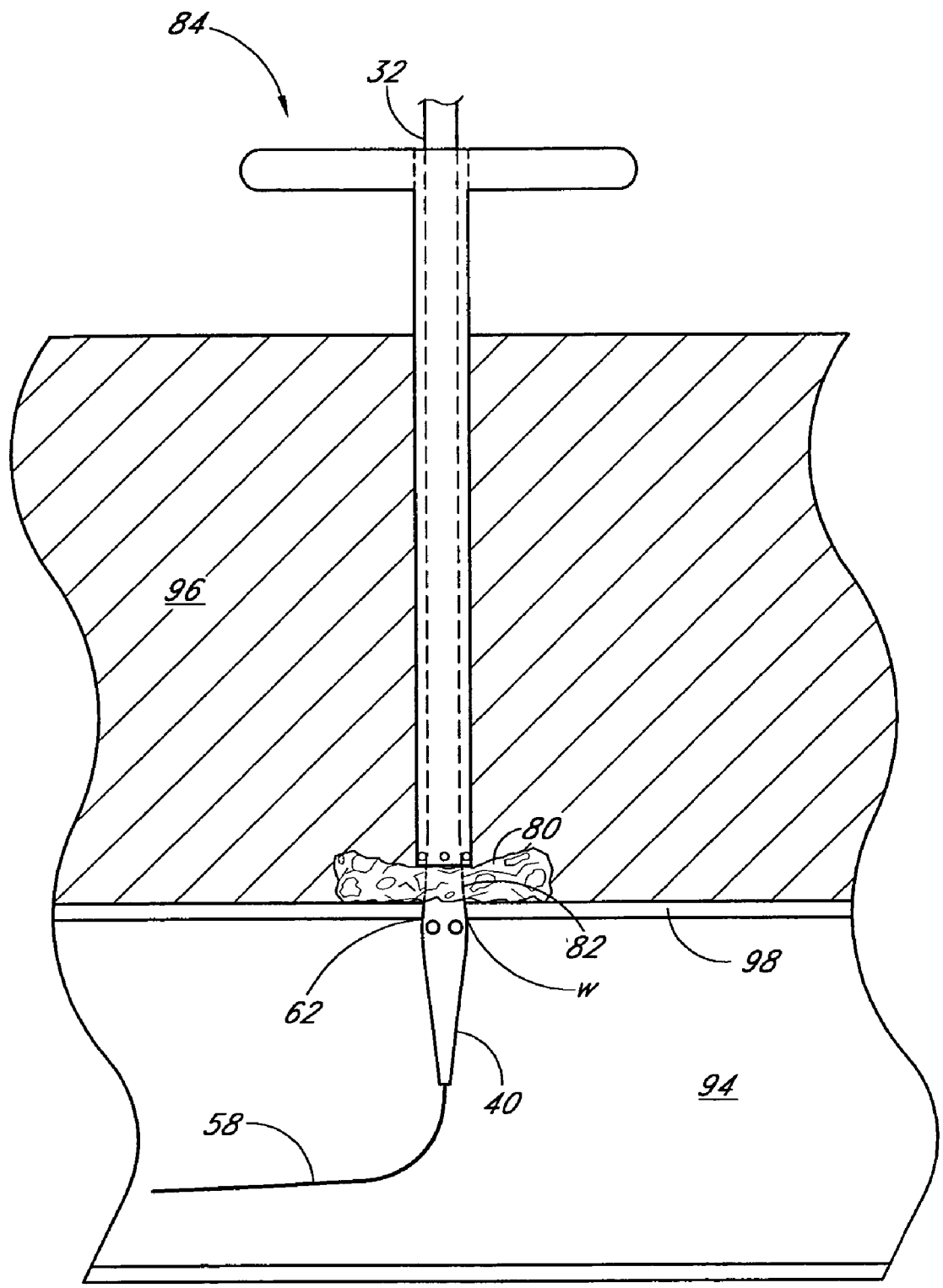
FIG. 7 shows the arrangement of FIG. 6, with the retractor arms removed.

The sponge 80 preferably is mounted onto the catheter 32 so as to substantially encircle the catheter 32. Thus, since the tip 40 of the catheter is disposed in the wound, the sponge 80 substantially surrounds the wound w when the sponge is positioned adjacent the vessel wall 98. When the sponge 80 is in place adjacent the wound w, the retractor 70 can be removed, as shown in FIG. 7. When the retractor 70 is removed, the surrounding body tissues 96 collapse around the sponge 80 and push member 84. The push member 84 holds the sponge 80 in position while body tissue 96 surrounds the sponge 80 and while the adhesive cures.

Figure 8:
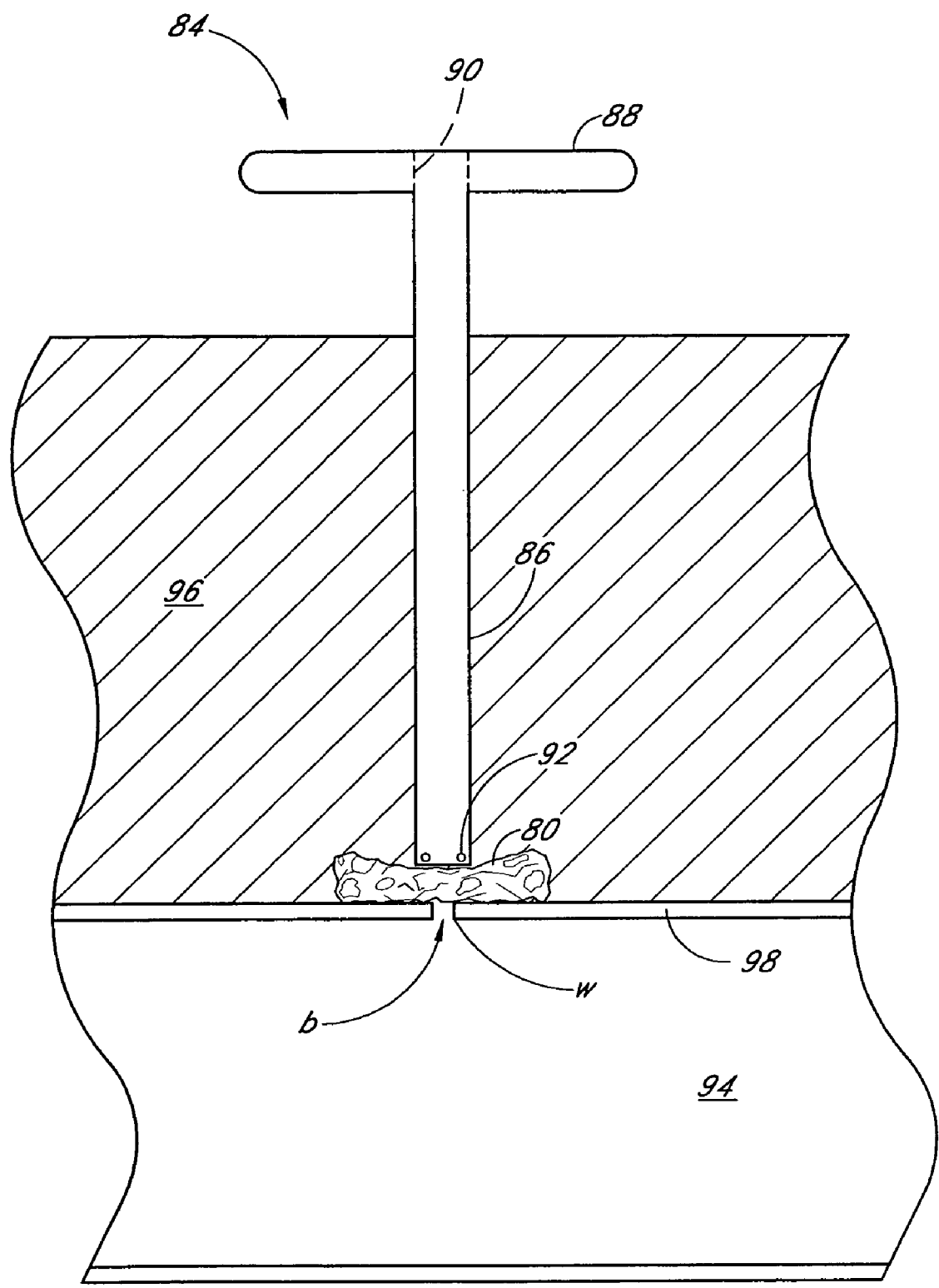
FIG. 8 shows the arrangement of FIG. 7 with the catheter and guidewire removed.

With reference next to FIG. 8, with the push member 84 in place, the catheter 32 and guidewire 58 can also be removed from the patient. The passage 82 through the sponge 80, which had been occupied by the catheter 32, collapses onto itself so that it is substantially closed. The vessel wound w is no longer plugged by the catheter 32, and it is anticipated that blood b from the vessel 94 will flow into the sponge 80, at least partially soaking the sponge 80. Although the retractor 70 is removed prior to the catheter 32 in the above-discussed embodiment, it is to be understood that, in another embodiment, the catheter may be removed prior to the retractor.

In still another embodiment, additional pressure can be applied to the push member 84 in order to at least partially block blood flow through the blood vessel 94. In this manner, the clinician can control how quickly blood will flow through the wound w and into the sponge 80. Of course, other methods and apparatus can be used to temporarily reduce or stop blood flow through the vessel.

In a preferred embodiment, the sponge 80 comprises a material made of, soaked in or otherwise treated with a hemostatic agent. The agent is specially adapted to aid blood clotting. Thus, blood that flows into the sponge encounters the agent and will quickly become clotted, causing natural sealing of the wound through blood clotting. Sponge-like hemostasis agents are available and can include products such as Gelfoam™, Oxycell™ and Avitene™. Another material that can be used as a sponge is chitosan. These and other appropriate sponges may be impregnated with agents such as thrombin, a liquid clotting agent, to help accelerate blood clot formation and Hemadex™, which is available from Medafor, Inc. Another material that may advantageously be used is a collagen Ultrafoam™ sponge marketed by C.R. Bard/Davol, Inc. The Ultrafoam™ sponge is made from Avitene™ collagen, a natural clotting agent, and does not require the addition of thrombin. This reduces preparation time and the risk that a patient will experience a potentially hazardous reaction to bovine thrombin. Other medicaments can also be included in the sponge. For example, antibiotic medicines, anti-inflammatory drugs, healing aids, and the like can be impregnated into the sponge material.

In a particularly preferred embodiment, the hemostatic agent comprises a starch such as bioabsorbable microporous polysaccharide microspheres (e.g., TRAUMADEX™ marketed by Emergency Medical Products, Inc. of Waukesha, Wis.). The microspheres have micro-replicated porous channels. The pore size of the microspheres facilitates water absorption and hyperconcentration of albumin, coagulation factors, and other protein and cellular components of the blood. The microspheres also affect platelet function and enhance fibrin formulation. In addition, the microspheres are believed to accelerate the coagulation enzymatic reaction rate. When applied directly, with pressure, to an actively bleeding wound, the particles act as molecular sieves to extract fluids from the blood. The controlled porosity of the particle excludes platelets, red blood cells, and serum proteins larger than 25,000 Daltons, which are then concentrated on the surface of the particles. This molecular exclusion property creates a high concentration of platelets, thrombin, fibrinogen, and other proteins on the particle surface, producing a gelling action. The gelled, compacted cells and constituents accelerate the normal clotting cascade. The fibrin network formed within this dense protein-cell matrix adheres tightly to the surrounding tissue. The gelling process initiates within seconds, and the resulting clot, while exceptionally tenacious, breaks down normally along with the microparticles. Such microporous polysaccharide microspheres, and additional hemostatic agents, are discussed in more detail in Applicants' copending application entitled "Deployable Multifunctional Hemostatic Agent," U.S. application Ser. No. 10/868,201, filed Jun. 14, 2004, the entirety of which is hereby incorporated by reference.

Any suitable hemostatic substrate can be employed as a support for the hemostatic agents of preferred embodiments. However, in a particularly preferred embodiment the hemostatic substrate comprises chitosan. Chitosan is obtained from chitin, a biopolymer obtained principally from shrimp and crab shell waste. Chitosan is the main derivative of chitin, and is the collective term applied to deacetylated chitins in various stages of deacetylation and depolymerization. The chemical structure of chitin and chitosan is similar to that of cellulose. The difference is that instead of the hydroxyl group that is bonded at C-2 in each D-glucose unit of cellulose, there is an acetylated amino group ($—NHCOCH_3$) at C-2 in each D-glucose unit in chitin and an amino group at C-2 in each D-glucose unit of chitosan.

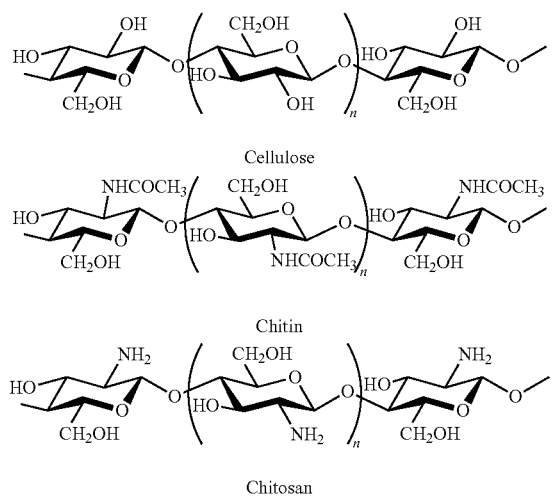

Cellulose

Chitin

Chitosan

Chitin and chitosan are both nontoxic, but chitosan is used more widely in medical and pharmaceutical applications than chitin. Chitosan exhibits good biocompatibility and is biodegradable by chitosanase, papain, cellulase, and acid protease. Chitosan exhibits anti-inflammatory and analgesic effects, and promotes hemostasis and wound healing. Chitosan has also been used as a hemostatic agent in surgical treatment and wound protection. The hemostatic effect of chitosan has been described in U.S. Pat. No. 4,394,373.

A single hemostatic substrate or combination of hemostatic substrates of different forms and/or compositions can be employed in the devices of preferred embodiments. Different substrate forms can be preferred, for example, fibrous puff, fleece, fabric, sheet, suture, or powder. A homogeneous mixture of different substrate-forming materials can be employed, or composite substrates can be prepared from two or more different formed substrates. A preferred composite comprises chitosan and collagen. Additional details concerning chitosan and other suitable substrates are discussed in more detail in Applicants' copending application "Deployable Multifunctional Hemostatic Agent."

The sponge-like substrate material preferably is soft and pliable and will conform to the structure of the blood vessel, the wound and the field around the blood vessel. Thus, the sponge-like material is specially suited for use in the confined space surrounding a vascular puncture. Additionally, the hemostatic sponge 80 will be held in place by the tissue 96 surrounding the puncture wound w, which tissue 96 collapses over the sponge 80 when tools such as the retractor 70 are removed.

Figure 9:
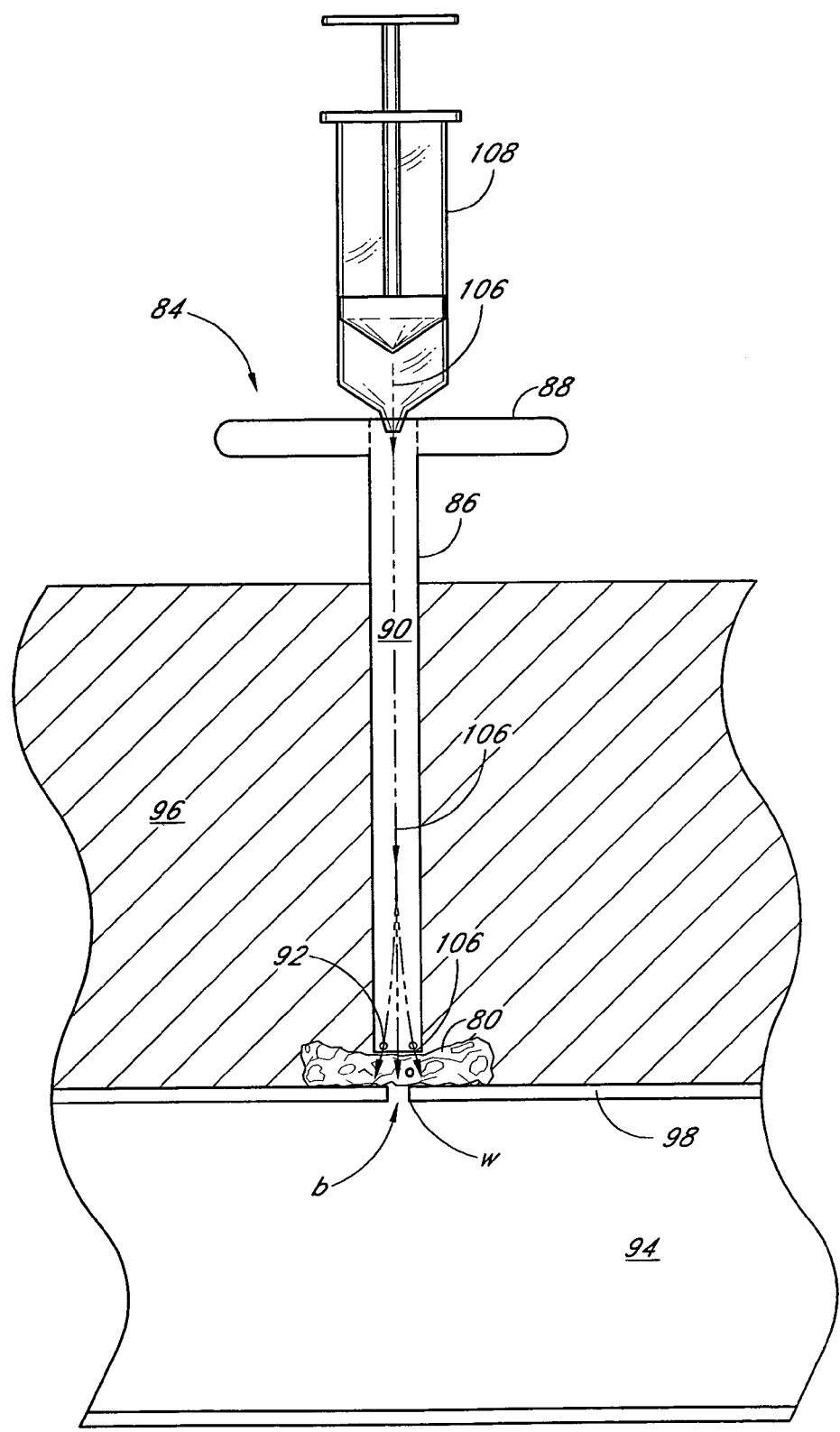
FIG. 9 shows the arrangement of FIG. 8, wherein a flowable adhesive is being delivered to the sponge.

To further help hold the sponge 80 in place, flowable adhesive 106 from a source of adhesive 108 can be delivered through the lumen 90 of the push member 84 and onto the sponge 80, as shown in FIG. 9. The adhesive 106 flows through the open distal end of the push member 84 and also through the holes 92 through the push member body portion 86. Upon curing, the adhesive 106 can form a sealing layer around and within the sponge 80, thus confining the blood b to the sponge area. This helps minimize bleeding and even further speeds clot formation. In one embodiment, adhesive, when cured, is substantially non-porous, and thus confines blood to a desired area. Adding adhesive 106 will also facilitate more complete closure of the passage through the sponge, which passage was vacated by the catheter 32. Further, the adhesive 106 will help hold the sponge 80 in place relative to the puncture wound w and the surrounding tissue 96.

As discussed above, prior to being advanced into contact with the blood vessel wall, the sponge 80 may be soaked in an adhesive or, more preferably, coated with a layer of adhesive. In this manner, adhesive distribution on the sponge can be controlled. By controllably applying a coating of adhesive around the outer surface of the sponge, the adhesive will bond the sponge to the area surrounding the blood vessel wound w, including the vessel 94 itself, and also can form a perimeter seal of the sponge when the adhesive cures. The coating of adhesive can act as a non-porous or selectively-porous membrane confining the blood b to the sponge 80. It is to be understood that a coating of adhesive may be used instead of or in addition to applying additional adhesive 106 through the push member 84.

Various kinds of flowable adhesives may be acceptable for use with the sponge. For example, fibrin tissue sealants such as Tisseel®, which is available from Baxter Healthcare Corp., may be appropriate. Other commercially available adhesives that may be appropriate include Bioglue™, available from Cryolife, Inc., and Floseal™, which is available from Fusion Medical Technologies. Various cyanoacrylate adhesives are currently commercially available and can be used with this invention. Of course, any product that is capable of sealing the sponge or at least retarding blood flow through or beyond the sponge would be acceptable. It is also to be understood that certain adhesives will not require that the field and/or the outer wall of the blood vessel be cleared before the adhesive is injected.

Curing time and ease of use will vary depending on the adhesive used. For example, some adhesives cure to a malleable gel-like state within a few seconds, while others will cure directly to a hardened state in a few minutes. The time period for curing is chosen to allow the clinician to advance the sponge into position adjacent the wound and in contact with the artery, at which time the sponge will begin to be bonded to the vessel wall and substantially sealed by the adhesive. It should be appreciated that any acceptable adhesive having any acceptable curing time may be used. In accordance with this description, an adhesive is considered to be cured when it is adhered to surrounding tissue, and when it does not spontaneously flow.

The push member 84 may be kept in place for any reasonable time period in order to allow the adhesive 106 to cure. Also, multiple sponges can be used, if desired. Preferably, however, the adhesive 106 will cure sufficiently in about five minutes or less. Other tools, such as an ultraviolet light source or a heat application device, may be used to help speed adhesive curing.

Figure 10:
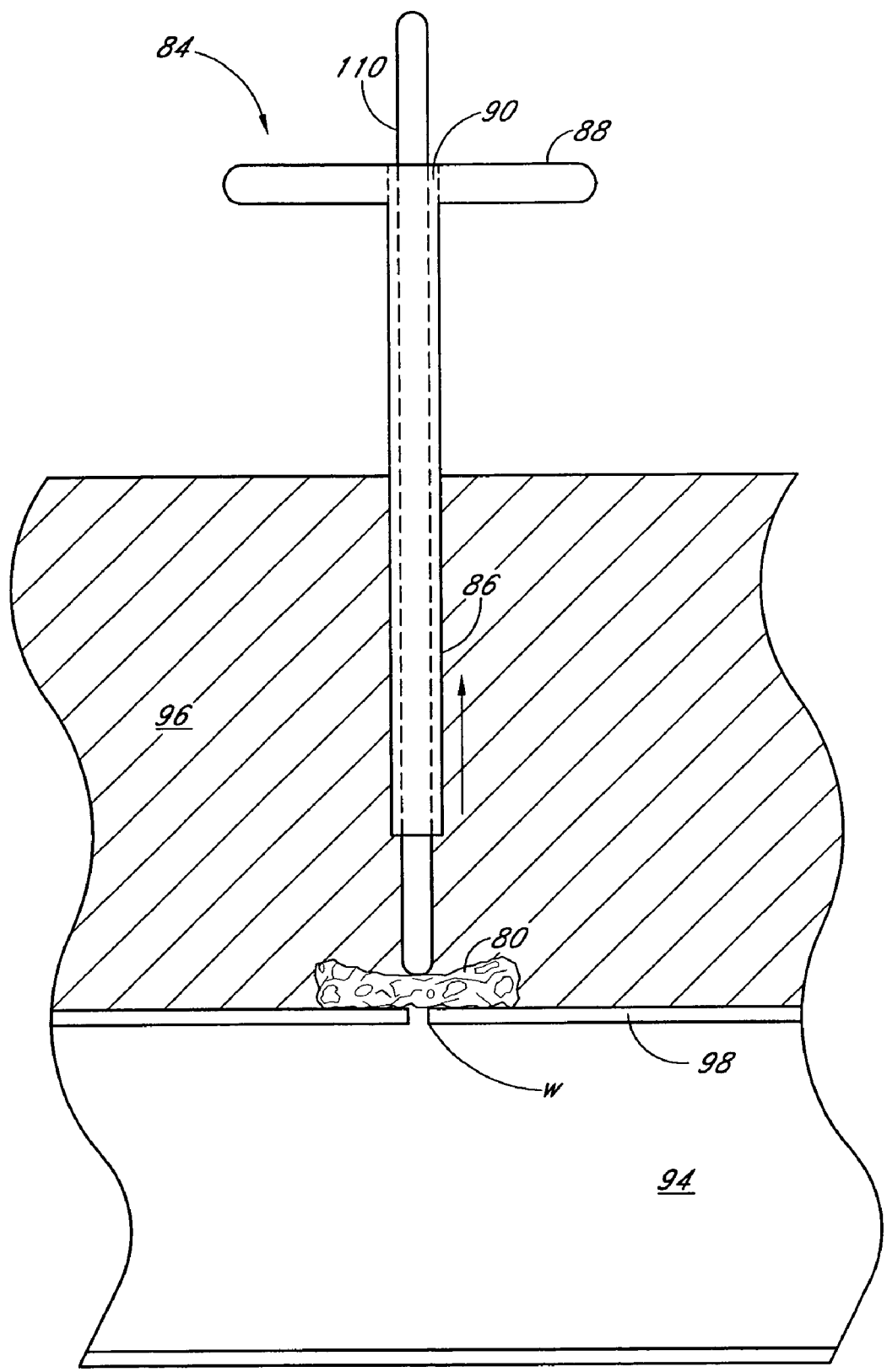
FIG. 10 shows the arrangement of FIG. 8, wherein the push member is being removed from the patient.
Figure 11:
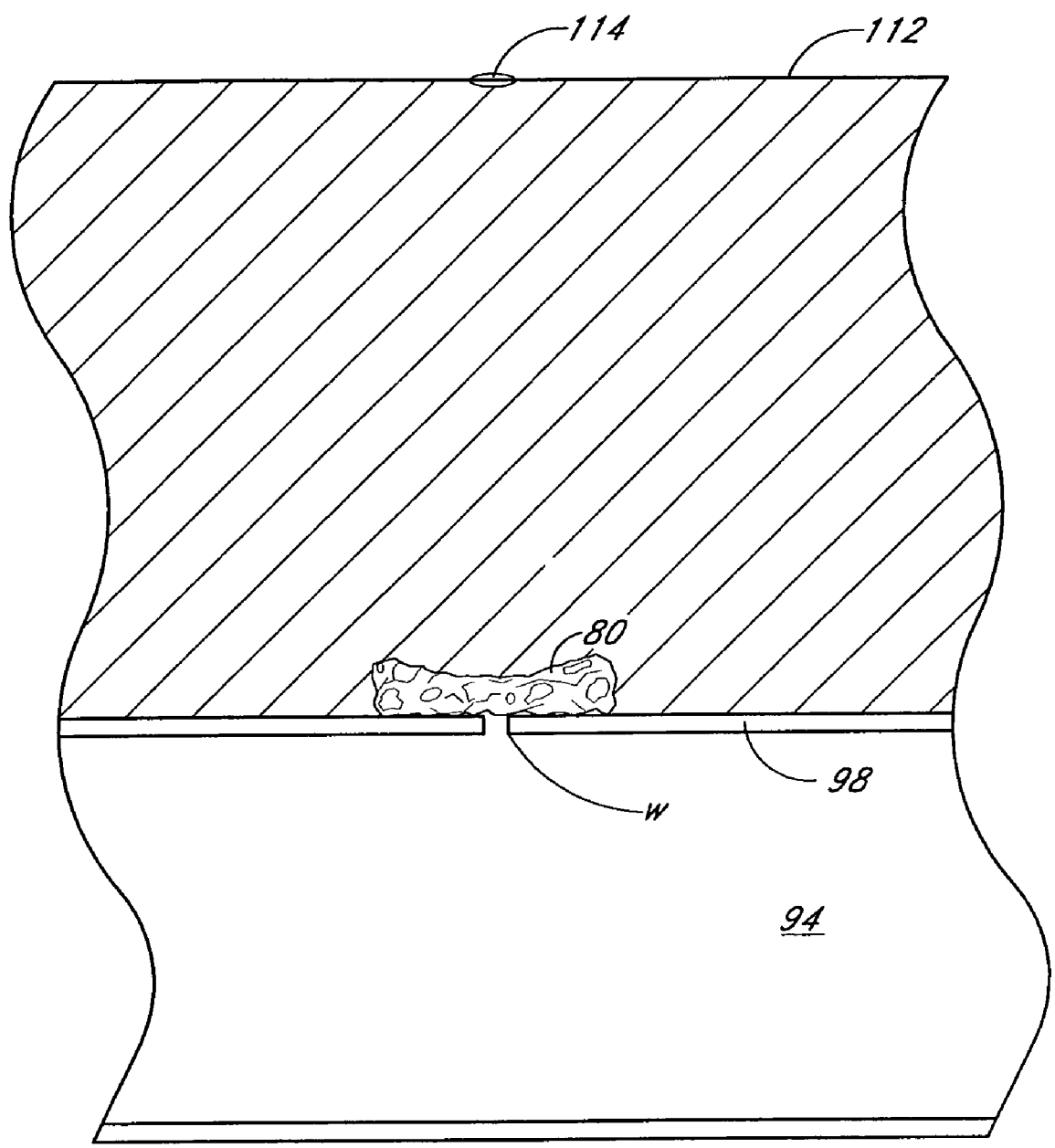
FIG. 11 shows a sealed puncture wound after treatment with an embodiment of the device and method.

Once the sponge 80 is correctly placed, the push member 84 can be removed. Removal of the push member 84 can be aided by a release rod 110 which, as shown in FIG. 10, is advanced through the push member lumen 90 and into contact with the sponge 80. The release rod 110 holds the sponge 80 in place as the push member 84 is withdrawn from the patient. Thus, the release rod 110 engages the sponge 80 so as to provide counter traction when the push member 84 is withdrawn. In this way, the push member 84 can be removed even if some adhesion occurs between the sponge 80 and the push member 84. With reference next to FIG. 11, once the release rod 110 is withdrawn, the patient's skin 112 is closed by any appropriate closure media such as, for example, sutures 114. The hemostatic sponge 80 is left in place. The body's natural blood clotting process will plug and repair the vascular wound w with the aid of the hemostatic sponge 80. Thus, healing will proceed without the danger of false aneurysms, missed or faulty wound closure, or the like.

In the embodiment illustrated in FIGS. 1-9, the catheter comprises a single-lumen catheter. In another embodiment (not shown), the elongate catheter has a first lumen comprising a tube that extends from the distal end opening to the proximal end opening and slidingly accommodates the guidewire therewithin. The outer wall of the catheter defines a second lumen that concentrically surrounds the first lumen. The holes through the outer wall of the catheter open into the second lumen. Additionally, an access lumen communicates with the second lumen. In this embodiment, the distal and proximal openings, which accommodate the guidewire, do not communicate with the second lumen, which lumen communicates with the source of suction through the access lumen. Accordingly, in this embodiment, there may be less of a chance that body fluids will be drawn into the catheter through the distal and proximal guidewire openings than in an embodiment employing a single lumen. However, the single-lumen catheter can be less expensive to manufacture and can be expected to have a smaller diameter than the dual-lumen catheter.

With reference next to FIGS. 12-16, another embodiment of a vascular wound closure apparatus is presented. The apparatus includes a retractor 200 and an elongate catheter 250.

Figure 13:
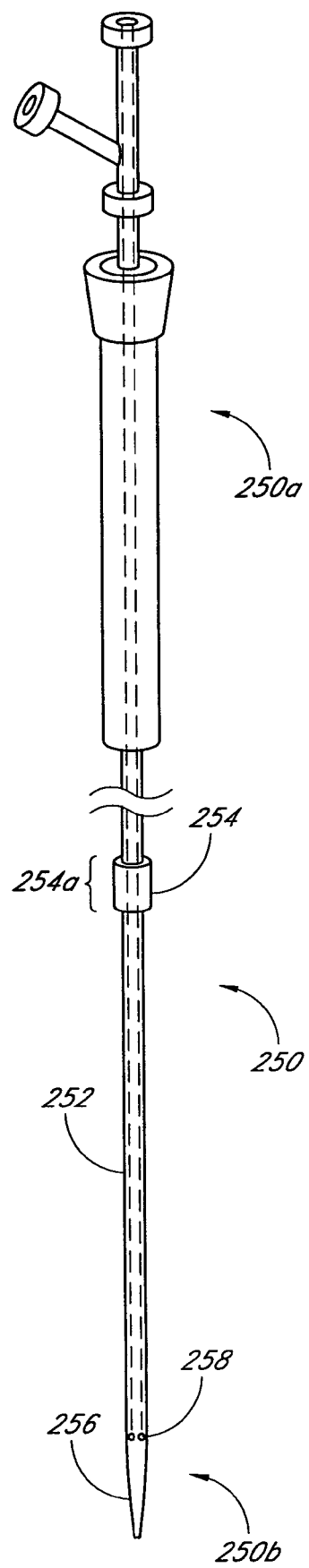
FIG. 13 shows a side view of a catheter for use according to the embodiment illustrated in FIG. 12.

With particular reference to FIG. 13, the catheter 250 has a proximal end 250*a* and a distal end 250*b*. A distal opening is formed through the distal end of the catheter and opens along a longitudinal axis of the catheter. A lumen 250*c* is defined within the catheter. A tip 256 at the distal end 250*b* of the catheter 250 preferably is tapered. A connector portion is provided on the proximal end 250*a*, which connector portion preferably includes a main lumen and a secondary lumen. The main lumen extends along the longitudinal axis of the catheter and is coextensive with the catheter lumen 250*c*. At least one indicator hole 258 is formed through a side wall of the catheter near the distal end. Preferably the catheter 250 is generally straight and is sized between about 4-8 F and more preferably about 6 F.

An outer surface 252 of the catheter 250 preferably has a generally cylindrical shape and includes a raised portion 254. In one preferred embodiment, the raised portion 254 defines a connection between two separate sections (not shown) of the catheter 250. In the illustrated embodiment, the raised portion 254 is cylindrical and includes a length 254*a*.

With continued reference to FIG. 13 a pusher member 260 preferably is movably disposed about the outer surface 252 of the catheter. The pusher member 260 preferably is configured to slide over the catheter 250. The pusher member 260 preferably has an inner lumen having a diameter greater than the raised portion 254 of the catheter 250 so that the pusher member 260 can slide over the raised portion 254.

Figure 12:
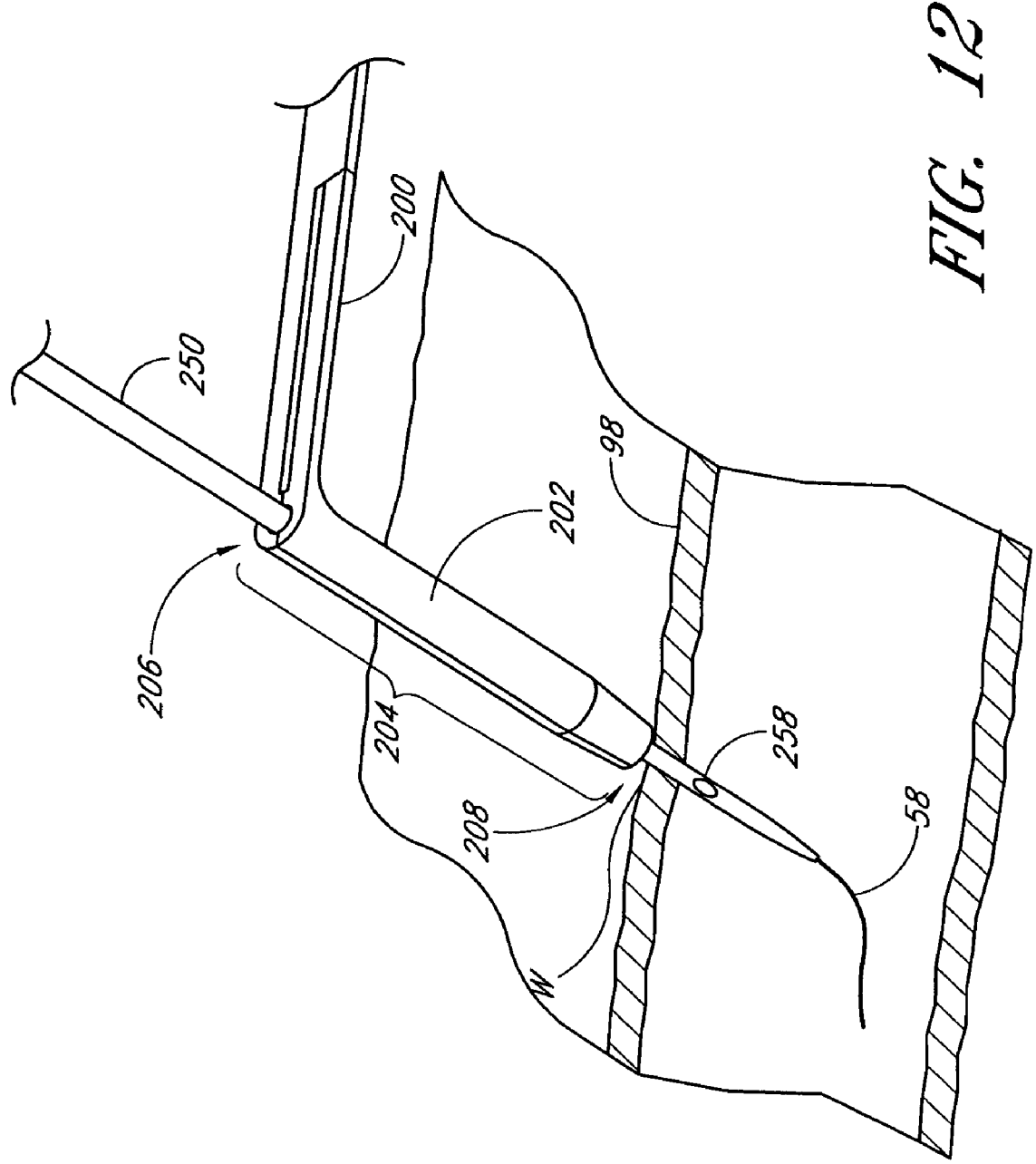
FIG. 12 shows another embodiment of a vascular wound closure apparatus.
Figure 14:
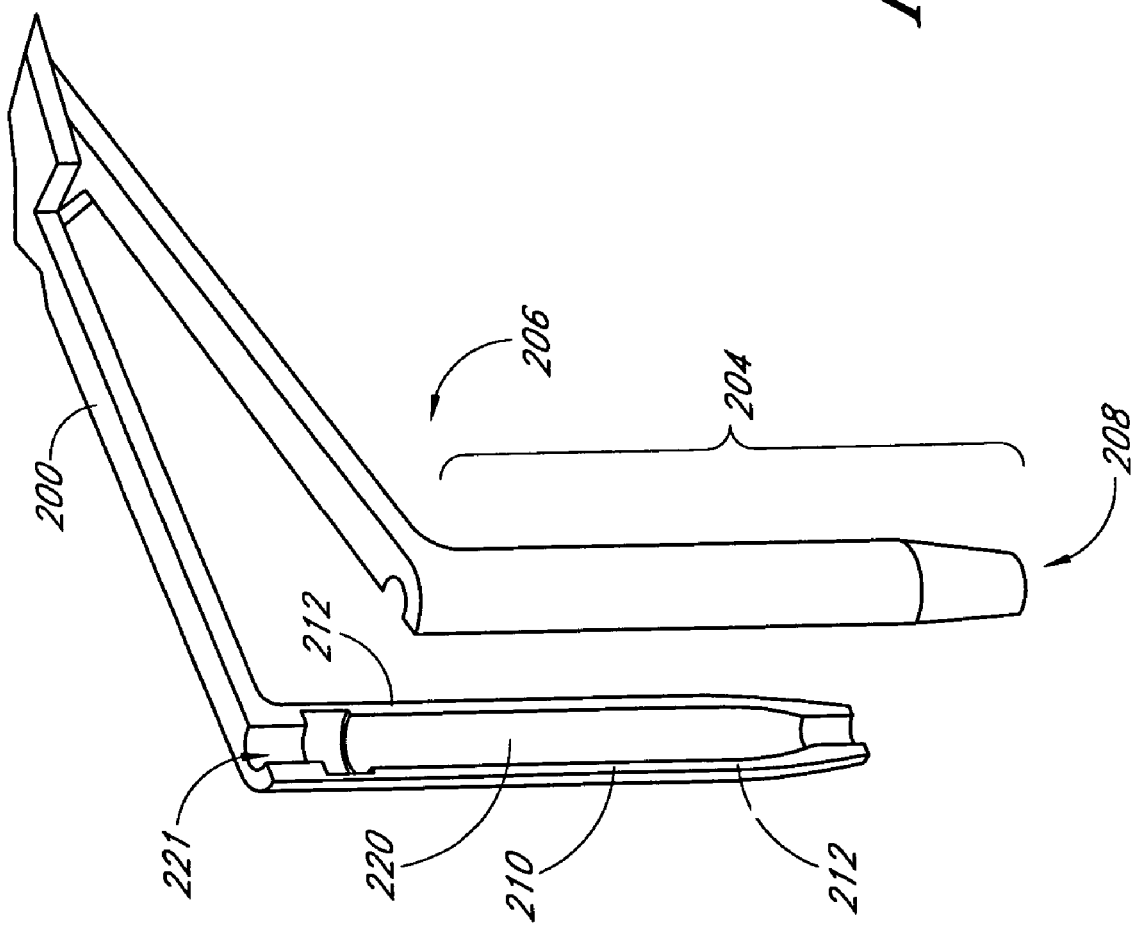
FIG. 14 shows a retractor portion of the apparatus of FIG. 12 with the retractor arms in an open position.
Figure 16:
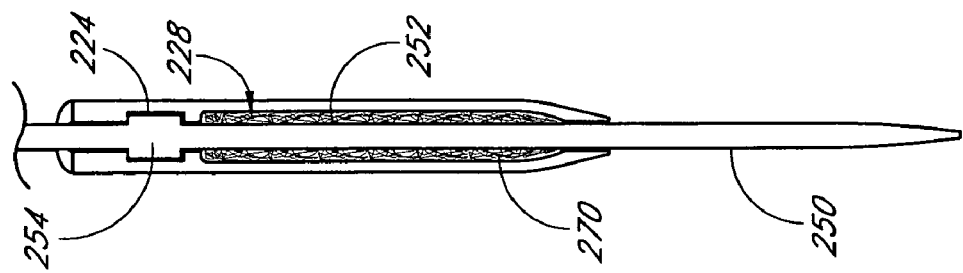
FIG. 16 shows the catheter of FIG. 13 disposed in the retractor arm of FIG. 15.
Figure 15:
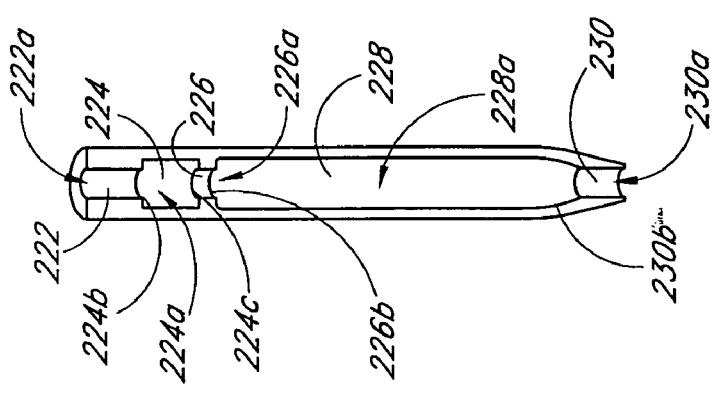
FIG. 15 shows a side plan view of one of the retractor arms illustrated in FIG. 14.

With reference next to FIGS. 14-16, the retractor 200 preferably is configured to be mounted onto the catheter 250. In the illustrated embodiment, the retractor 200 preferably has two retractor arms 202 movably connected to each other, each having a length 204 from a proximal end 206 to a distal end 208. The retractor arms 202 preferably are capable of being moved between an open position (see FIG. 14) and a closed position (see FIG. 12). When in the closed position, as illustrated in FIG. 12, the retractor arms 202 preferably enclose at least a portion of the catheter 250. Although the illustrated embodiment of the retractor 200 shows only two retractor arms 202, it should be understood that the retractor 200 can have more than two retractor arms 202.

With continued reference to FIGS. 14 and 15, each of the retractor arms 202 preferably defines an inner surface 210 generally facing the inner surface 210 of the other arm 202. Each inner surface 210 defines edges 212 that preferably extend along the length 204 of the arms 202. The inner surface 210 also preferably defines a cavity or channel 220 extending between the edges 212. The channel 220 preferably extends the length of the retractor arms 202. When the retractor arms 202 are in the closed position, as shown in FIG. 12, the channels 220 on the retractor arms 202 preferably combine to define a canal 221 extending the length 204 of the arms 202.

With reference to FIGS. 14-15, the channel 220 preferably comprises a proximal portion 222 disposed at the proximal end 206 of the retractor arms 202. In a preferred embodiment, the proximal portion 222 has a generally curved shape configured to removably receive and substantially contact and hold at least a portion of the catheter 250 in a fixed position when the retractor arms 202 are in the closed position. The proximal portion 222 also has a depth 222*a* generally orthogonal to the length 204 of the retractor arms 202. For example, the proximal portion 222 can have a semi-circular cross-section with a radius 222*a* about the same as that of an outer surface 252 of the catheter 250. However, the proximal portion 222 can have any shape configured to substantially contact the catheter 250 when the retractor arms 202 are in the closed position. Most preferably, the proximal portion 222 is sized and configured generally complementary to the catheter 250 so that the retractor 200 holds the catheter 250 generally snugly at the proximal portion 222.

With continued reference to FIGS. 15 and 16, the channel 220 preferably comprises a receiver portion 224 adjacent the proximal portion 222. The receiver portion 224 preferably has a generally curved shape and has a depth 224a generally orthogonal to the length 204 of the arms 202 that is greater than the depth 222a of the proximal portion 222. Accordingly, the receiver portion 224 defines an edge 224b between the receiver portion 224 and the proximal portion 222. The illustrated receiver portion 224 has a semi-circular cross-section with a radius 224a that is greater than the radius 222a of the proximal portion 222. Most preferably, the receiver portion 224 is generally complementary to the catheter raised portion 254 so as to receive the raised portion 254 therein.

The channel 220 also preferably comprises a contact portion 226 adjacent the receiver portion 224. Similar to the proximal portion 222, the contact portion 226 preferably is generally complementary to the catheter outer surface 252 and is configured to removably receive, and to substantially contact and hold the catheter 250 when the retractor arms 202 are in the closed position. The contact portion 226 preferably has a depth 226a generally orthogonal to the length 204 of the retractor arms 202. In one preferred embodiment, the depth 216a is similar to the depth 222a of the proximal portion 222. For example, the contact portion 226 can have a semi-circular cross-section with a radius 226a about the same as the radius 222a of the proximal portion 222. The depth 226a of the contact portion 226 is also preferably smaller than the depth 224a of the receiver portion 224, so that the receiver portion 224 defines an edge 224c between the receiver portion 224 and the contact portion 226.

With reference still to FIGS. 15 and 16, in the illustrated embodiment, the proximal portion 222 and contact portion 226 each are smaller than the receiver portion 224. Most preferably, the proximal portion 222 and contact portion 226 are configured so that the catheter raised portion 254 cannot slide through either portion 222, 226. Thus, when the raised portion 254 is disposed in the receiver portion 224 as shown in FIG. 16, the raised portion is constrained from moving proximally or distally. As such, the entire catheter 250 is longitudinally locked in place relative to the retractor 200 when the retractor arms 202 are closed about the catheter as shown in the FIG. 12.

The channel 220 further preferably comprises a compartment portion or chamber 228 adjacent the contact portion 226. The chamber 228 preferably has a generally curved shape and a depth 228a generally orthogonal to the length 204 of the retractor arms 202 greater than the depth 226a of the contact portion 226. For example, the chamber 228 can have a semi-circular cross-section with a radius 228a greater than the radius 226a. Further, the contact portion 226 defines an edge 226b between the contact portion 226 and the chamber 228. The chamber 228 is configured to receive a portion of the catheter 250 therein and to define a space 228b between the catheter 250 and the retractor arms 202. When the retractor arms 202 are in the closed position, the space 228b extends generally about the entire circumference of the catheter 250. The space 228b is configured to receive and accommodate a hemostatic material 270 therein so that it surrounds at least a portion of the outer surface 252 of the catheter 250. The hemostatic material 270 is further described below.

A distal portion 230 of the channel is defined adjacent the chamber 228 and has a depth 230a generally orthogonal to the length 204 of the retractor arms 202 smaller than the depth 228a of the chamber 228. The distal portion 230 preferably is generally complementary to the catheter outer surface 252 so as to substantially contact and hold the catheter 250 when the retractor arms 202 are in the closed position. For example, the distal portion 230 can have a semi-circular cross-section with a radius 230a. In one preferred embodiment, the radius 230a is about the same as the radius 226a of the contact portion 226 and/or the radius 222a of the proximal portion 222. A generally smooth transition section 230b preferably connects the chamber portion 228 and the distal portion 230.

With reference again to FIGS. 12-16, in practice, the hemostatic material 270 is preferably disposed about the outer surface 252 of the catheter 250 at a location between the raised portion 254 and the catheter holes 258. The catheter 250 is placed in the channel 220, while the arms 202 are in the open position, so that the raised portion 254 is disposed in the receiver portion 224 and the hemostatic material 270 is housed in the chamber 228. Preferably, the catheter 250 and retractor 200 are configured so that, when assembled, the distance between the distal end 208 of the retractor arms 202 and the indicator holes 258 is at least the same as the width of an artery wall. Preferably, said distance is at least about 0.5 to 2 millimeters.

When the retractor arms 202 are moved into the closed position with the raised portion 254 disposed in the receiver portion 224, the catheter 250 is longitudinally locked relative to the retractor 200. Thus, the catheter 250 and retractor 200 will move together even if longitudinal forces are exerted upon one or the other structure. In use, the apparatus is advanced into the patient so that the catheter 250 is advanced into the wound "w" as discussed above in connection with the embodiment discussed in connection with FIGS. 1-4. When blood "b" is observed in a viewing port (not shown) connected to the catheter 250, the retractor arms 202 are then preferably moved into the open position. The pusher member 260 is then advanced toward the distal end 250b of the catheter 250 to engage and advance the hemostatic material 270 into contact with the wound w.

In the embodiment illustrated in FIGS. 12-16, the hemostatic material 270 preferably comprises a malleable, fibrous material. For example, preferably the substrate comprises a puff—a fibrous, cotton-like material that can be manipulated into a suitable shape or size so as to accommodate a particular wound configuration. Most preferably, the hemostatic material 270 comprises a puff prepared from chitosan fibers and infused with microporous polysaccharide microspheres. Applicants' copending application "Deployable Multifunctional Hemostatic Agent" discusses such a hemostatic puff and methods of depositing microporous polysaccharide microspheres thereon. Other fibrous substrates and hemostatic agents may also be employed in other embodiments.

In still other embodiments, the hemostatic material 270 can be infused with any number of medications associated with the treatment of wounds. For example, antibiotic and anti-inflammatory medications may be further infused or deposited on a substrate.

It is further to be understood that, in accordance with further embodiment, the raised portion 270 can have various configurations. For example, the raised portion may not extend circumferentially about the catheter 250, and a plurality of raised portions may be employed. Preferably, the receiver portion of the retractor 200 is shaped complementary to the raised portion. Additionally, the inner lumen of the pusher member 260 may have a cross sectional shape configured to fit over the raised portion, and may in some embodiments be non-circular.

With reference next to FIGS. 17-23, another embodiment of a vascular wound closure assembly 300 comprises a catheter 310 having a proximal end 312 and a distal end 314, and defining a lumen (not shown) therebetween. A pusher member 330 having a proximal end 332 and a distal end 334 is slidably disposed on the catheter 310. A delivery tube 350 having a proximal end 352 and a distal end 354 is slidably disposed on the catheter 310 and is positioned distal of the pusher member 330. The closure assembly 300 preferably is made of a polymeric material, such as polypropylene. Preferably, the assembly 300 is also made of hypoallergenic materials.

Figure 18:
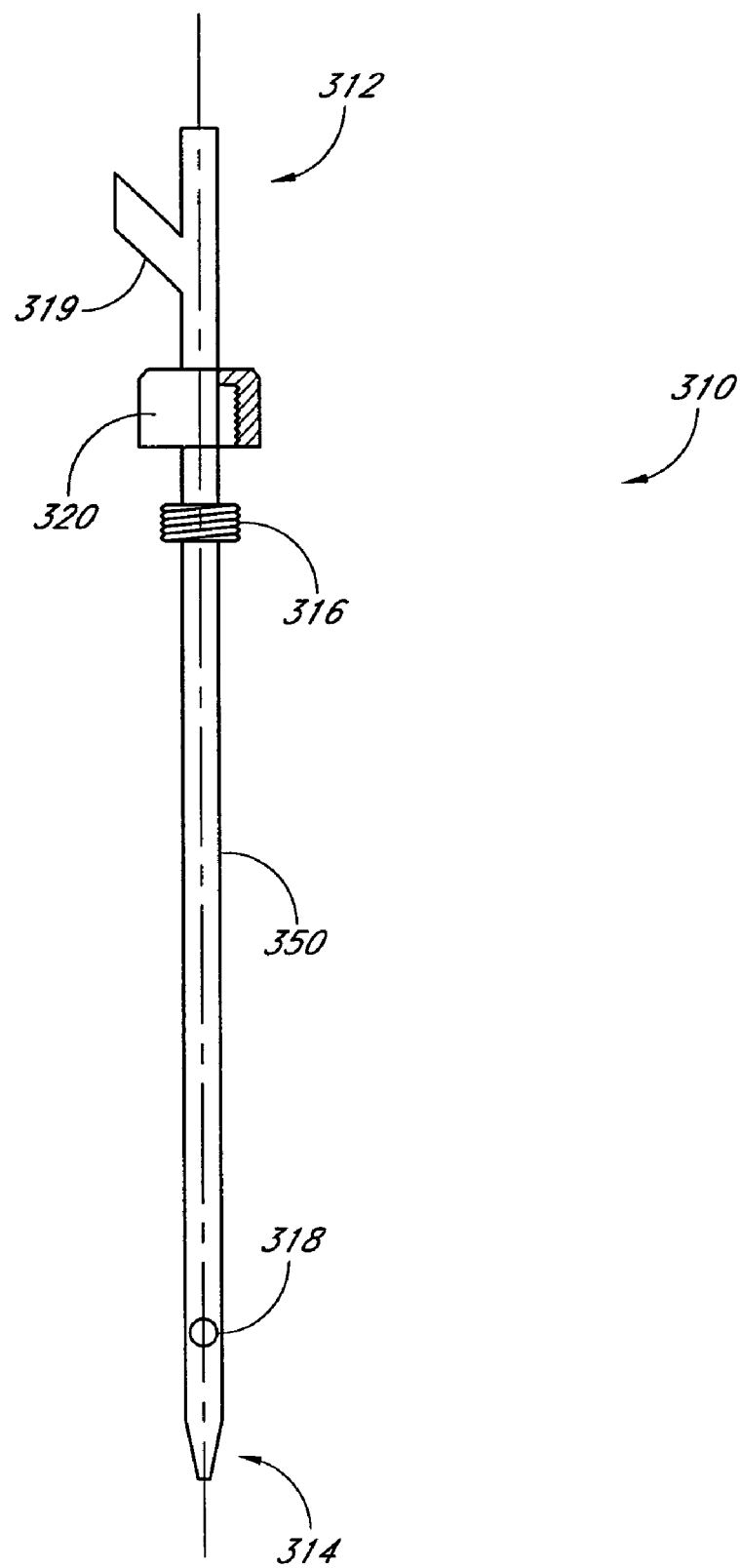
FIG. 18 shows a side view of a catheter according to the embodiment illustrated in FIG. 17.

With particular reference to FIG. 18, the catheter 310 preferably comprises a stop member 316 disposed in a fixed position about the catheter surface 310*a*. The distal end 314 preferably is tapered, and catheter holes 318 are formed through a side of the catheter 310 proximal of the distal end 314. In one embodiment, the catheter 310 preferably comprises a secondary branch 319 disposed at the proximal end 312, and having a secondary lumen (not shown) connected to the lumen of the catheter 310. The secondary branch 319 preferably is configured to operatively connect to a variety of devices used in the closure of vascular wounds, such as a suction device. For example, in one embodiment, a syringe can be connected to the secondary branch 319 to pull a vacuum through the catheter 310.

A coupling member 320 preferably is movably disposed about the catheter 310 and is configured to mechanically couple to the stop member 316. In the illustrated embodiment, the stop member 316 is threaded on its outer surface and the coupling member 320 is threaded on its inner surface so that the respective threads are engageable so that the coupling member 320 and catheter 310, when engaged, do not move longitudinally relative to one another. As such, the member 320 and catheter 310 are releasably coupled to one another. In other embodiments, other suitable mechanical coupling mechanisms can be used. For example, a detent and catch mechanism or a j-lock mechanism can also be acceptably employed.

In this description, the term releasably coupled is a broad term used in its ordinary sense and referring to, without limitation, to members being attached or affixed to one another in a manner so that they can be decoupled from one another. For example, without limitation, members can be coupled with threads, a detent mechanism, a conformed yet breakable bridge, such as flashing from injection-molding, an adhesive, or the like.

Figure 19:
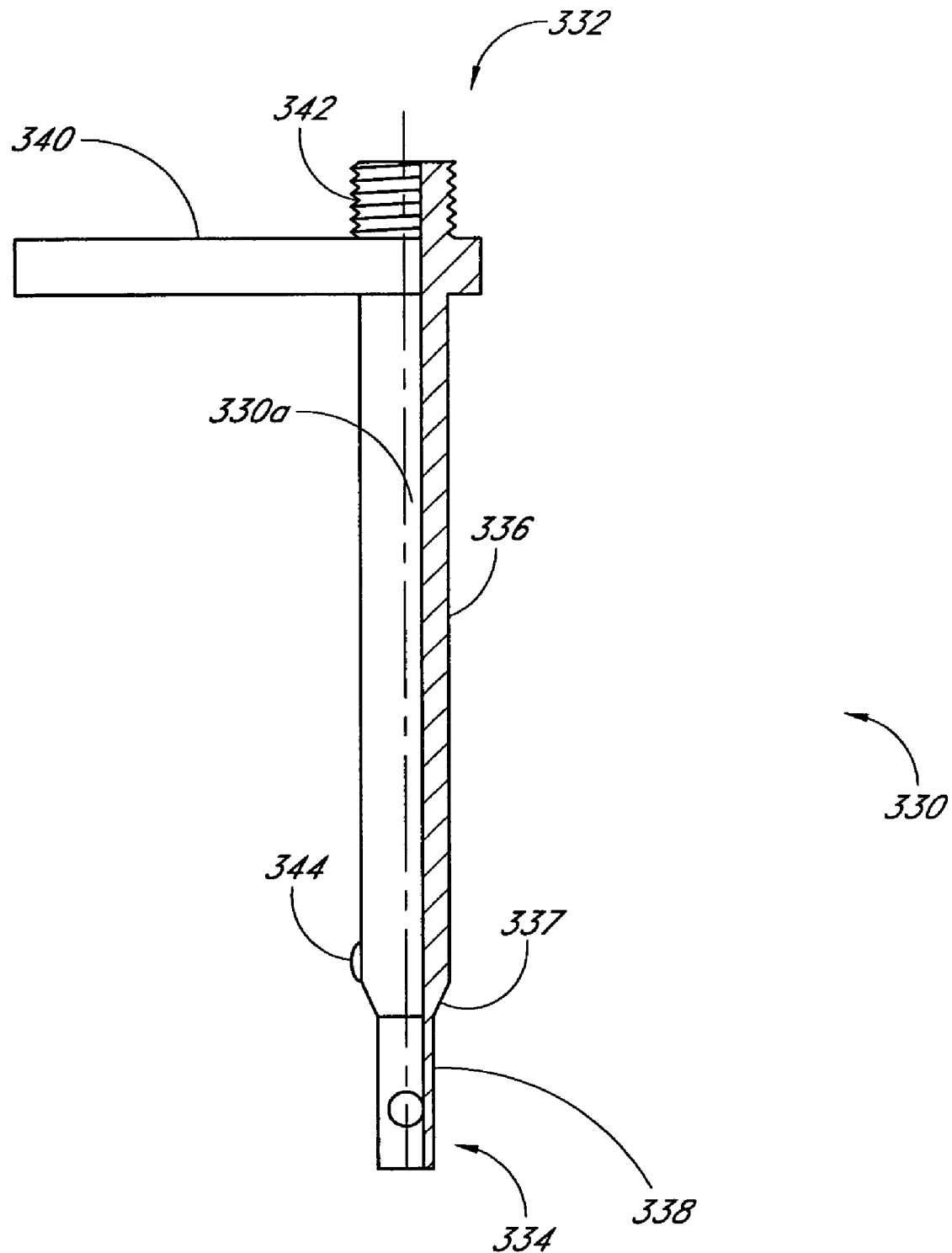
FIG. 19 shows a partially cutaway view of a pusher member according to the embodiment illustrated in FIG. 17.

With particular reference next to FIG. 19, the pusher member 330 preferably comprises a generally cylindrical central portion 336, a generally conical transition portion 337 and a generally cylindrical distal portion 338. The diameter of the central portion 336 preferably is larger than the diameter of the distal portion 338. The pusher member 330 preferably defines a canal 330*a* that extends from the proximal end 332 to the distal end 334 and which is preferably configured to slidably receive the catheter 310, therethrough. For example, the canal 330*a* can have a circular cross-section with a diameter larger than the diameter of the catheter surface 310*a*. However, the canal 330*a* is not large enough to fit over the catheter stop member 316. As such, the pusher member 330 cannot be moved proximally over the catheter 310 beyond the stop member 316.

The pusher member 330 preferably comprises a handle 340 near the proximal end 332. It is to be understood that the pusher member 330 can comprise more than one handle 340.

Figure 27:
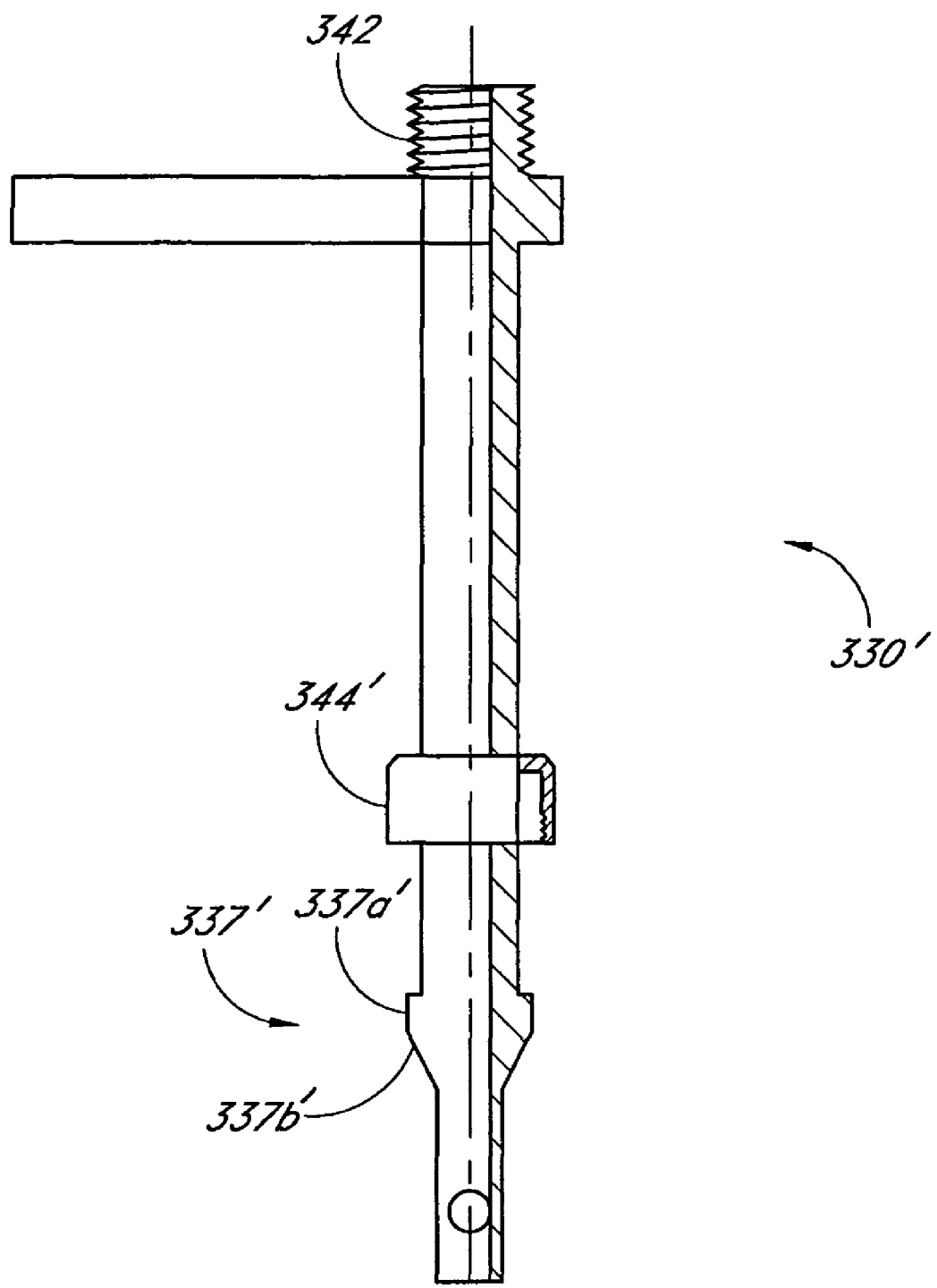
FIG. 27 shows a partially cutaway cross-sectional view of a pusher member according to the embodiment illustrated in FIG. 25.

A proximal coupling member 342 is disposed at the proximal end 332. In the illustrated embodiment, the proximal coupling member 342 comprises threads on its outer surface sized and configured to engage the threads of the coupling member 320. As shown in FIG. 27, the catheter coupling member 320 is configured to engage both the stop member 316 and the pusher member proximal coupling member 342 so as to selectively hold the pusher 330 longitudinally fixed relative to the catheter 310.

A distal coupling member 344 is disposed proximal the transition portion 337. In the illustrated embodiment, the distal coupling member 344 comprises a generally hemispherical raised portion.

Figure 20:
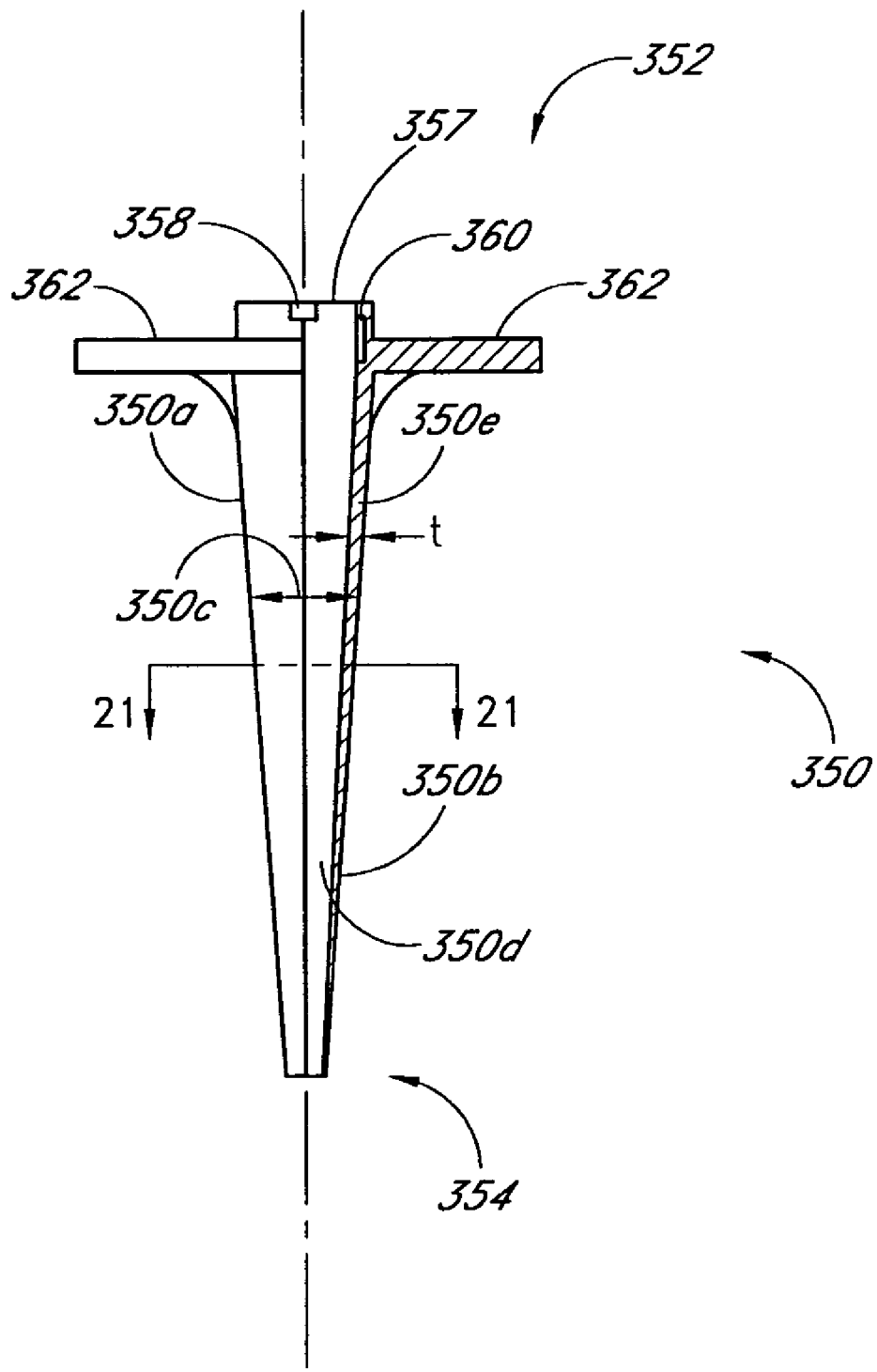
FIG. 20 shows a partially cutaway view of a delivery tube according to the embodiment illustrated in FIG. 17.
Figure 21:
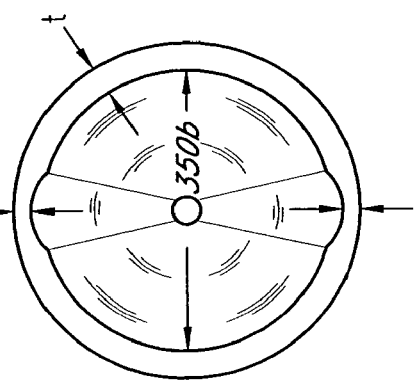
FIG. 21 shows a cross section of the delivery tube of FIG. 20 taken along line 21-21.

With particular reference next to FIGS. 20-21, the delivery tube 350 preferably has a body 350*a* with a conical outer surface 350*b* having a generally decreasing diameter 350*c* between a top edge 357 at the proximal end 352 and the distal end 354. A wall 350*e* of the delivery tube 350 has a thickness "t". The delivery tube wall 350*e* preferably defines a chamber 350*d* extending from the proximal end 352 to the distal end 354 The chamber 350*d* preferably is conical in shape, and preferably is configured to receive hemostatic material 270 therein between the catheter and the wall. The proximal end 352 of the delivery tube 350 also is preferably configured to receive at least a distal portion of the pusher member 330. The distal end 354 of the delivery tube 350 has a distal opening that is configured to receive the catheter 310 extending therethrough.

With particular reference to FIG. 21, the delivery tube 350 preferably comprises weakened portions 356. In the illustrated embodiment, the weakened portions 356 comprise portions of the tube 350 having a reduced thickness "t". The reduced thickness weakened portions 356 preferably extend from at or near the proximal end 352 to the distal end 354 of the delivery tube 350. The weakened portions 356 define a preferential breaking or deformation zone of the delivery tube 350 so that when a force beyond a specified threshold is applied, the tube will deform or break in the vicinity of the weakened portions 356. In the illustrated embodiment, the delivery tube 350 has two weakened portions 356 comprising elongate sections of reduced thickness "t" diametrically opposed to each other. Preferably, the elongate weakened portions 356 extend the entire length of the delivery tube 350.

In accordance with this description, the term weakened portion is a broad term used in its ordinary sense and referring to, without limitation, a zone or area that preferentially breaks, bends, stretches, expands or otherwise deforms upon application of a threshold force. In the illustrated embodiment, the weakened portions comprise portions that are relatively thin. In accordance with other embodiments, a weakened portion can include, without limitation, a portion of material that is scored, perforated, physically or chemically treated, or the like. Further, a weakened portion can comprise an elastic or easily deformable material that may or may not be a different material than the rest of the member.

In the illustrated embodiment, as shown in FIG. 21, the delivery tube 350 has two weakened portions 356. However, it is to be understood that the delivery tube 356 can have one or a plurality of weakened portions 356.

In one embodiment, the delivery tube 350 preferably comprises separation starter portions 358 disposed at the proximal end 352. The starter portions 358 are preferably disposed adjacent and aligned with the weakened portions 356. In the illustrated embodiment, the starter portions 358 are notches 358 aligned with the weakened portions 356. In other embodiments starter portions 358 can be provided having other shapes.

Figure 22:
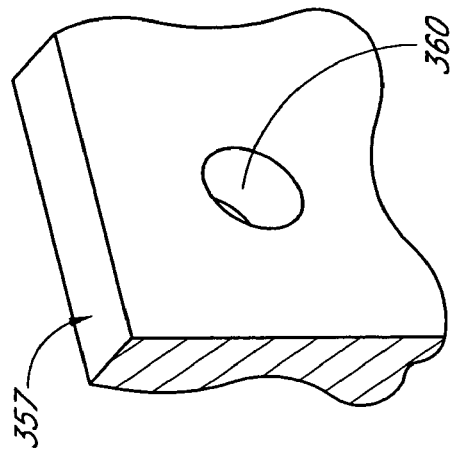
FIG. 22 shows a wall portion of the delivery tube of FIG. 20 having a detent catch coupling portion.

The delivery tube 350 further comprises a coupling portion 360 disposed at the proximal end 352. The coupling portion 360 preferably is configured to mechanically couple to the pusher member distal coupling member 344. With reference to FIG. 22, the illustrated coupling portion 360*a* comprises a catch configured to releasably hold the raised portion of the pusher member distal coupling member 344. To engage the coupling portions 244, 260, the delivery tube 350 is moved longitudinally relative to the pusher member 344 until the catch is aligned with the raised portion, at which time the raised portion will enter the catch. The catch and raised portion are configured so that the raised portion will exit the catch only upon application of a threshold force. Thus, the pusher member 330 and tube 350 are releasably coupled and longitudinally fixed relative to one another.

With reference again to FIG. 20, the delivery tube 350 comprises a handle 362 disposed adjacent the proximal end 352. The handle 362 preferably comprises two opposing support arms that extend outward from the conical outer surface 350b at locations spaced from the weakened portions 356. In the illustrated embodiment, the delivery tube handle 362 comprises two support arms diametrically opposed to each other and disposed generally 90° from the weakened portions 356.

With reference again to FIG. 17, the vascular wound closure assembly 300 is assembled by sliding the distal end 314 of the catheter 310 through the canal 330a of the pusher member 330 so that the proximal end 332 of the pusher member 330 preferably abuts the stopper member 316, and so the distal end 314 of the catheter 310 extends out from the distal end 334 of the pusher member 330. The coupling member 320 engages the stop member 316 and pusher member proximal coupling member 342 so that the pusher member 330 is fixed longitudinally to the catheter 310.

The proximal end 352 of the delivery tube 350 is slid over the distal end 314 of the catheter 310 so that the catheter 310 travels through the opening 350d. As the delivery tube 350 is slid proximally over the catheter 310 the coupling portion 360 mechanically engages the distal coupling member 344 of the pusher member 330. As such, the catheter 310, pusher member 330 and delivery tube 350 are fixed longitudinally to one another. Thus, the pusher member and tube move together as a unit. The hemostatic material 270 can be added to the chamber 350d of the delivery tube 350 before or during the assembly process.

Figure 17:
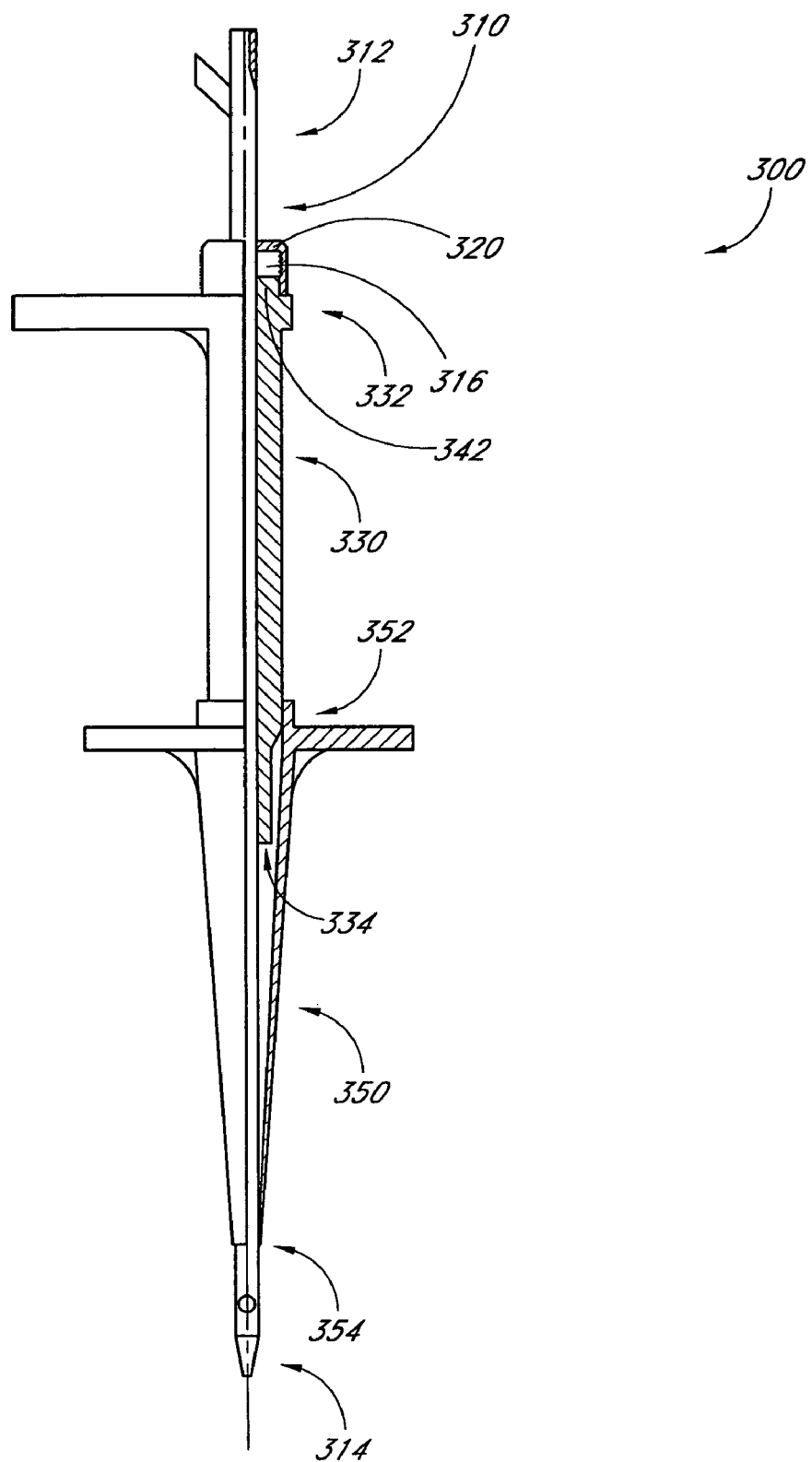
FIG. 17 shows a partially cutaway view of another embodiment of a vascular wound closure apparatus.

With continued reference to FIG. 17, when the apparatus is assembled, the distal end 314 of the catheter 310 extends from the distal end 354 of the delivery tube 350, and the catheter holes 318 preferably are spaced from the distal end 354 a distance at least the same as the width of an artery wall. Preferably, the distance is about 0.5 to 2 millimeters.

To use the apparatus, the assembled device is advanced into the vascular wound "w" in a manner similar to that discussed above in connection with FIGS. 1-4. When the device is positioned so that the distal end 354 of the delivery tube 350 is generally adjacent the wound "w", the coupling member 320 preferably is disengaged from the stop member 316 of the catheter 310 and the proximal coupling member 342 of the pusher member 330. Similarly, the coupling portion 360 of the delivery tube 350 preferably is disengaged from the distal coupling member 344 of the pusher member 330. Accordingly, the pusher member 330 and delivery tube 350 are no longer longitudinally fixed relative to each other.

Figure 23:
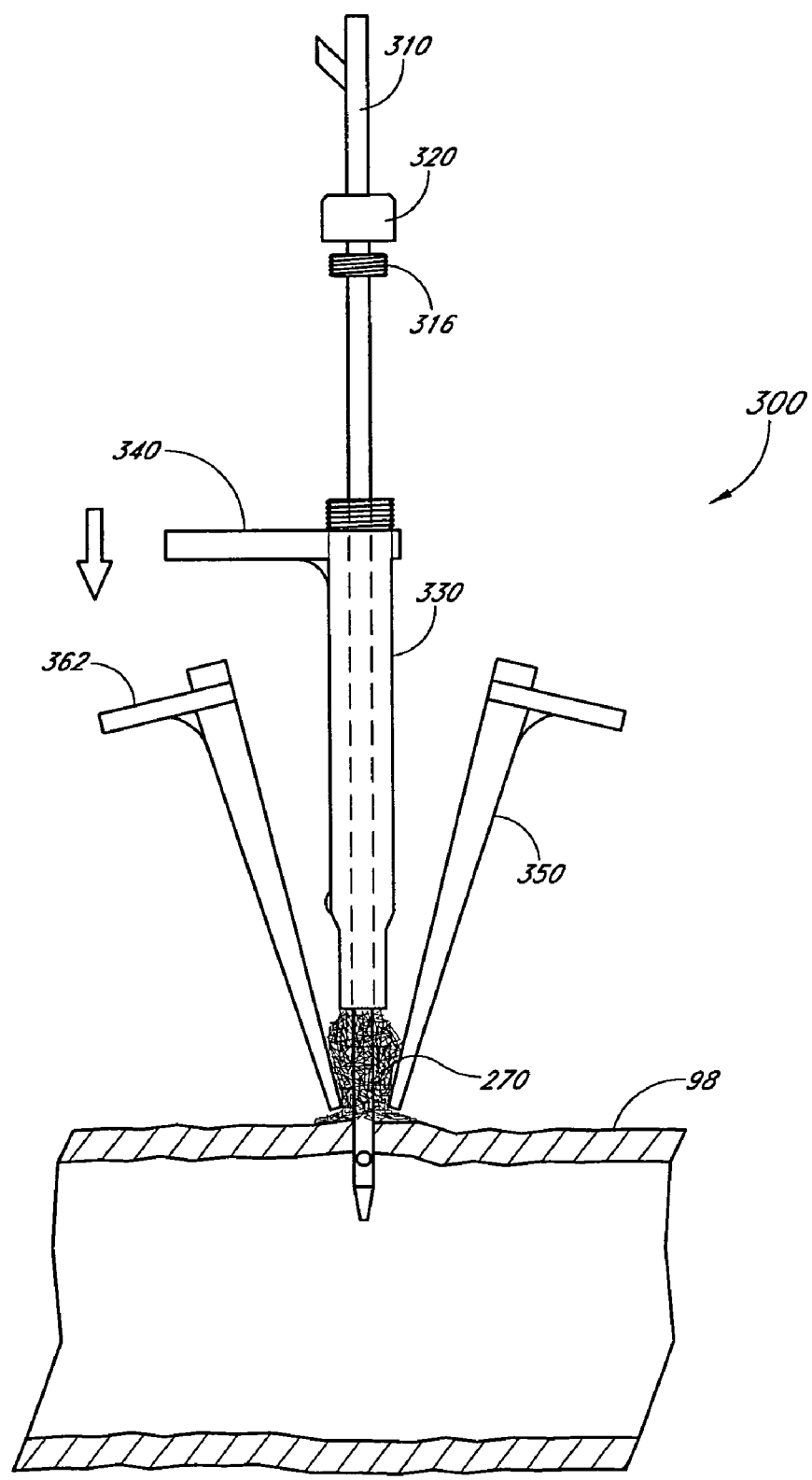
FIG. 23 shows the apparatus of FIG. 12 during use.

With reference next to FIG. 23, the pusher member 330 is then preferably advanced distally into the opening 350d of the delivery tube 350 while the delivery tube 350 is held generally stationary adjacent the wound w. Since the pusher member 330 is generally larger in diameter than the delivery tube 350, the delivery tube 350 breaks along the weakened portions 356 as the pusher member 330 is advanced. In one embodiment, a user grasps the handle 340 of the pusher member 330 and the handle 362 of the delivery tube 350 to drive the pusher member 330 through the delivery tube 350.

As the delivery tube 350 breaks, openings are created so that the hemostatic material 270 is free to exit the chamber. As the pusher member 330 advances, it engages and advances the hemostatic material 270 out of the tube 350 and into contact with the wound "w". Preferably, the broken portions of the delivery tube 350 are removed from the wound location.

As described above in connection with other embodiments, the catheter 310 can be slidably withdrawn through the canal 330a of the pusher member 330. Further, a release rod (not shown) can also be used to provide counter traction to help remove the pusher member 330 from the wound location. For example, the release rod can be slidably inserted through the canal 330a of the pusher member 330 so that it engages the hemostatic material 270 against the wound location. A user can then remove the pusher member 330 without disturbing the hemostatic material 270 because the counter traction provided by the release rod will keep the hemostatic material 270 in place as the pusher member is removed.

In the embodiment discussed above, the coupling members are disengaged before advancing the pusher member relative to the delivery tube. It is to be understood that, in other embodiments, the coupling members can be adapted so that mere application of a force above a threshold force level will defeat the coupling members so as to release the releasably coupled members from one another. Thus, as the user applies force to advance the pusher member, the user simultaneously disengages the coupling members and advances the pusher member.

In another embodiment, the distal coupling member of the pusher member is threaded on its outer surface, and the proximal coupling member of the delivery tube is threaded on its inner surface. As such the pusher member and delivery tube are threadably affixed to each other. In this arrangement, the pusher member is advanced relative to the delivery tube by threading the pusher member. This arrangement allows the user to adjust the distance between the distal ends of the delivery tube and the catheter indicator holes. When the device is positioned so that the delivery tube is adjacent the wound, the pusher member is advanced by continuing to thread the pusher member into the delivery tube as the delivery tube is held in place. As such, the pusher member will advance, and will eventually break the tube at the weakened portions. The pusher member can then be advanced further by using the handles.

Figure 24:
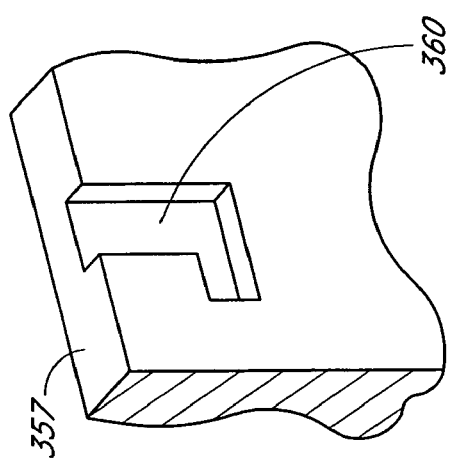
FIG. 24 shows a wall portion of another embodiment of a delivery tube having a j-lock coupling portion.

In still other embodiments, other types and structures of coupling members can be employed. For example, various releasable locking structures can be employed, such as a J-lock or an L-lock (see FIG. 24). Additionally, in still further embodiments, the coupling members can have still different structure. For example, the coupling member can comprise an adhesive between the pusher member and catheter, which adhesive is configured to be defeated upon application of a threshold force. In yet a further embodiment, the pusher member and catheter are lightly heat bonded or otherwise bonded together. As such, the bond between the pusher member and catheter will be overcome upon application of a threshold force.

FIGS. 25-28 illustrate another embodiment of a vascular closure apparatus 300' having many aspects similar to the embodiment described above with reference to FIGS. 17-23. Where possible, the same reference numerals are used to identify similar elements, but elements of the present embodiment include the appellation "'".

Figure 25:
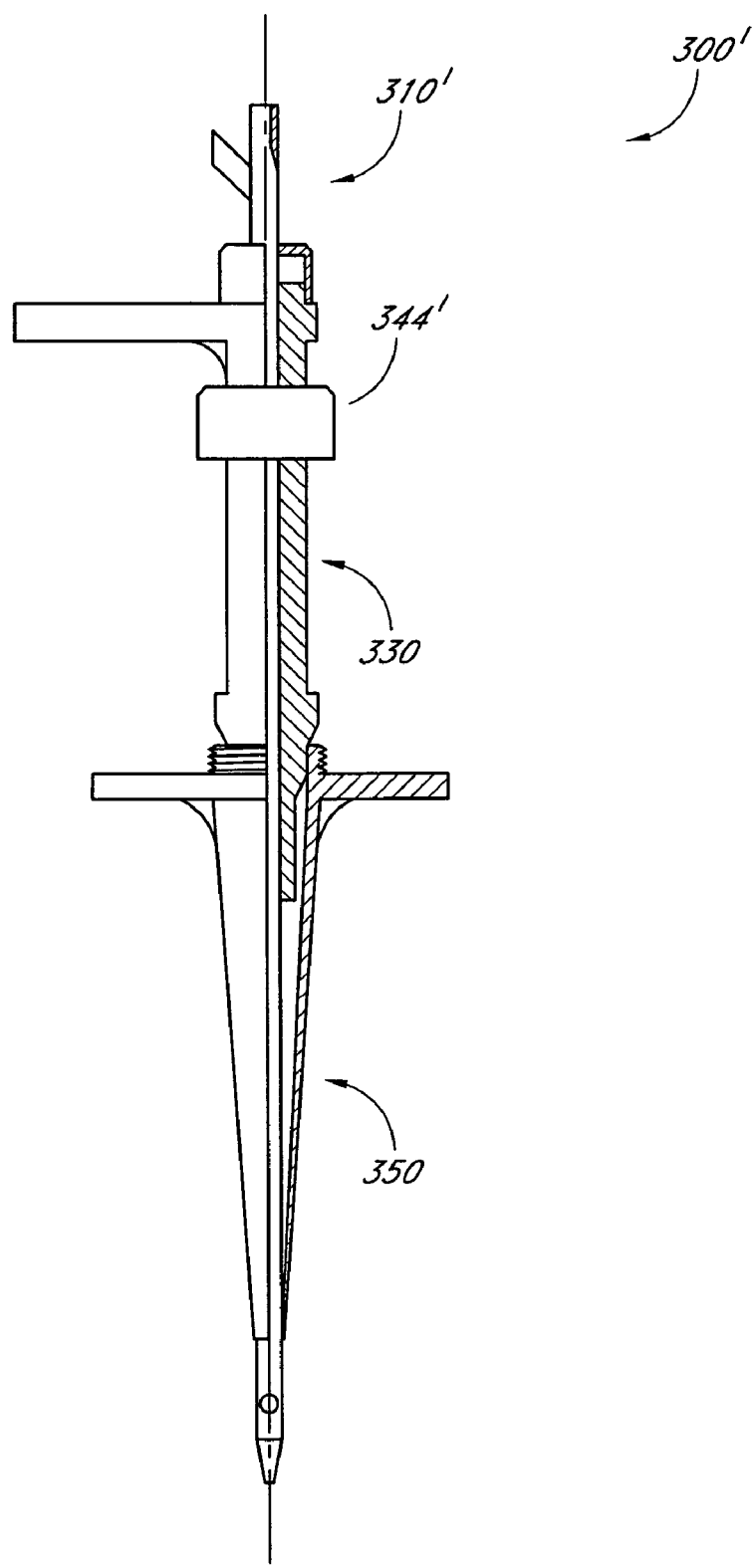
FIG. 25 shows another embodiment of a vascular wound closure apparatus.

With specific reference to FIG. 25, the closure apparatus 300' preferably comprises a catheter 310', a pusher member 330', and a delivery tube 350' releasably connected to each other. Additionally, the apparatus 300' preferably comprises a threaded coupling member 344' slidably disposed about the pusher member 330'.

Figure 26:
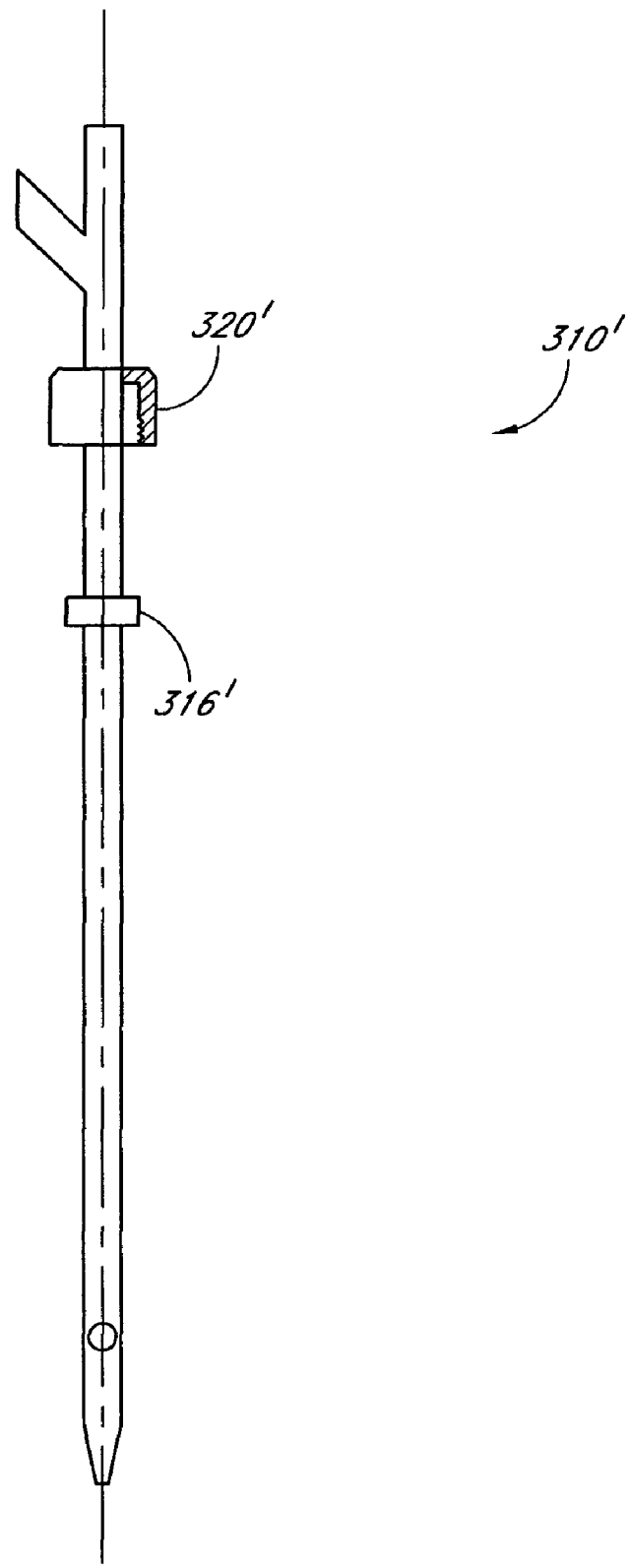
FIG. 26 shows a partially cutaway side view of a catheter according to the embodiment illustrated in FIG. 25.

With specific reference next to FIG. 26, the catheter 310' preferably comprises an unthreaded stop member 316'. Additionally, a coupling member 320' preferably is configured so that a portion of the coupling member is slidable over the stop member 316' so as to enclose it. However, a proximal portion of the coupling member cannot slide over the stop member 316', and thus the stop member limits the distal travel of the coupling member.

With reference next to FIGS. 25 and 27, the proximal end 332 of the pusher member 330' is configured to abut against the stop member 316' when the pusher member 330' is slidably disposed on the catheter 310'. The threaded outer surface of the proximal coupling member 342 preferably is configured to mechanically engage the threads of the coupling member 320' when said member 320' is advanced over the proximal end 332 of the pusher member 330'.

The pusher member 330' preferably comprises a transition portion 337' adjacent the distal portion 338. The transition portion 337' preferably comprises a cylindrical raised portion 337a' and a generally conical portion 337b'. The raised portion 337a' comprises an unthreaded outer surface, and preferably is configured to slidably receive a distal portion of the coupling member 344' about and over its outer surface so that the coupling member 344' encloses the raised portion 337a'. A proximal portion of the coupling member 344' cannot slide over the raised portion 337a', and thus the raised portion 337a' limits distal travel of the coupling member 344' over the pusher member 330'.

Figure 28:
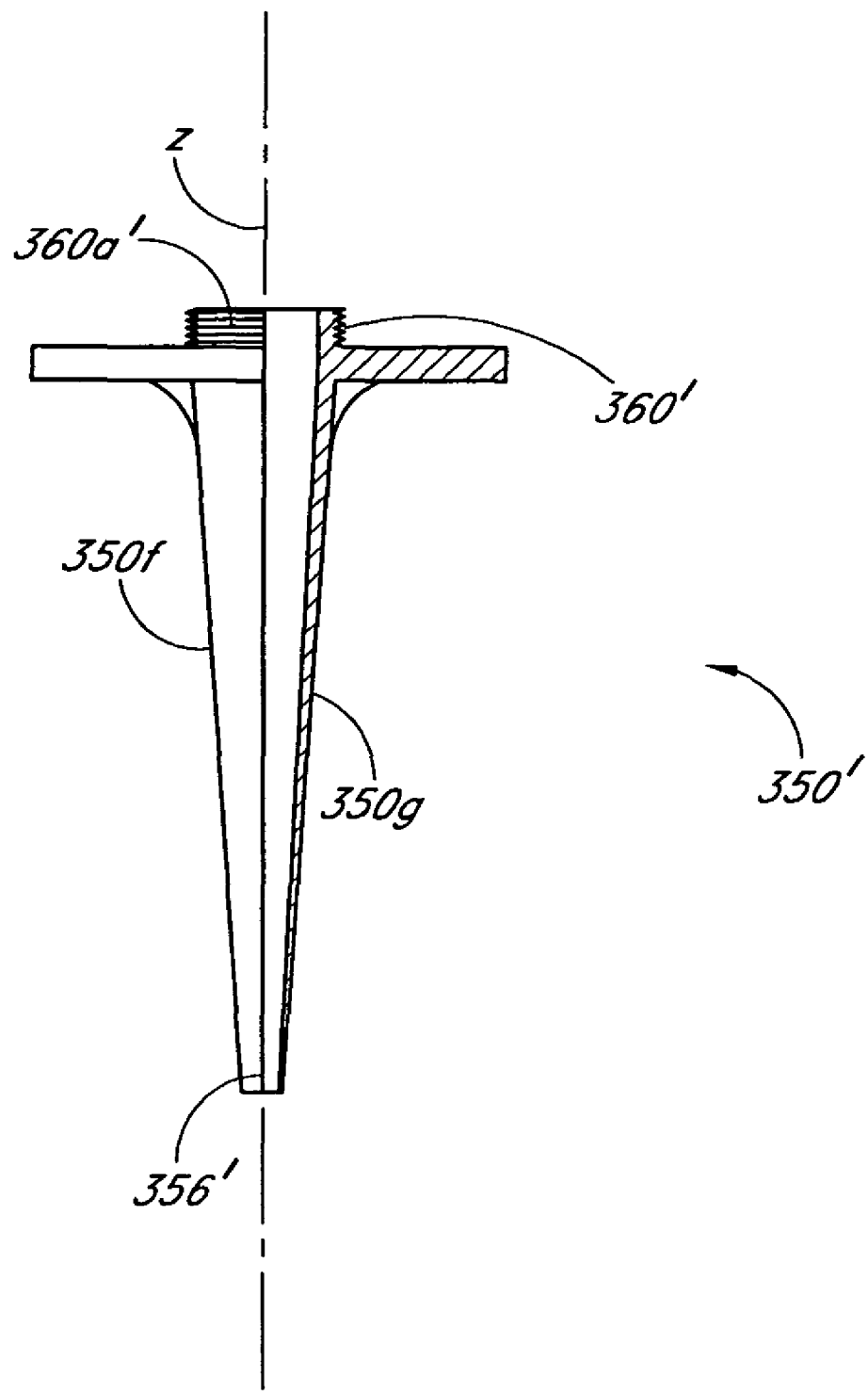
FIG. 28 shows a partially cutaway view of a delivery tube according to the embodiment illustrated in FIG. 25.

With reference to FIGS. 25 and 28, the delivery tube 350' preferably comprises a coupling portion 360' at its proximal end 352. The coupling portion 360' preferably includes a threaded outer surface 360a' configured to mechanically engage the coupling member 344'. In one preferred embodiment, the delivery tube 350' comprises weakened portions 356, as previously discussed. In another preferred embodiment, the body 350a' of the delivery tube 350' comprises two separate halves 350f, 350g configured to abut against each other about an axis "z" and be held in a generally fixed position relative to each other when the coupling member 344' is threaded onto the coupling portion 360'. In yet another preferred embodiment, the delivery tube 350' comprises a body 350a' with two halves 350f, 350g joined at the proximal end 352 of the delivery tube 350' by weakened portions 356'. In another embodiment, the two halves are joined by an elastic member which helps hold the halves together before the hemostatic material is deployed.

With reference again to FIG. 25, the vascular closure apparatus 300' preferably is assembled so that the catheter 310', the pusher member 330', and the delivery tube 350' are releasably coupled by the coupling members so as to be fixed relative to each other. For example, the catheter 310' is slidably inserted into the pusher member 330' until the stopper member 316' abuts against the proximal end 332 of the pusher member 330'. The coupling member 320' is then slid over the stopper member 316' and threaded onto the proximal coupling member 342 of the pusher member 330'. The delivery tube 350' is similarly slid over the catheter 310' and pusher member 330' until the proximal end 352 of the delivery tube 350' abuts against the transition portion 337', wherein the delivery tube 350' preferably encloses the hemostatic material 270 therein. The coupling member 344' is then slid over the raised portion 337a' and threadably engages the coupling portion 360'.

As previously discussed, once the device is in place adjacent the wound "w", the coupling members 344', 320' are disengaged so that the pusher member 330' is uncoupled from the catheter 310' and the delivery tube 350'. The user advances the pusher member 330' into the delivery tube 350' to deform the tube and engage and advance the hemostatic material 270 adjacent the wound "w".

In the embodiments just discussed, the delivery tube is configured to break when the pusher member is advanced. In other embodiments, the delivery tube may not break, but deforms sufficiently so that material within the tube can be dispatched therefrom. For example, at least a portion of the tube may be formed of an elastic material, such as silicone, so that the pusher member deforms the tube and forces material out of the tube and adjacent the wound. Additionally, in one embodiment wherein the tube is formed of an elastic material, the tube does not necessarily include a weakened portion. This principle can also be employed in connection with other embodiments discussed herein, including the following embodiments.

FIGS. 29-37 illustrate another embodiment of a vascular closure apparatus 300" having many aspects similar to the embodiments described above with reference to FIGS. 17-23 and to FIGS. 25-29. Where possible, the same reference numerals are used to identify similar elements, but elements of the present embodiment include the appellation "''". Of course, it is to be understood that similar elements do not necessarily share identical structure.

Figure 29:
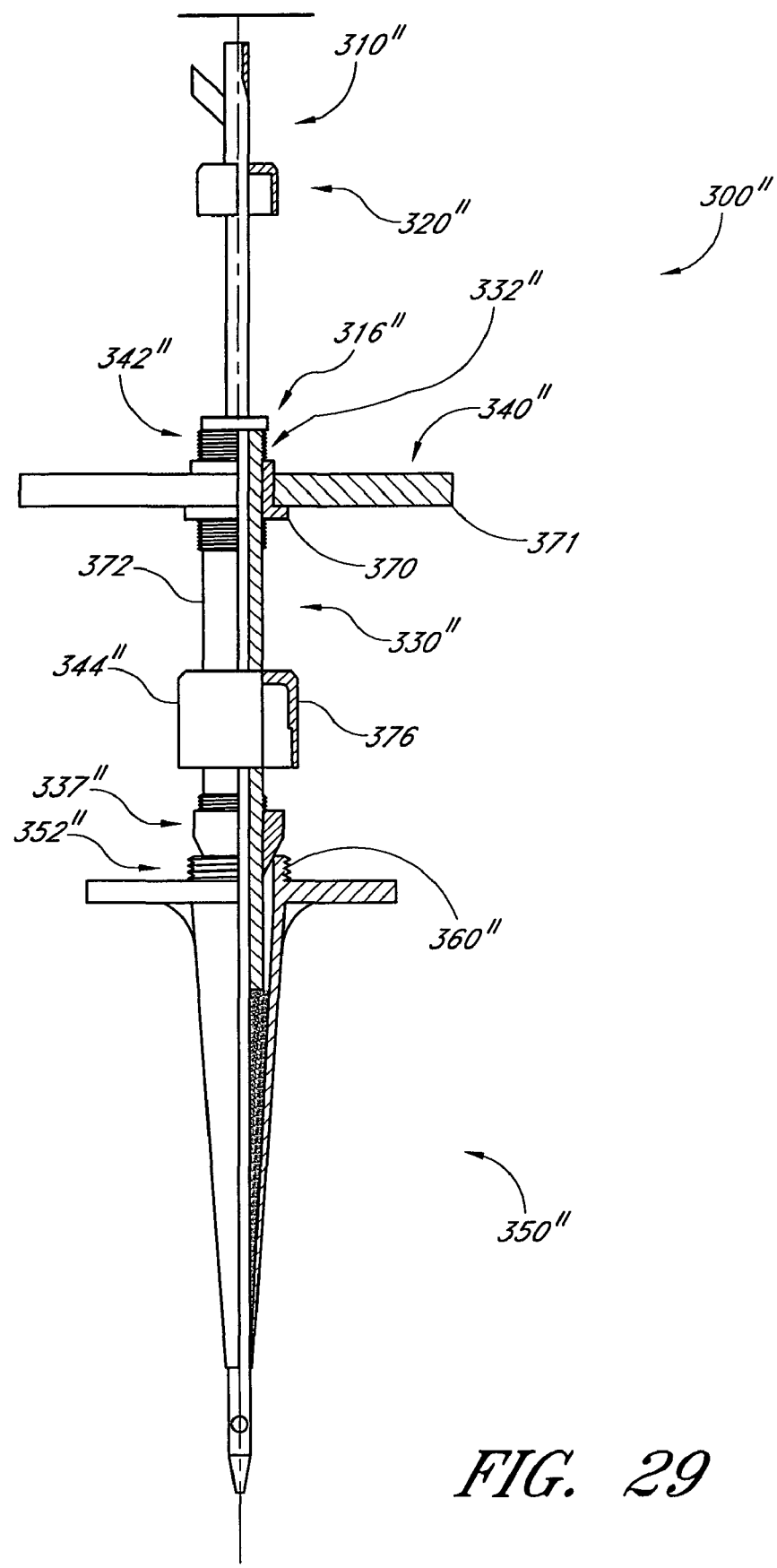
FIG. 29 shows another embodiment of a vascular wound closure apparatus.

With specific reference to FIG. 29, the closure apparatus 300" preferably comprises a catheter 310", a pusher member 330", and a delivery tube 350" releasably connected to each other.

Figure 30:
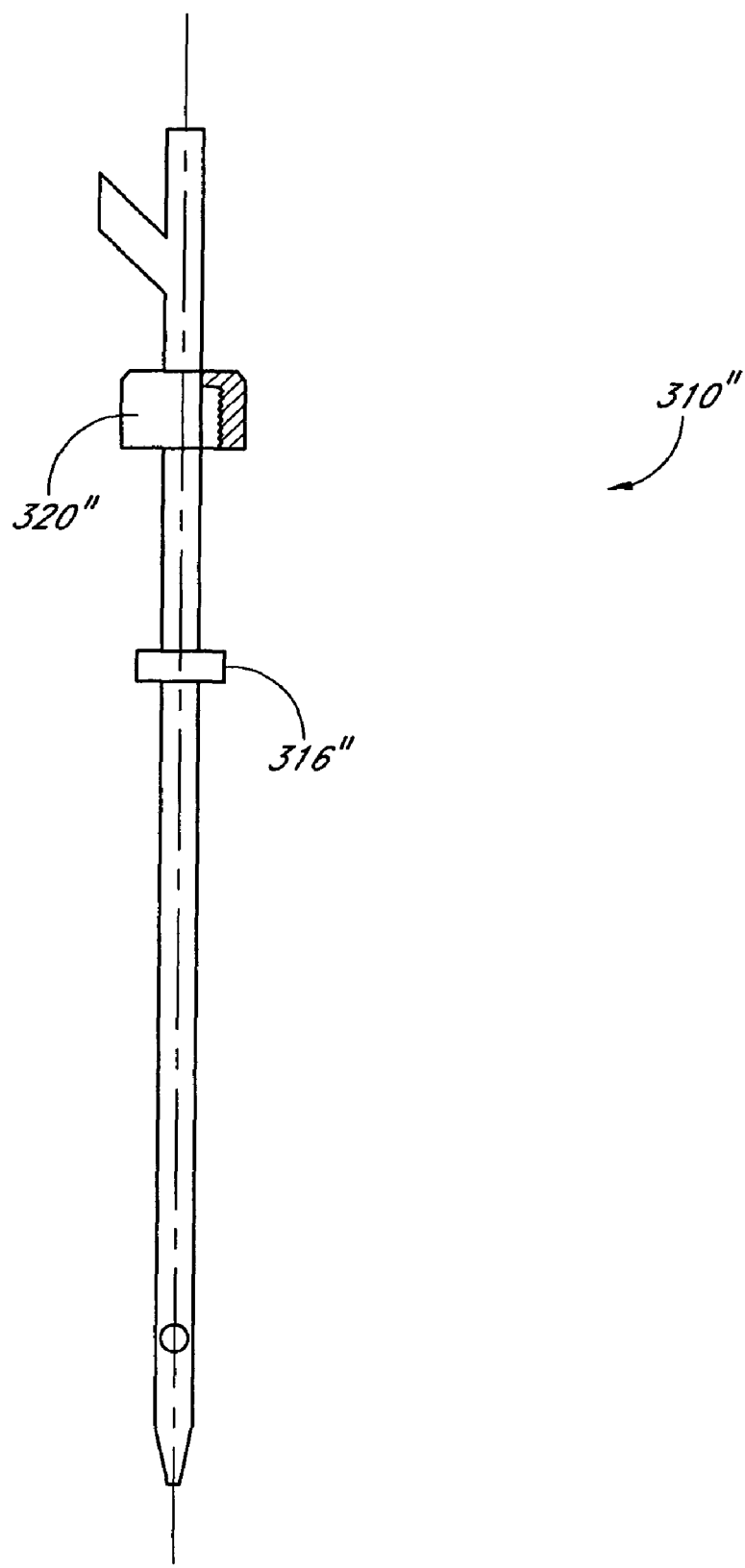
FIG. 30 shows a partially cutaway side view of a catheter according to the embodiment illustrated in FIG. 29.

With reference also to FIG. 30, the catheter 310" preferably comprises an unthreaded stop member 316" that is raised relative to the catheter body. Additionally, a coupling member 320" preferably is configured so that a portion of the coupling member is slidable over the stop member 316" so as to enclose it. However, a proximal portion of the coupling member 320" cannot slide over the stop member 316", and thus the stop member limits the distal travel of the coupling member 320".

Figure 31:
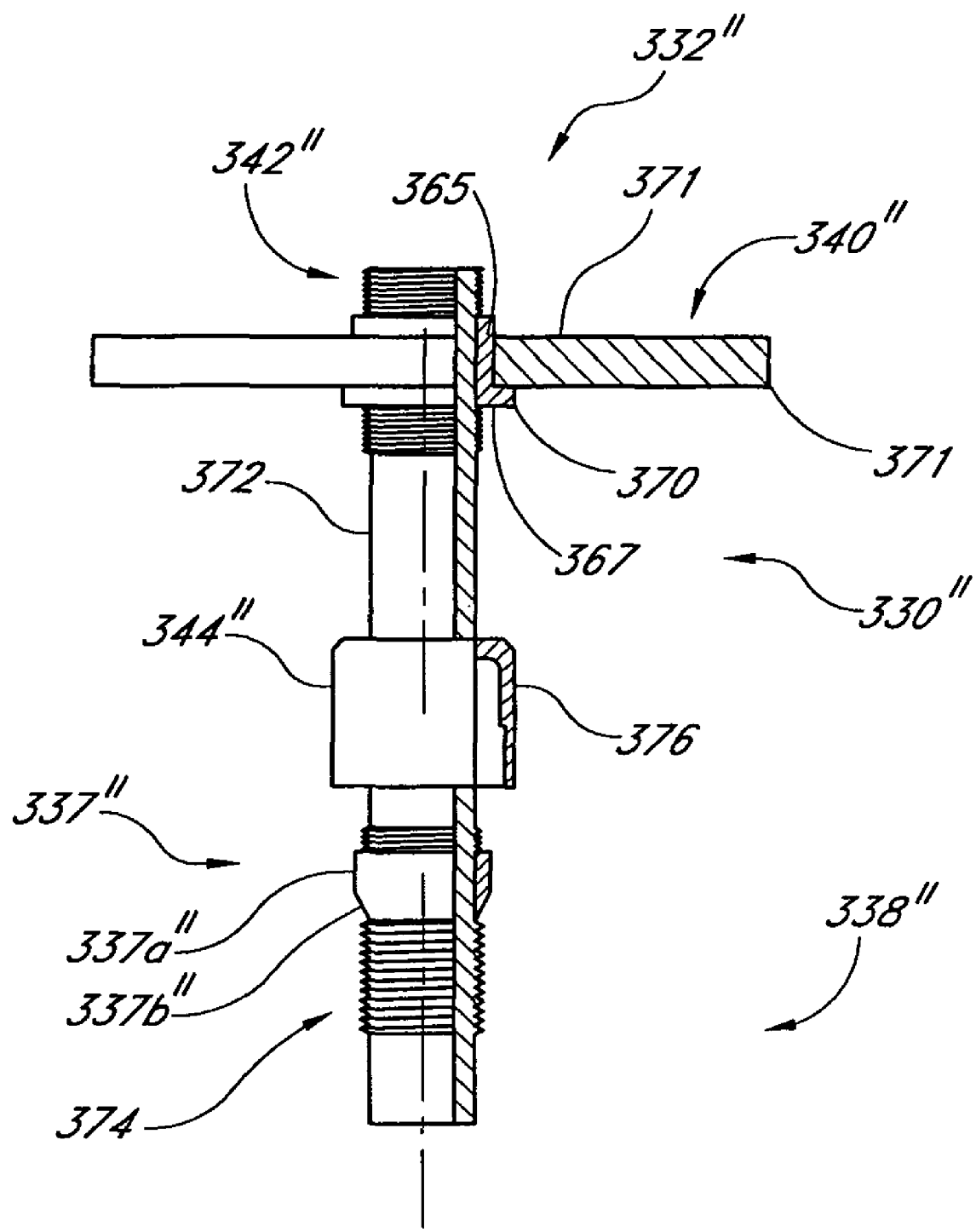
FIG. 31 shows a partially cutaway cross-sectional view of a pusher member according to the embodiment illustrated in FIG. 29.

With reference next to FIGS. 29 and 31, the pusher member 330" preferably is elongate and is slidable over the catheter 310". A proximal end 332" of the pusher member 330" is configured to abut against the stop member 316" when the pusher member 330' is slid proximally over the catheter 310". The threaded outer surface of the proximal coupling member 342" of the pusher 330" preferably is configured to mechanically engage the threads of the coupling member 320" when said coupling member 320" is advanced over the proximal end 332" of the pusher member 330". As such, the pusher member 330" is releasably coupled to the catheter 310" with the proximal end 332" abutting the stop member 316".

The threaded outer surface of the proximal coupling member 342" preferably is also configured to mechanically engage a threaded handle 340". With reference also to FIGS. 32a, 32b, and 33, the illustrated handle 340" comprises a handle support 370 and a handle arm 371. The handle support 370 comprises an elongate body 365 and a flange 367. Preferably, the body 365 has a square or rectangular shaped profile that corresponds with a square or rectangular shaped hole 369 defined in the handle arm 371, such that in an engaged configuration, the handle support 370 rotates together with the handle arm 371. The flange 367 also preferably has a square or rectangular profile. The handle arm 371 preferably is slidable relative the handle support body 365 in an axial direction, and thus preferably can be removed from the handle support 370 and passed over the stop member 316" of the catheter when the coupling member 320" is uncoupled from the proximal coupling member 342". It is to be understood that, in other embodiments, any suitable mechanism, such as a detent, can be used to releasably couple the arm handle 371 to the support 370.

The pusher member 330" preferably comprises a central shaft section 372 that is unthreaded and has a reduced diameter relative the threaded outer surface of the proximal coupling member 342". The central shaft section 372 preferably is located between the proximal coupling member 342", having a raised threaded outer surface, and a distal coupling member 374, also having a raised threaded outer surface.

With continued reference to FIGS. 29 and 31, the pusher member 330" preferably comprises an adjustable stopper 337" adjacent the distal portion 338". The adjustable stopper 337" preferably comprises a cylindrical raised portion 337a" and a generally conical portion 337b". The raised portion 337a" comprises an unthreaded outer surface and a threaded inner surface. The threaded outer surface of the distal coupling member 374 of the pusher member 330" preferably is configured to mechanically engage the threads of the adjustable stopper 337" when the adjustable stopper 337" is advanced over a distal portion 338" of the pusher member 330".

A coupling member 344" is slidably disposed about the pusher member 330". The raised portion 337a" of the adjustable stopper 337" preferably is configured to slidably receive a distal portion of the coupling member 344" about and over its outer surface so that the coupling member 344" encloses the raised portion 337a". However, a proximal portion of the coupling member 344" cannot slide over the raised portion 337a", and thus the raised portion 337a" limits distal travel of the coupling member 344" over the pusher member 330".

With reference next to FIG. 34, the proximal portion of the coupling member 344" preferably defines a hole 368 that is sized and configured such that the coupling member 344" cannot slide distally over the adjustable stopper 337", but can slide proximally over the central shaft section 372, the handle support 370, and the catheter stop member 316". In the illustrated embodiment, the hole 368 is generally complementary to the handle support flange 367. Thus, when the coupling member 320" and the handle 371 have been removed, the coupling member 344" can also be removed if desired. The handle arms 371 can be replaced on the handle support 370 after the coupling member 344" has been removed.

The distal portion of the coupling member 344" preferably comprises a threaded portion 376 on an inner surface. The threaded portion 376 preferably comprises threads covering a proximal portion of the inner surface of the coupling member 344". Preferably, a distal portion of the inner surface of the coupling member 344" is not threaded.

Figure 35:
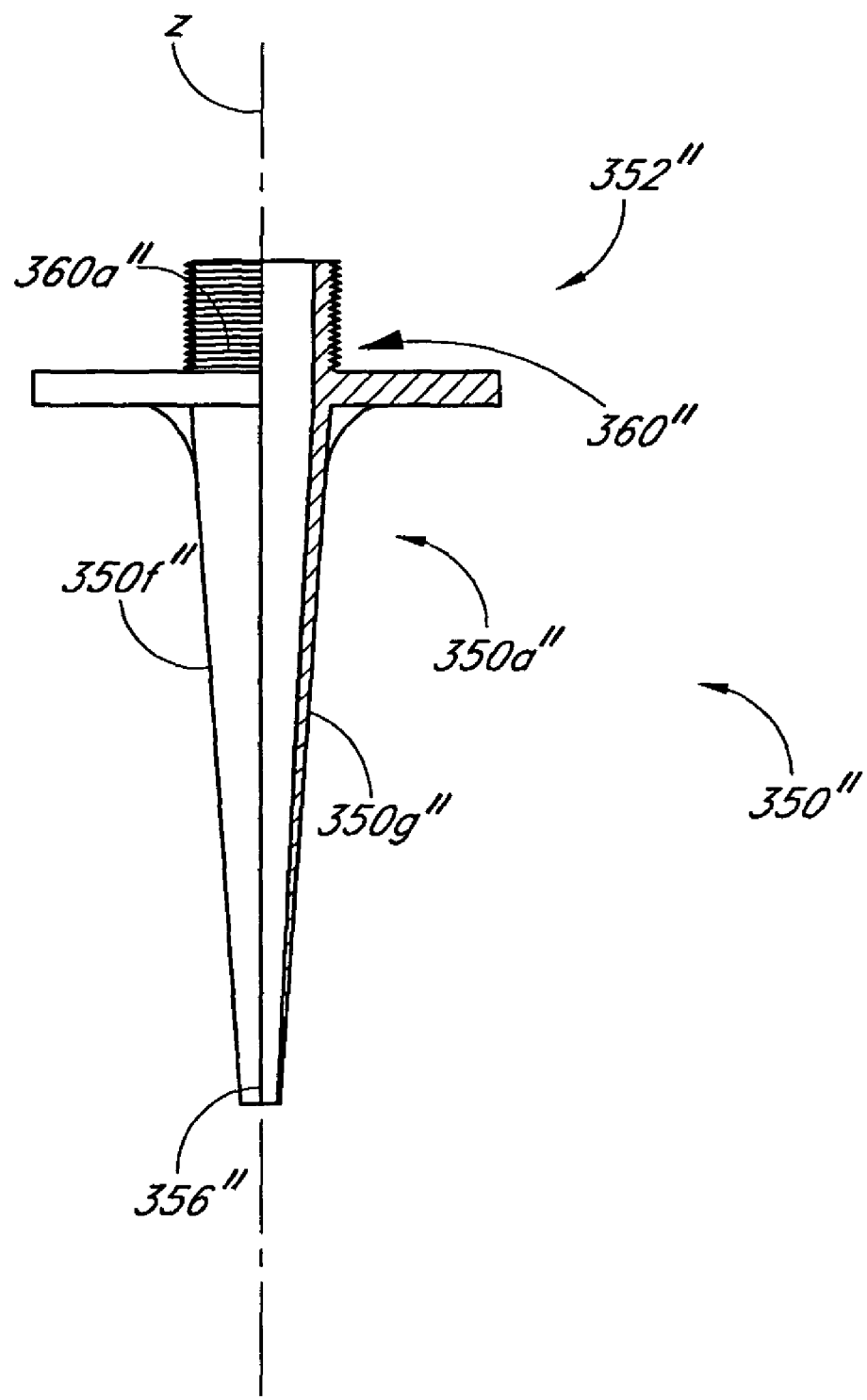
FIG. 35 shows a partially cutaway view of a delivery tube according to the embodiment illustrated in FIG. 29.
Figure 36:
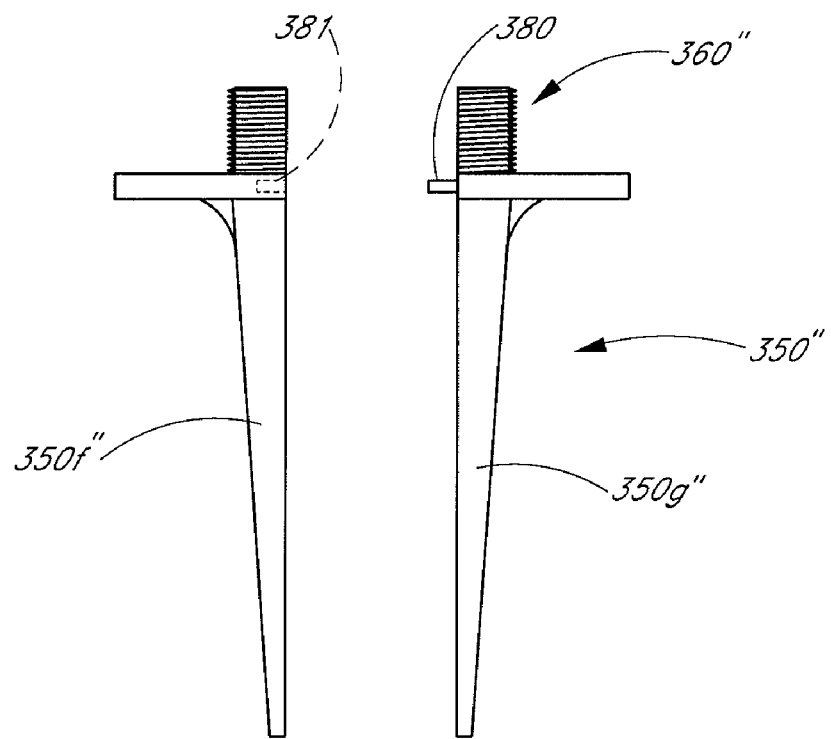
FIG. 36 shows the delivery tube of FIG. 35 separated into two halves.

With reference next to FIGS. 29 and 35-36, the delivery tube 350" comprises a body 350a" made up of two separate halves or segments 350f", 350g". The segments 350f", 350g" are formed separately but are configured to abut against one another about an axis "z" to form the delivery tube 350". Preferably a first segment 350g" has guide portions 380 that are configured to fit into recesses 381 formed in a second segment 350f" in order to properly align the segments to form the delivery tube 350".

Each segment 350f", 350g" has a generally concave inner surface configured so that the tube 350", when assembled, fits concentrically about the catheter 310". In the illustrated embodiment, the inner surface defines a chamber between the catheter 310" and inner surface when the tube 350" is in place. Preferably, at least a distal portion of the chamber is tapered so that the diameter of the chamber decreases smoothly toward the distal end thereof.

Figure 37:
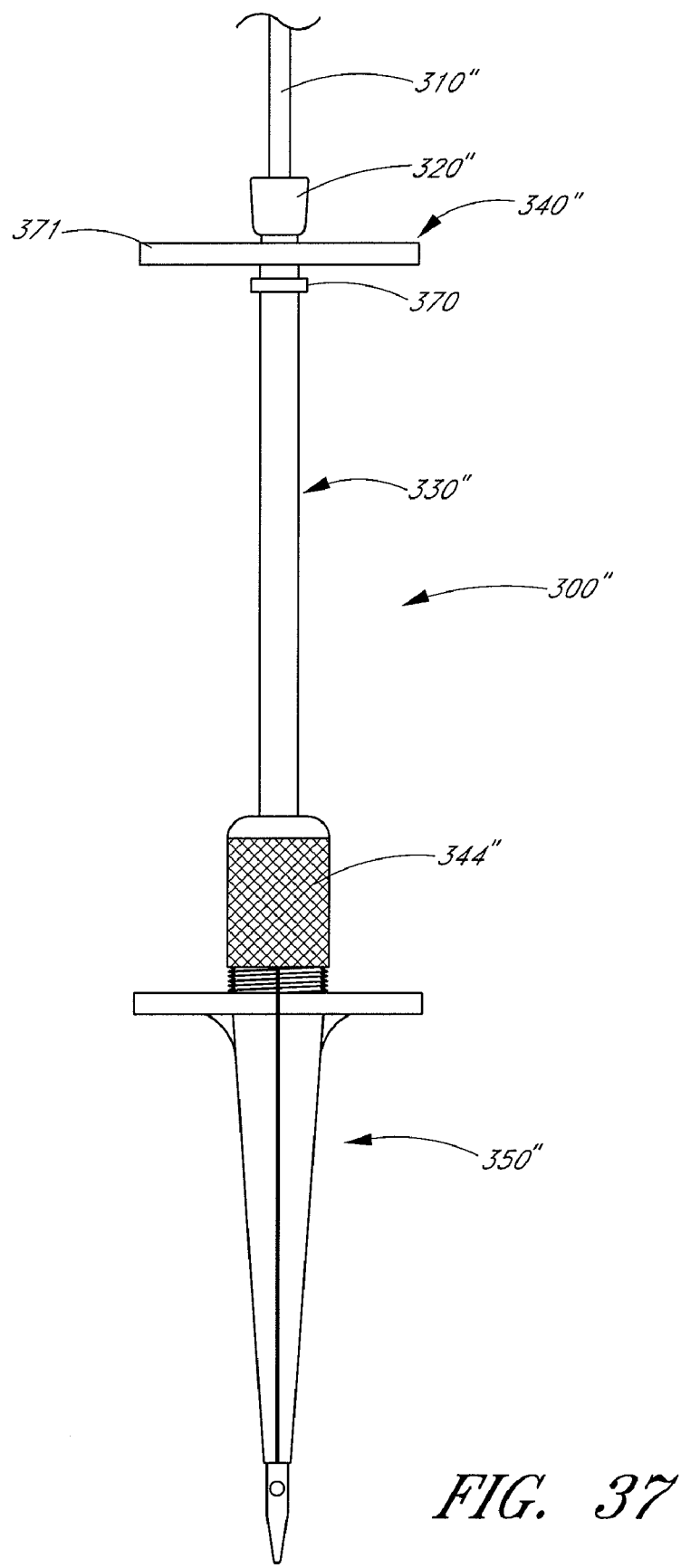
FIG. 37 is a side view of a fully-assembled vascular wound closure device having features in accordance with the embodiment illustrated in FIG. 29.

The delivery tube 350" has a coupling portion 360" at its proximal end 352". The coupling portion 360" preferably includes a threaded outer surface 360a" configured to mechanically engage the coupling member 344". When the coupling member 344" is threaded onto the coupling portion 360", as shown in FIG. 37, the segments 350f", 350g" are held in a generally fixed position relative to each other. It is to be understood that other structures may be used to releasably couple the segments 350f", 350g". Also, in other embodiments, the delivery tube 350" may comprise a body 350a" having several releasably coupled segments at or near the proximal end 352" of the delivery tube 350".

With reference again to FIG. 29, the adjustable stopper 337" preferably contacts an upper portion of the assembled delivery tube 350". The adjustable stopper 337" can be advanced proximally or distally relative the pusher member 330" by rotating the adjustable stopper 337". When the catheter 310", the pusher member 330" and the delivery tube 350" are to be coupled together, moving the adjustable stopper 337" proximally or distally relative the pusher member 330" prior to coupling the pusher member 330" with the delivery tube 350" effectively adjusts the position of the delivery tube 350" relative the catheter 310". Accordingly, another feature of this embodiment is that the position of the distal end of the delivery tube 350" can be adjusted relative the holes in the catheter 310" by movement of the adjustable stopper 337". This may be desirable to adjust the delivery tube 350" position relative the holes in the catheter 310" based on the thickness of a particular blood vessel wall and/or the preference of a clinician. For example, a clinician may adjust the stopper 337" so as to position the distal end of the delivery tube 350" at a desired position between about 1 mm and 1 cm proximal of the holes of the catheter 310".

The threaded inner surface 376 of the coupling member 344" preferably is configured to mechanically engage the threads of the coupling portion 360" when the coupling member 344" is advanced over the stopper 337" and further over a proximal end 352" of the delivery tube 350". Accordingly, another feature of this embodiment is that the delivery tube 350" is securely coupled with the pusher member 330" through the coupling member 344". The coupling member 344" also helps hold the body segments 350f", 350g" together. Because only a portion of the inner surface of the coupling member 344" is threaded, the pusher member 330" and the delivery tube 350" can be quickly and easily decoupled.

Figure 38:
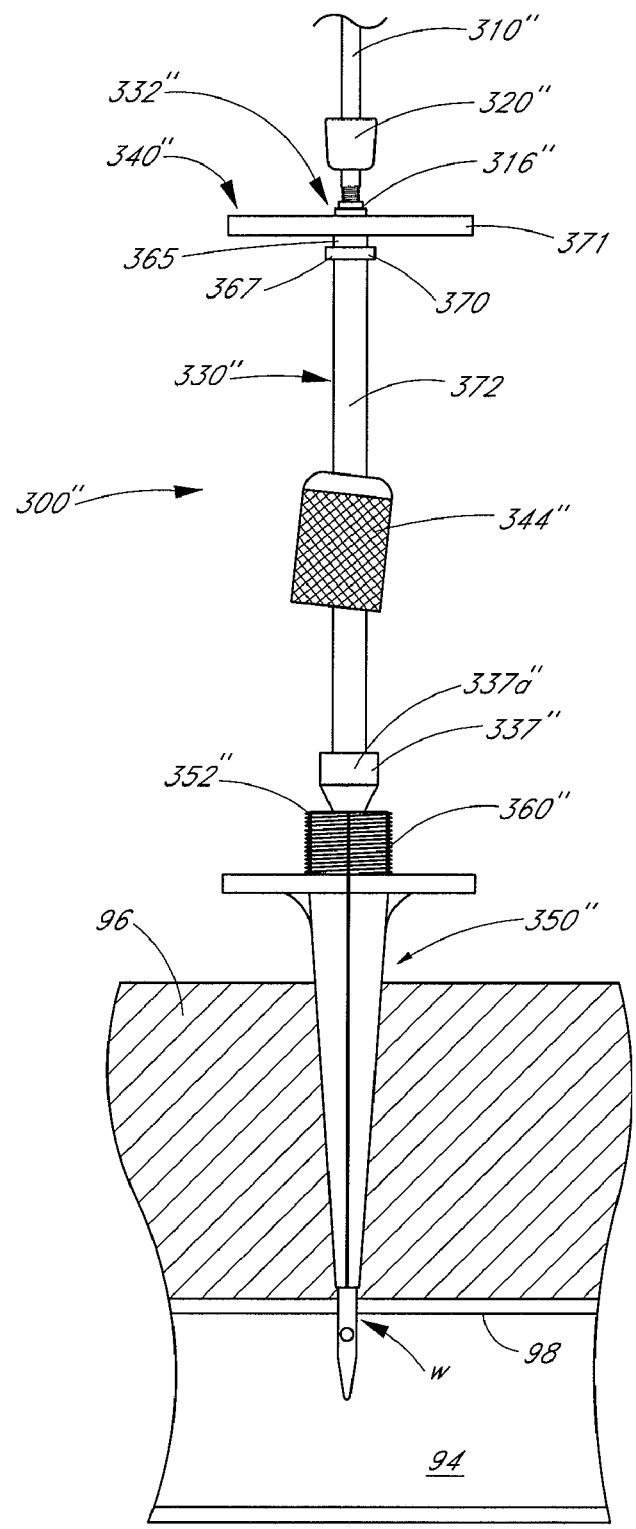
FIG. 38 shows the apparatus of FIG. 37 with the catheter, pusher member and delivery tube uncoupled from one another.
Figure 39:
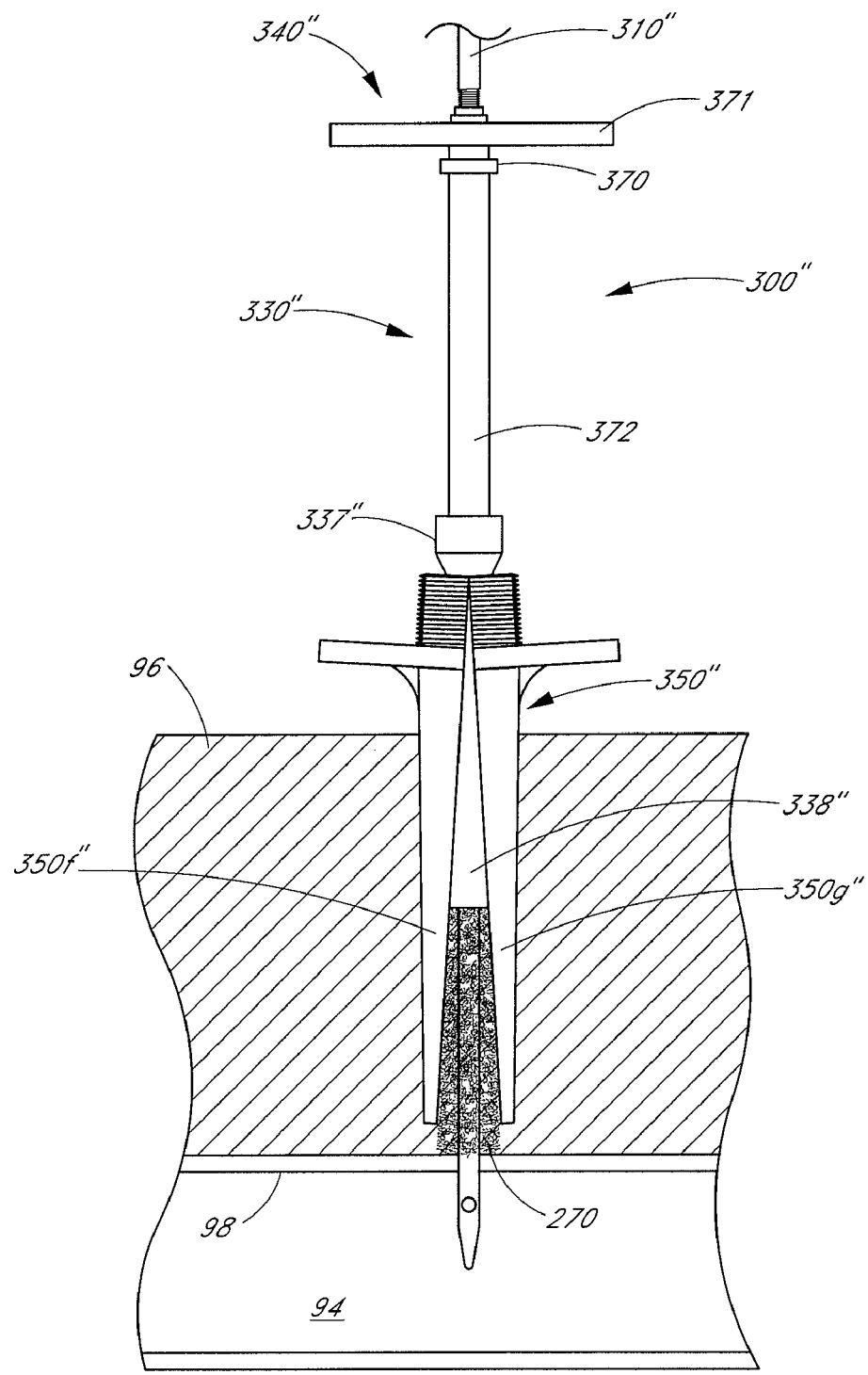
FIG. 39 shows the apparatus of FIG. 37 deploying a hemostatic agent.

With reference next to FIGS. 37-39, the vascular closure apparatus 300" preferably is assembled so that the catheter 310", the pusher member 330", and the delivery tube 350" are releasably coupled by the coupling members so as to be fixed relative to each other. For example, the catheter 310' is slidably inserted into the pusher member 330" until the stopper member 316" abuts against the proximal end 332" of the pusher member 330". The coupling member 320" is then slid over the stopper member 316" and threaded onto the proximal coupling member 342" of the pusher member 330". The hemostatic material 270 preferably is wrapped about the catheter 310" adjacent a distal end of the pusher member 330", and the delivery tube 350" is positioned over the catheter 310" so that the hemostatic material is enclosed within the chamber. The delivery tube 350" is positioned over part of the catheter 310" and pusher member 330" so that the proximal end 352" of the delivery tube 350" abuts against the adjustable stopper 337". The coupling member 344" is then slid over the raised portion 337a" and threadably engages the coupling portion 360". Before coupling the pusher and tube, the clinician may adjust the position of the tube relative to the catheter by advancing or retracting the adjustable stopper 337". Preferably, the delivery tube 350" is arranged on the catheter 310" so that the distal end of the tube 350" is between about 1 mm to 1 cm proximal of the catheter holes.

As previously discussed, once the fully assembled device is in place adjacent the wound "w", the coupling members 344", 320" are disengaged so that the pusher member 330" is uncoupled from the catheter 310" and the delivery tube 350", as shown in FIG. 38. The handle 340" preferably is removed momentarily so that the coupling member 344" can be removed over the handle support 370. The handle 340" preferably is replaced and the adjustable stopper 337' preferably is moved proximally to the central shaft section 372 so that it can slide freely and will not restrict advancement of the pusher member 330" relative the delivery tube 350".

As best shown in FIG. 39, as the clinician advances the pusher member 330" into the delivery tube 350", the distal end of the pusher member 330" engages the hemostatic material 270 and advances toward the wound "w". As the user advances the pusher member 330" into the delivery tube 350", a distal portion 338" of the pusher member 330" preferably contacts the tapered inside surface of the delivery tube chamber, thus at least partially separating the segments 350f', 350g' of the delivery tube 350". This allows the hemostatic material 270 to be deployed from the chamber and onto the blood vessel at or adjacent the wound.

The distal portion 338" of the pusher member 330" preferably contacts the inside surface of the delivery tube 350" in a distal portion of the tube. For example, in one embodiment, the pusher member 330" first engages the tapered inner surface at a point distal the halfway point of the length of the tube. In another embodiment, the first engagement point is between about ⅔ and ¾ of the way into the delivery tube 350".

In accordance with one embodiment, preferably the apparatus is configured so that the stopper 337" is advanced over just one or a few threads of the pusher member distal coupling member 374 when the apparatus is assembled. As such, to deploy the hemostatic material 270, rather than first retracting the stopper 337", the clinician may simply twist the handle to advance the pusher relative to the stopper 337". Soon the stopper 337" will become unthreaded from the coupling member 374 and will slide freely over the central shaft section 372, allowing the clinician to quickly and easily advance the pusher member 330".

In the embodiments just discussed, the delivery tube segments 350f', 350g" are configured to separate when the pusher member 330" is advanced. In some embodiments, the delivery tube segments may completely separate, while in other embodiments, only portions of the delivery tube 350" may separate. Preferably, at least the distal portions of the tube separate. The segments preferably are configured such that advancement of the pusher member 330" engages the delivery tube 350" so that material within the tube can be dispatched therefrom.

With reference to FIGS. 40, 41 and 42a-b, a vascular wound closure assembly 430 includes an elongate catheter 432 having a distal end 434 and a proximal end 436. A distal opening 438 is formed through the distal end 434 of the catheter 432 and opens along a longitudinal axis of the catheter 432. The catheter 432 includes a tapered tip 4440 at the distal end 434. An elongate main body 42 of the catheter 432 is disposed proximal the tapered tip 4440. Preferably the main body 42 has a substantially uniform diameter along its length. A lumen 444 extends longitudinally within the catheter 432 from the distal opening 438 to the proximal end 436.

A connector portion 446 is provided on the proximal end 436. The connector portion 446 includes a main lumen 448 and a secondary lumen 450. The main lumen 448 extends along the longitudinal axis of the catheter 432 and is coextensive with the catheter lumen 444. The secondary lumen 450 extends outwardly from the main lumen 448, but communicates with the main lumen 448 and the catheter lumen 444. A proximal opening 452 is provided at the proximal end of the main lumen 448 and, like the distal opening 438, opens along the longitudinal axis. A secondary opening 454 opens into the secondary lumen 450.

The distal and proximal openings 438, 452 are sized and adapted to accommodate a guidewire 458 such as the guidewire used in angioplasty and other vascular surgeries. As such, the guidewire 458 can be threaded through the catheter 432 and the catheter can be advanced over the guidewire 458.

A hole 460 is formed through a side-wall of the catheter 432 near the distal end of the catheter. In another embodiment, at least two holes are provided. All of the holes preferably are disposed substantially the same distance from the distal end of the catheter.

With continued reference to FIGS. 40, 41 and 42a-b, a vacuum or other source of suction 464 is provided and communicates, through tubing 466, with the secondary lumen 450 of the catheter connector portion 446. Thus, a vacuum is drawn through the catheter lumen 44. Preferably, the distal and proximal openings 438, 452, which accommodate the guidewire 458, are sized so that the guidewire 458 substantially plugs the openings; thus, the vacuum is drawn through the hole 460. A viewing port 468 is arranged between the source of suction 464 and the catheter 432. The viewing port 468 is configured to allow a clinician to view the material that is drawn by suction through the hole and through the catheter lumen 44.

A delivery tube 490 is disposed over the catheter 432 proximal of the hole 460. A pusher member 500 also is disposed over the catheter 432 generally proximal of the delivery tube 490. The delivery tube 490 and pusher member 500 will be discussed in more detail below. The delivery tube 490 and pusher member 500 preferably are selectively secured to the catheter 432 so that they are in a fixed position relative to the catheter. More specifically, the delivery tube 490 preferably is releasably secured to the catheter 432 so that a distal end 502 of the delivery tube 490 is spaced a distance between about 0.5 to 1.5 cm proximal of the hole 460. More preferably, the distal end 502 of the delivery tube 490 is spaced less than about 1 cm from the hole.

Figure 43:
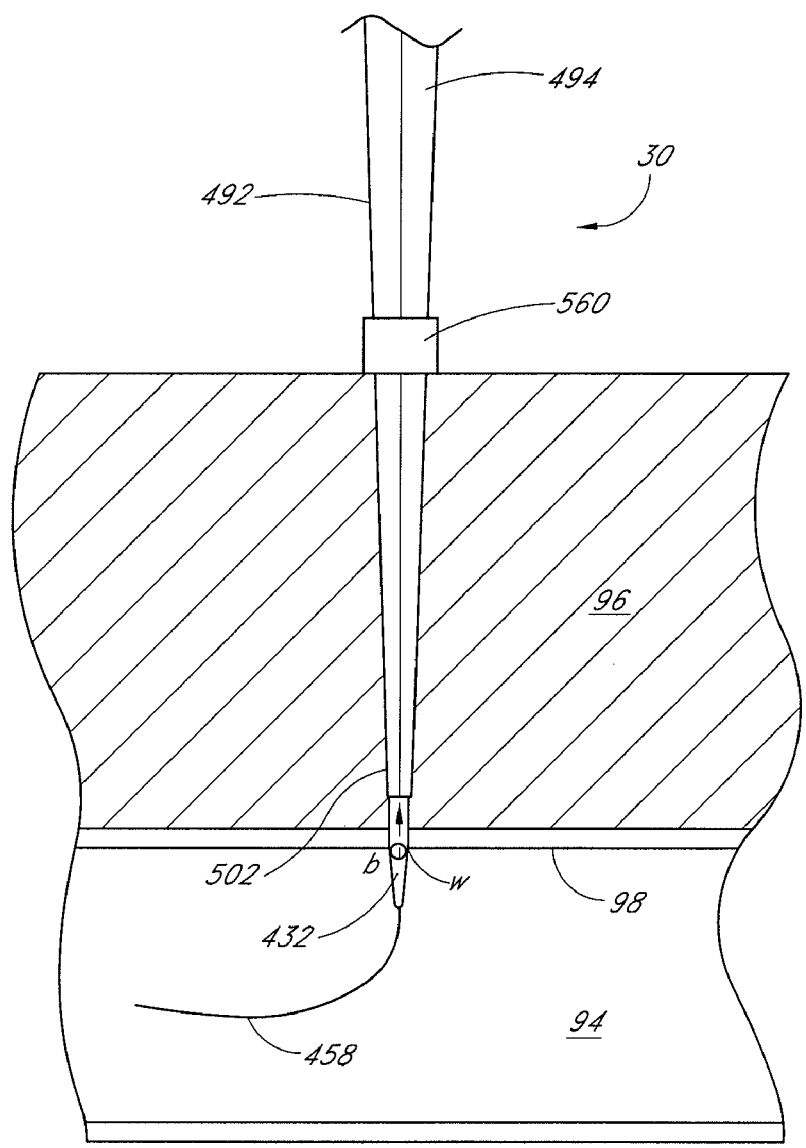
FIG. 43 shows a portion of the apparatus of FIG. 41 in position adjacent a vascular wound.

With reference also to FIG. 43, the illustrated vascular wound closure assembly 430 can be precisely positioned adjacent a subcutaneous vascular wound "w" in order to close the wound. With reference to FIGS. 40-43 and 50, in order to precisely locate and provide access to a femoral artery puncture wound w, the catheter 432 is first threaded over the guidewire 458, which has been previously inserted into the patient's femoral artery 94 through the puncture wound w. The lumen 444 is attached to the source of suction 464 and the assembly 430 is advanced over the guidewire 458 through a patient's tissue 96 so that the distal tip 440 of the catheter 432 extends through the vascular puncture wound w.

As the assembly 430 is advanced, the source of suction 464 draws bodily fluids through the hole 460. The fluids pass through the viewing port 468, which allows the clinician to identify the fluids being withdrawn. The viewing port 468 can have any suitable structure or location. For example, the viewing port can comprise clear tubing attached to the catheter, a substantially transparent syringe that functions as both a source of suction and a viewing port, or a portion of the catheter that is substantially transparent. Most preferably, the catheter 432 is formed of a transparent material so that the clinician becomes aware as soon as blood begins to be drawn through the catheter.

When the hole 460 passes the artery wall 98 and enters the blood vessel 94, as shown in FIG. 43, blood "b" begins to be drawn through the hole 460 into the catheter 432 and is conducted past the viewing port 468. Thus, when blood b is observed in the viewing port 468, the clinician will know that the hole 460 has just passed into the puncture wound w and that the distal end 502 of the delivery tube 490 thus positioned adjacent the outer wall 98 of the artery 94, preferably within about 1 cm of the artery wall 98.

Figure 40:
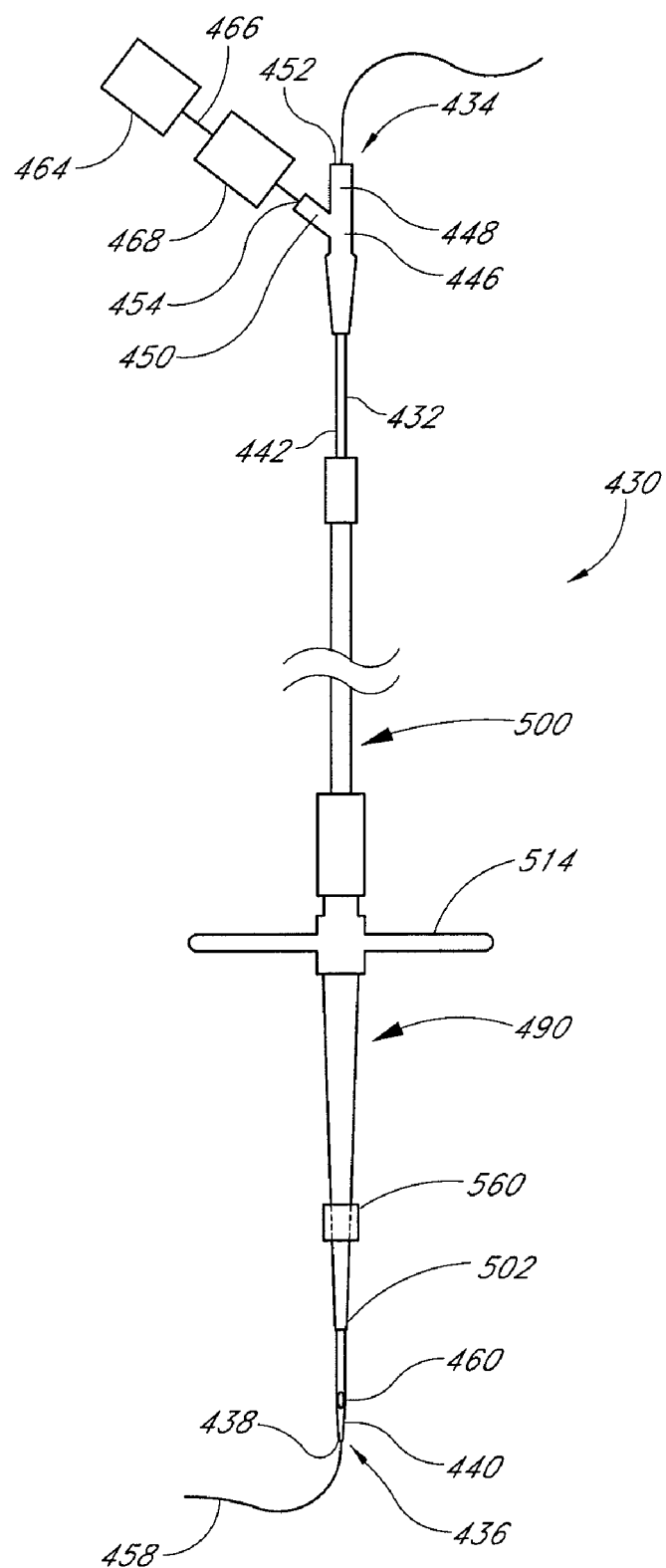
FIG. 40 is a side view of another embodiment of a vascular wound closure apparatus.
Figure 41:
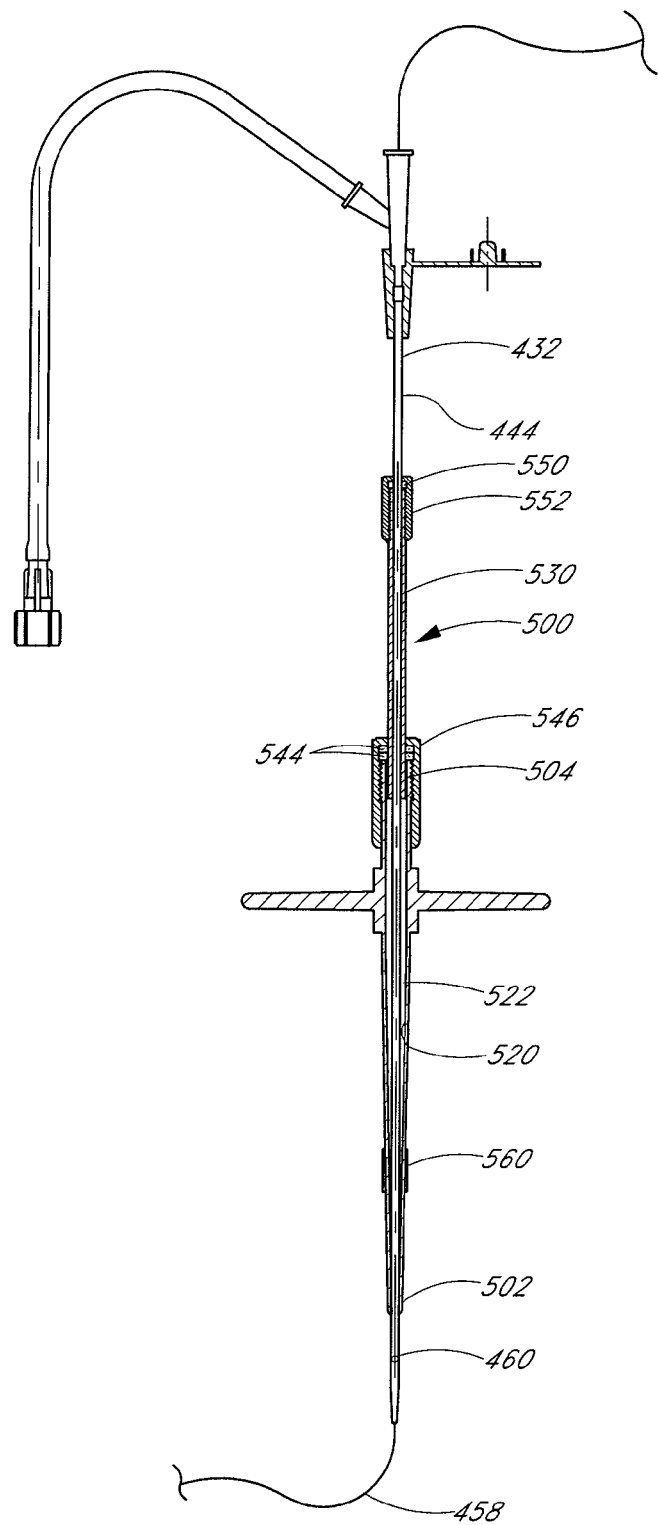
FIG. 41 is a cross sectional view of the apparatus of FIG. 40.
Figure 42A:
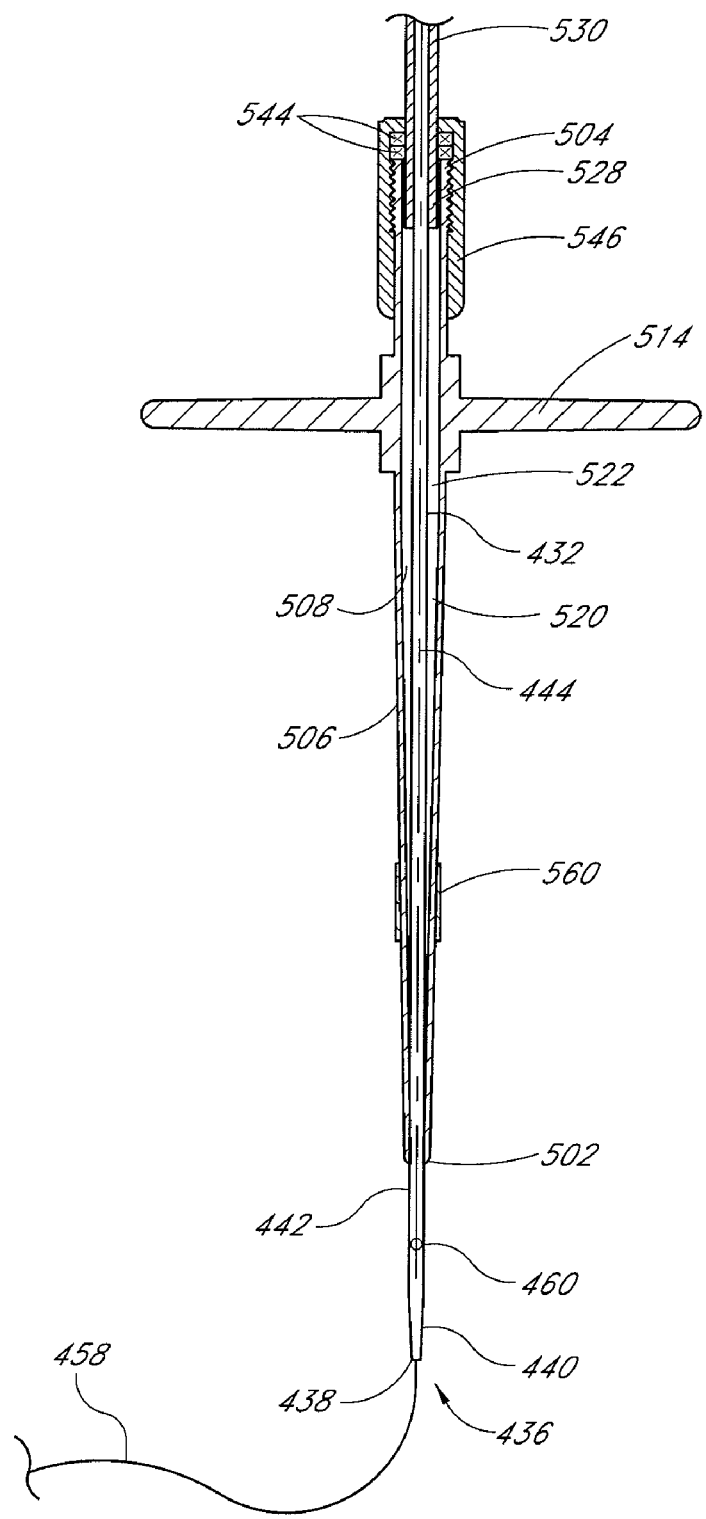
FIG. 42a is a close up view of a portion of the apparatus of FIG. 41.
Figure 42B:
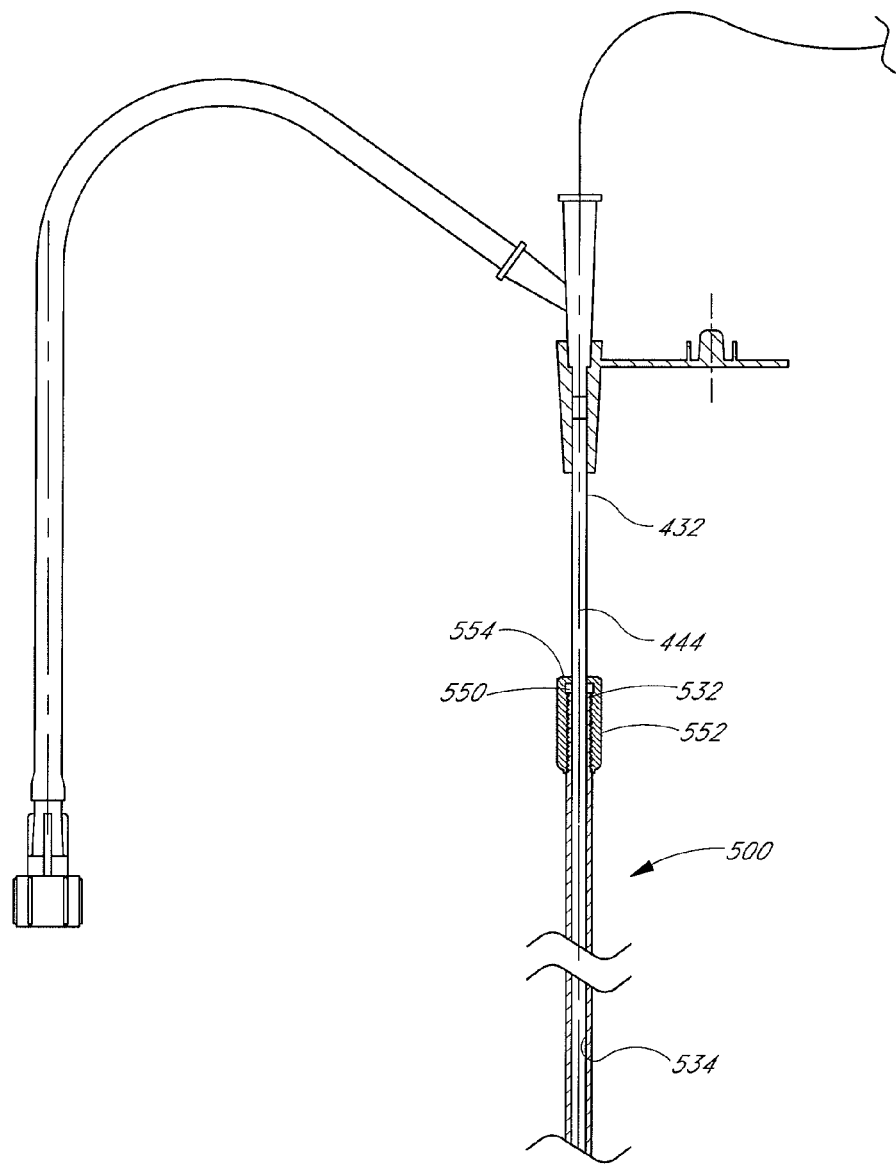
FIG. 42b is a close up view of another portion of the apparatus of FIG. 41.
Figure 44:
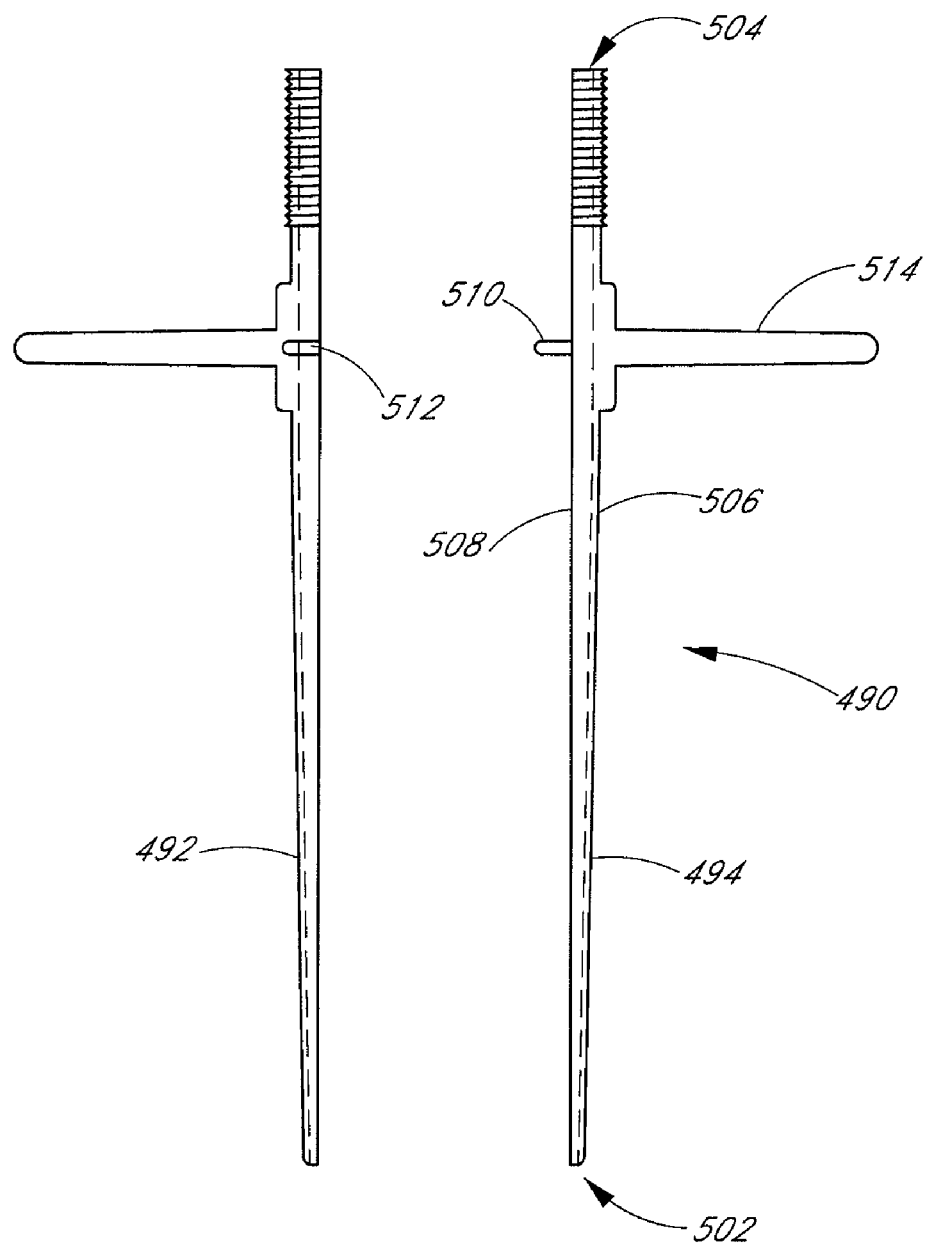
FIG. 44 shows a delivery tube portion of the apparatus of FIG. 41 separated into halves.

With reference next to FIG. 44, the delivery tube 490 is generally elongate and comprises first and second separately-formed members 492, 494 that engage one another to form the delivery tube 490. Each tube member 492, 494 has a distal end 502, a proximal end 504, an outer surface 506 and an inner surface 508. Guide posts 510 formed on one of the tube members 492, 494 fit into guide recesses 512 formed in the other member so as to align the tube members 492, 494. When connected and aligned as shown in FIG. 40, the tube members 492, 494 form the delivery tube 490. As shown, the proximal end 504 of the delivery tube 490 preferably is threaded on its outer surface 506. A handle portion 514 is disposed distal of the proximal end 504, and the delivery tube 490 generally tapers from the handle 514 to the distal end 502.

A chamber 520 is formed within the delivery tube 490, and the catheter 432 extends therethrough. At the distal end 502 of the delivery tube 490, the chamber 520 is just large enough to accommodate the catheter 432. However, as the tube tapers in a proximal direction, a space 522 is defined between the catheter 432 and the inner surface 508 of the tube 490. In the illustrated embodiment, the space 522 is packed with a therapeutic agent, preferably a hemostatic material 270 that can be delivered from the tube 490 subcutaneously and adjacent the vascular wound w. A distal end 528 of the pusher member 500 is accommodated within the proximal end 504 of the delivery tube 490.

In a preferred embodiment, the hemostatic material 270 comprises a hydrophilic fibrous fleece. Throughout this description, the term fleece is used as a broad term in its ordinary sense and refers to, without limitation, in a non-woven or a woven cloth form or in a puff or ball form. It is to be understood that the fibrous fleece may be treated or coated in any suitable manner to enhance its hydrophilic properties and/or its hemostatic properties. In a preferred embodiment, fibrous chitosan fleece is treated to deposit a hemostatic agent thereon. Most preferably, microporous polysaccharide microspheres are deposited on the fleece.

Figure 45:
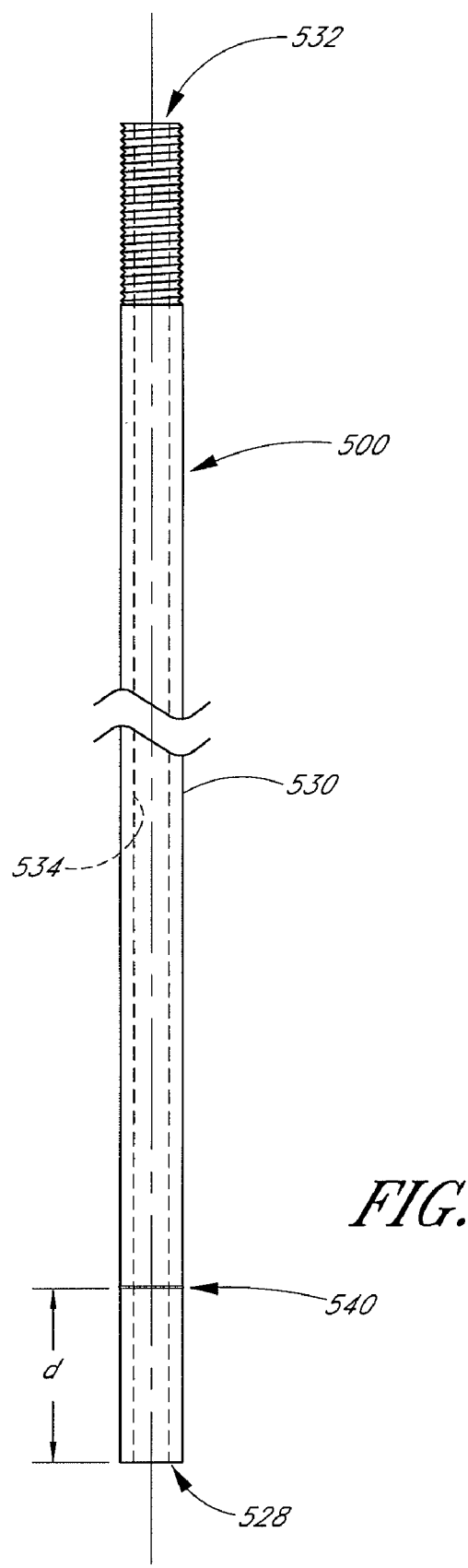
FIG. 45 shows a pusher member of the apparatus of FIG. 41.

With reference next to FIG. 45, the pusher member 500 comprises an elongate body 530 and has distal and proximal ends 528, 532. A lumen 534 is formed longitudinally through the pusher member 500, and preferably is sized to slidably accommodate the catheter 432 therethrough. Preferably, the pusher member 500 is rigid enough so that it can be grasped at or near its proximal end 532 and pushed forward, in turn engaging and pushing the hemostatic material 270 within the delivery tube 490, without binding or bending excessively. The distal portion 528 of the pusher member 500 is configured to fit within a proximal portion 504 of the delivery tube 490. However, the distal portion 528 of the pusher member 500 preferably has a greater diameter than at least a portion of the delivery tube 490 near the distal end 502 of the delivery tube 490. As such, when the pusher member 500 is advanced relative to the delivery tube 490, the pusher member 500 engages the inner surface 508 of the tube members 492, 494 and forces them apart so as to deploy the hemostatic material 270 from within the delivery tube 490.

In the illustrated embodiment, the pusher member 500 is threaded along its proximal end 532. An annular ridge 540 is formed a distance "d" from the distal end 528 of the pusher member 500. The annular ridge 540 projects radially outwardly a very small distance from an outer surface of the pusher member 500. Since the annular ridge 540 projects only a very small distance from the surface of the pusher member 500, it does not interfere with the pusher member's slidability into the proximal end 504 of the delivery tube 490.

In the illustrated embodiment, the pusher member 500 has a diameter of about 4 mm and a lumen diameter 534 of about 2 mm. The annular ring 540 extends outwardly from the outer surface a distance of between about 0.1 mm to 0.25 mm, and, more preferably, about 0.15 mm.

Figure 46:
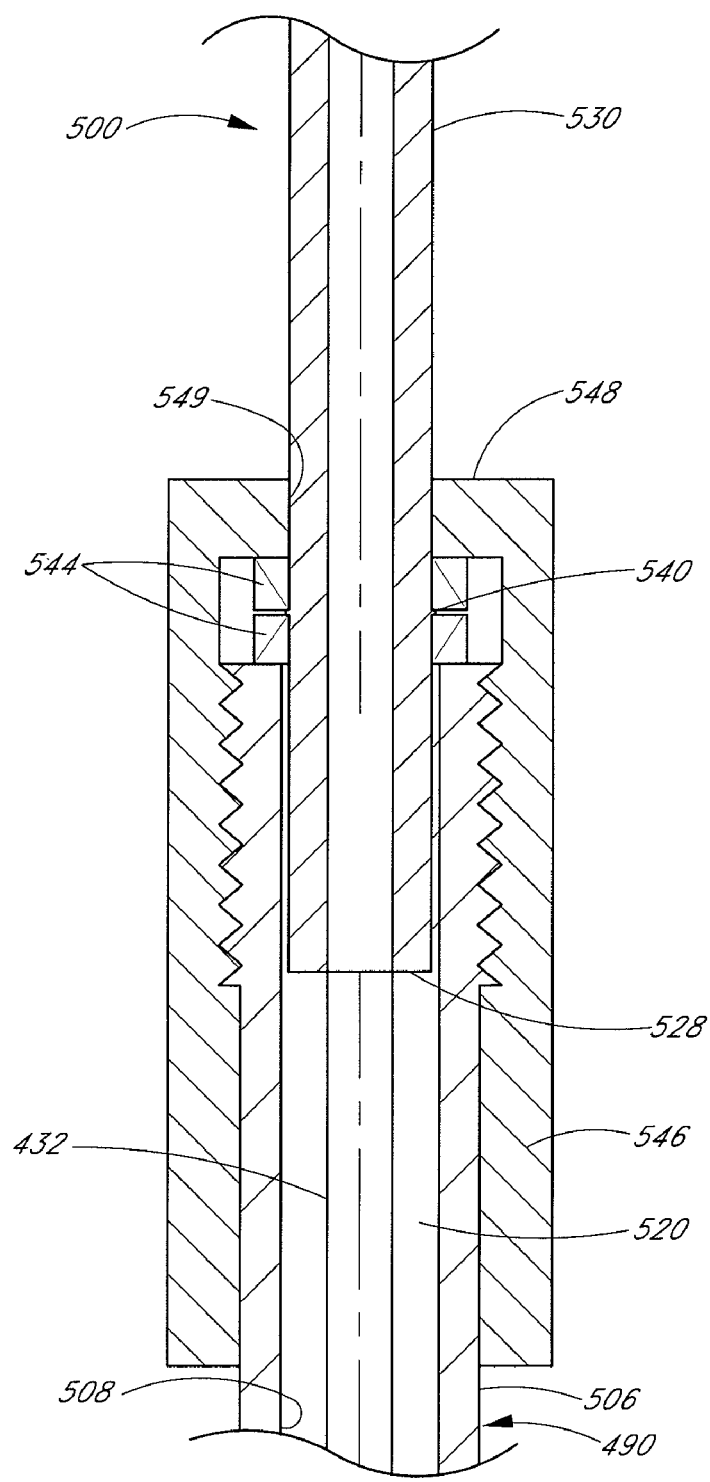
FIG. 46 is a close up view showing a distal end of the pusher member of FIG. 44 fit into a proximal end of the delivery tube of FIG. 44.

With reference also to FIG. 46, which shows a close up view of the distal portion 528 of the pusher member 500 as installed on the delivery tube 490, preferably a pair of elastomeric annular locking members 544 are disposed around the pusher member 500. The locking members 544 preferably are arranged immediately adjacent either side of the annular ridge 540, and are sized so as to engage the proximal end 504 of the delivery tube 490 so as not to slide into or over the delivery tube 490. Preferably, the elastomeric locking members 544 are fit about the pusher members 500 so that they can be slid along the pusher member 500, and even can slide over the annular ridge 540.

An internally threaded locking cap 546 is configured to be threaded onto the proximal end 504 of the delivery tube 490. The locking cap 546 has proximal wall 548 having a hole 549 formed therethrough. The hole 549 is sized to accommodate and slide over the pusher member body 530. As shown, the locking members 544 are arranged on the pusher member body 530 adjacent either side of the annular ridge 540, and the pusher member 500 is inserted into the delivery tube 490 until the locking members 544 engage the proximal end 504 of the delivery tube 490. The cap 546 is then advanced over the pusher member 500 and threaded into place on the delivery tube 490. As the cap 546 is tightened, the proximal wall 548 of the cap 546 engages the locking members 544, which are then compressed longitudinally between the cap proximal wall 548 and delivery tube proximal end 504. Due to their elastomeric properties, as the locking members 544 are compressed longitudinally, they expand laterally, and thus tightly engage the pusher member 500 at and adjacent the annular ridge 540.

In the illustrated embodiment, the locking members 544 tightly engage the annual ridge 540 such that they resist sliding over the ridge. Since a locking member 544 is disposed on each side of the ridge 540, the pusher 500 is thus prevented from sliding in either a proximal or a distal direction relative to the tube 490. However, once the cap 546 is loosened and the locking members 544 are released from compression, the annular ridge 540 is slidable through the locking members 544, and the pusher 500 is correspondingly slidable.

In the illustrated embodiment, the locking cap 546 and delivery tube 490 are threaded. It is to be understood that any other fastening mechanism may be employed, such as for example a J-lock or detent.

The illustrated embodiment employs an annular ridge 540 disposed on the pusher member 500. It is to be understood, however, that other configurations employing a similar principle can be acceptable. For example, any type of protuberance, including a bump, a series of bumps, spikes or any other protuberance that projects from a surface of the pusher member 500 can be employed. Further, protuberances can be employed at only one area disposed a predictable distance from the distal end of the pusher member as shown in the illustrated embodiment, or, in other embodiments, can be disposed at various locations or even continuously along the pusher member so as to allow customization and optimization of the placement and locking position of the pusher member relative to the delivery tube. Further, in other embodiments, rather than a series of bumps or the like, the pusher member surface can be treated to create a surface roughness, such as by being sanded with a low grit sandpaper, or to be pitted. In such an instance, protuberances are considered to extend from the lowest portions of the pits, grooves or the like. When the locking members 544 are longitudinally compressed, the locking members will expand transversely and tightly engage at least portions of the pits and protuberances so as to fix the pusher member 500 in position relative to the delivery tube 490. As such, a protuberance is considered to be any surface aspect upon which a locking member may obtain purchase to grip the pusher member when the cap is tightened.

In the illustrated embodiment, the locking members 544 comprise elastomeric rings. It is to be understood that, in other embodiments, the locking members may be shaped differently, and may extend around only a portion of the pusher member. Further, although the illustrated embodiment shows two locking members 544 disposed one on either side of the annular ridge 540, it is to be understood that other embodiments may employ only a single locking member, or more than two locking members, configured to releasably engage an annular ridge or other protuberance configuration. In still another embodiment, one or more locking members are employed, but no protuberances are formed on the pusher member surface. In this embodiment, the locking members are pushed tightly against the pusher member when the cap is tightened so as to increase the friction between the locking members and the pusher member, and accordingly resist movement of the pusher member relative to the delivery tube.

Figure 47:
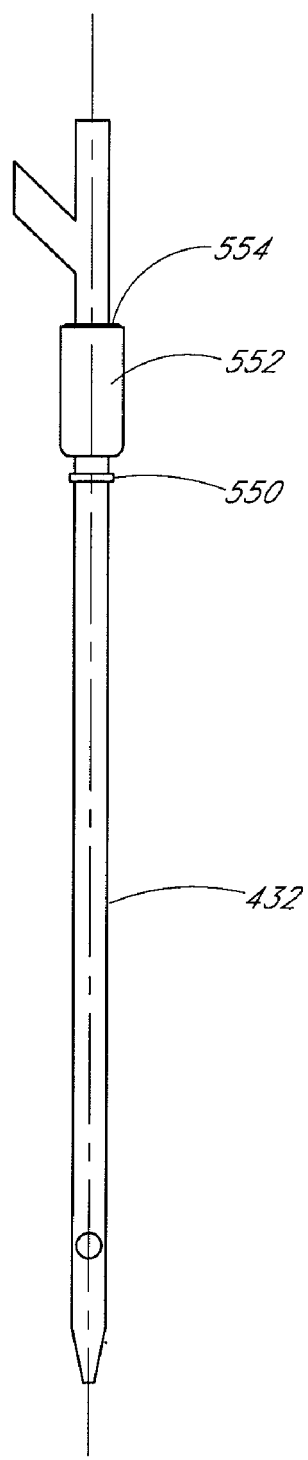
FIG. 47 shows a catheter portion of the apparatus of FIG. 41.
Figures 48, 49:
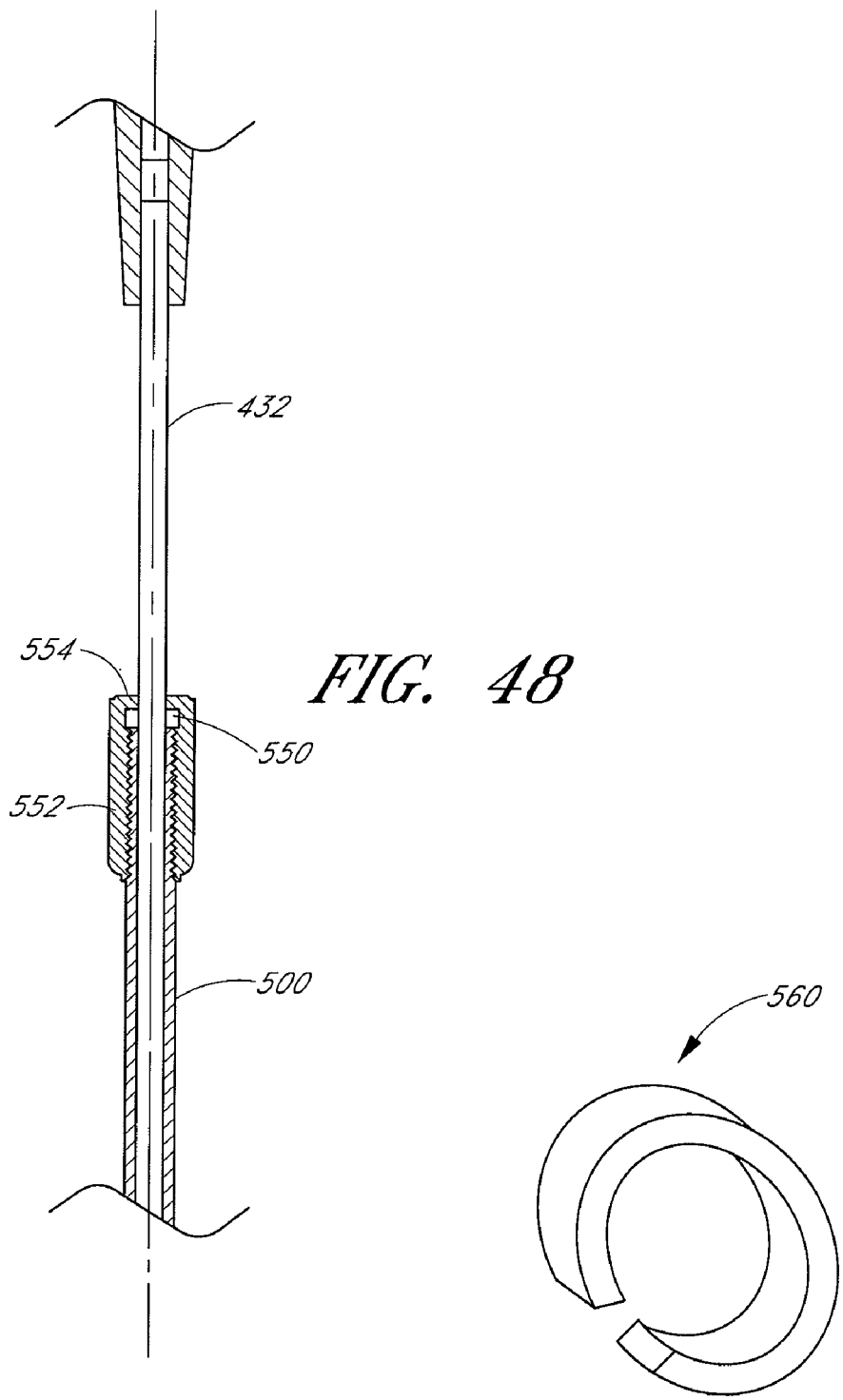
FIG. 48 is a close up view showing the catheter of FIG. 47 attached to a proximal end of the pusher member of FIG. 45.
FIG. 49 is a perspective view of a collar portion of the apparatus of FIG. 41.

With reference next to FIG. 47, the catheter 432 preferably comprises a stop member 550 extending radially outwardly from the catheter surface. In the illustrated embodiment, the stop member 550 comprises an annular ring; however, it is anticipated that any sort of protuberance can be employed. With reference also to FIG. 48, a coupling member 552 preferably is movably disposed about the catheter 432 and is configured to mechanically couple to the proximal end 532 of the pusher member 500. In the illustrated embodiment, the coupling member 552 is threaded on its inner surface in order to engage the threaded proximal end 532 of the pusher member 500. When the coupling member 552 and pusher member 500 are engaged, the catheter stop member 550 is locked between the proximal end 532 of the pusher member 500 and a proximal wall 554 of the coupling member 552. As such, the catheter 432 is selectively fixed in position relative to the pusher member 500. As discussed above, the pusher member 500 is selectively fixed in position relative to the delivery tube 490. As such, when the locking cap 546 and coupling member 552 are engaged as discussed above, the catheter 432, pusher member 500 and delivery tube 490 are all in fixed positions relative to one another.

In another embodiment, the catheter 432 comprises a protuberance, such as an annular ring, and one or more locking members are provided so as to releasably secure the pusher member 500 to the catheter 432 when the coupling member 552 is engaged.

With reference next to FIG. 49, a collar 560 is illustrated. The illustrated collar 560 preferably is made of a polymer formed as a broken ring. As such, the collar 560 is resilient and circumferentially expandable.

With reference also to FIGS. 40-43, 50 and 51, the collar 560 preferably is configured to fit about the delivery tube 590. A relaxed diameter of the collar 560 is less than the diameter of at least most of the tapered portion of the delivery tube 490. Thus, the collar 560 is circumferentially expanded in order to fit over the delivery tube 490. Such circumferential expansion is resisted by the collar 560 so that the collar 560 exerts an inwardly-directed force on the delivery tube 490. In order to ease advancing of the tube through tissues, the outer diameter of the delivery tube 490 is made quite small. As a result, the width of the walls of the tube members 492, 494 preferably is quite small. In some embodiments, the thin-walled tube members are somewhat flexible. The inwardly-directed force exerted by the collar 560 helps hold the tube members 492, 494 together so as to fit closely about the catheter 432 and to contain the hemostatic material 270 within the chamber 522.

Figure 50:
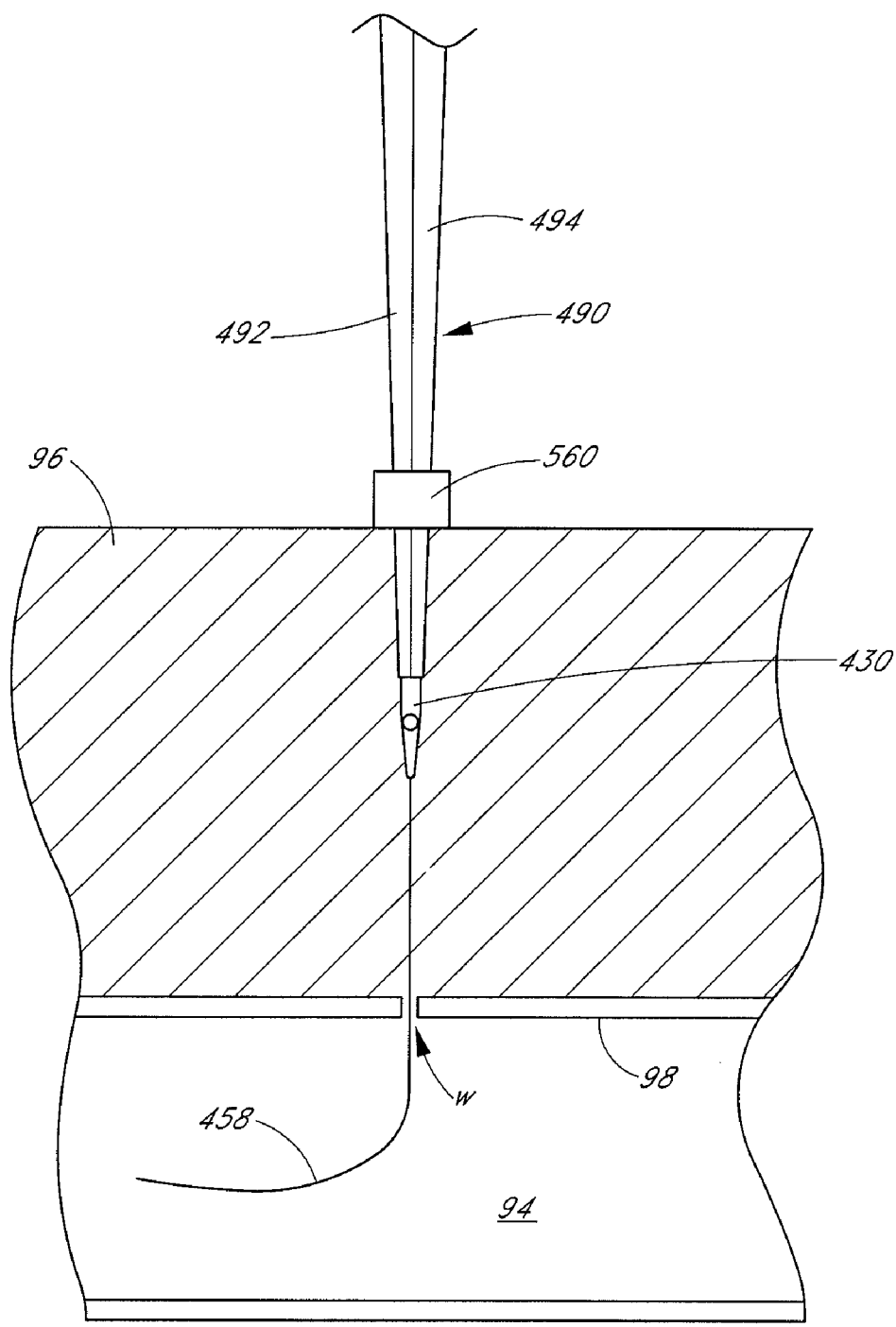
FIG. 50 shows a portion of the apparatus of FIG. 41 being advanced toward a tissue wound.
Figure 51:
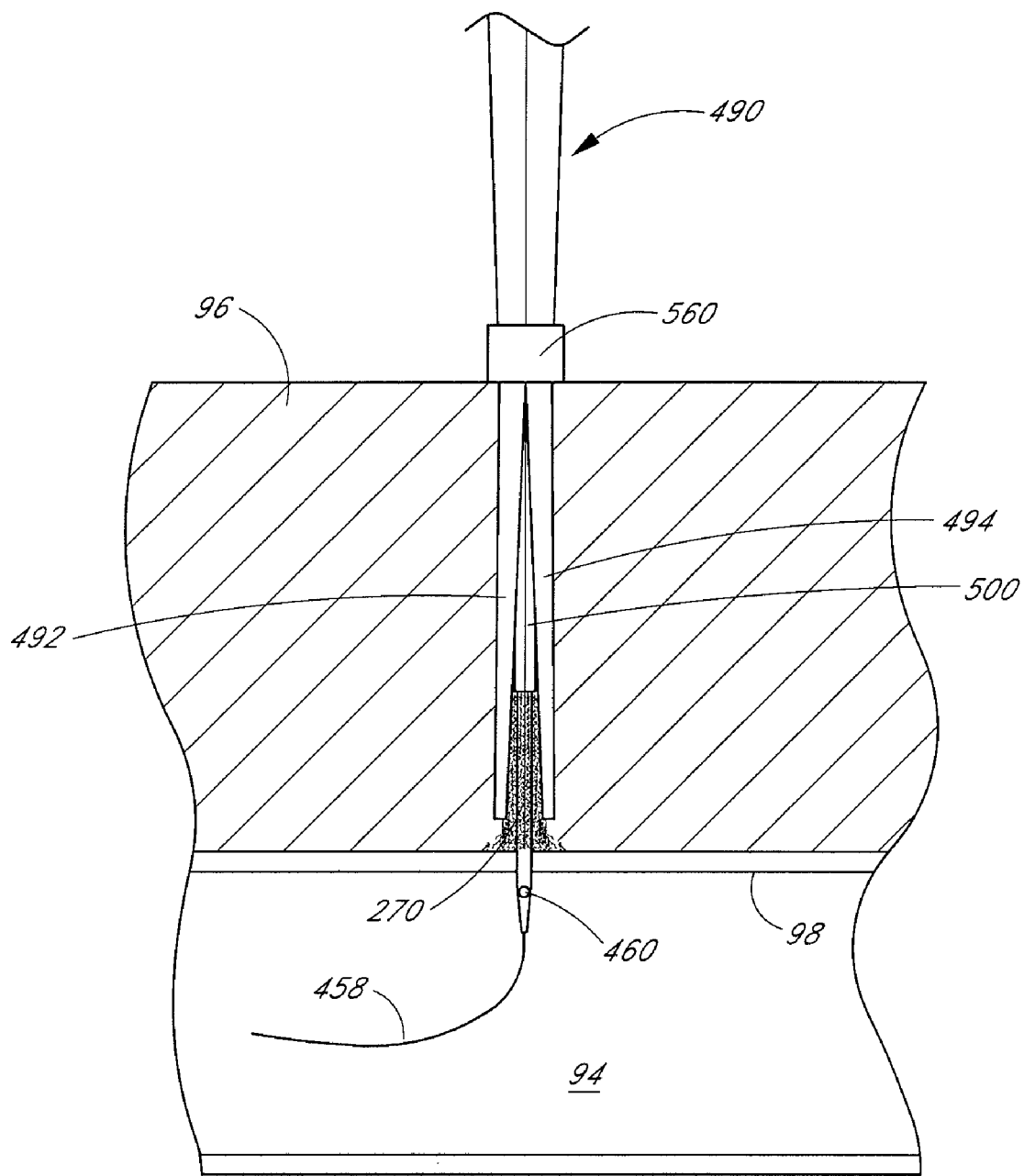
FIG. 51 shows the arrangement of FIG. 50 with the apparatus in position adjacent the wound and deploying a hemostatic agent.

In the illustrated embodiment, the collar 560 is configured to be slidable over the delivery tube 490. Preferably both the collar 560 and delivery tube 490 have smooth engaging surfaces. It is to be understood that other surface configurations can be used as appropriate. With reference next to FIGS. 43, 50 and 51, to correctly position the vessel closure device 430, the assembly is advanced over a guidewire 458 into position adjacent the wound w. FIG. 50 shows the assembly 430 partially advanced through body tissues 96 toward a puncture wound w. As the apparatus 430 is advanced, the collar 560 engages the patient's skin, as shown in FIG. 50. As the apparatus is further advanced, the collar 560 continues to engage the patient's skin and the delivery tube 490 slides distally relative to the collar 560, as shown in FIG. 43. The collar expands with the diameter of the tapered delivery tube 490 as the tube slides relative to the collar 560, and the collar continues to exert a circumferential force to help hold the tube closed. It is anticipated that the body tissue 96 surrounding the portion of the delivery tube 490 distal of the collar 560 also helps to keep the tube closed.

When the apparatus 430 is in a desired position at or adjacent a wound w, as shown in FIG. 43, the coupling member 552 and cap 546 are disengaged so that the pusher member 500 can be advanced relative to the delivery tube 490 and catheter 432. With particular reference to FIG. 51, as the pusher member 500 is advanced, the distal end 528 of the pusher member 500 engages inner surfaces 508 of the tube members 492, 494, thus forcing the tube members 492, 494 apart and deploying the hemostatic material 270 from within the delivery tube chamber 522. In the embodiment illustrated in FIG. 51, the tube members 492, 494 are flexible so that they will bend outwardly upon urging from the advancing pusher member 500.

As discussed above, in one embodiment, the hemostatic material 270 comprises a hydrophilic fibrous chitosan fleece. Since the fleece is hydrophilic, it sticks to the blood vessel 98 surrounding the wound and to surrounding body tissues 96. Further, since the fleece 270 is fibrous, and since the catheter 432 effectively plugs the wound w as the material is deployed, none of the fibrous material passes through the wound into the blood vessel 94. Further, as the catheter 432 is removed from the wound w, the fleece readily collapses into the space previously taken by the catheter. The fleece has hemostatic properties, and fully surrounds the wound w, thus aiding relatively quick hemostasis of the wound.

In some embodiments the closure device 430 is assembled so that the distance from the catheter hole 460 to the distal end 502 of the delivery tube 490 is about or slightly greater than the width of a blood vessel wall 98. As such, the delivery tube 490 is arranged immediately adjacent the wound w. With continued reference to FIGS. 43 and 51, in the illustrated embodiment, the distance from the catheter holes-460 to the distal end 502 of the delivery tube 490 is much greater than the width of a blood vessel wall 98, but less than about 1.5 cm. More preferably the distance is about 1 cm or less. As such, when the catheter holes 460 enter the blood vessel 94 and the clinician sees blood enter the viewing port 468, the delivery tube 490 is positioned close to but spaced from the vessel wall 98. In the illustrated embodiment, this is a safety feature to ensure than the distal ends 502 of the delivery tube members 492, 494 do not enter or damage the wound site w. Upon deployment of the hemostatic material 270, the pusher member 500 pushes the material over the catheter 432 and into contact with, or into close proximity to, the vessel wall 98 and the wound w. In accordance with another embodiment, the delivery tube 490 is spaced from the vessel wall 98 a distance of at least about three times the thickness of the vessel wall.

With continued reference to FIG. 51, when the tube members 492, 494 are expanded upon deployment as illustrated, there is further resistance to distal movement of the tube members 492, 494, thus further contributing to safety. Still further, although the collar 560 is slidable over the delivery tube 490, it contributes some frictional resistance so further distal movement of the delivery tube 490 relative to the collar 560.

The most common sizes of catheters used for interventions through the femoral artery are sized about 6 F or less. In the embodiment illustrated in FIGS. 40-51, the catheter 432 preferably is about 6.5 F in size. Since the catheter 432 of the closure device is of greater diameter than the catheters used by the clinician prior to closure of the wound, the catheter 432 is large enough to tightly engage the wound edges and effectively plug the wound. This tight fit of the catheter 432 relative to the wound w helps prevent hemostatic material 270 from passing between the catheter and the wound edges and into the blood vessel 94. It is to be understood that different sizes of catheters may be used for interventions, and for the closure apparatus. Preferably the closure apparatus catheter 432 has a greater diameter than catheter(s) and other surgical implements used in the procedure prior to closure. Preferably, the catheter 432 has a diameter about 0-1 F, and more preferably about 0.5 F, greater than earlier-used catheters.

In accordance with still another embodiment, the delivery tube 490 comprises indicia printed or otherwise marked thereon. In use, the clinician notes, during initial vascular puncture, the depth of the puncture. Later, during vessel closure, the indicia on the delivery tube 490 serves as a reference for the clinician to verify the depth of the tube and its position relative to the vascular wound. It is to be understood that such indicia may be printed on the delivery tube or may be physically formed as raised or lowered portions of the tube.

In accordance with another embodiment, a vascular wound closure apparatus having features as discussed above in connection with FIG. 12-23, 25-28, 29-37, or 40-51 is provided in a kit for use by a clinician. In this embodiment, the apparatus is formed of a disposable, yet suitable material, such as a medical grade plastic, and is assembled and loaded so that the members are releasably coupled to one another and hemostatic material is disposed in the delivery tube. Although the apparatus may be provided pre-assembled, a clinician may still adjust the position of the tube relative to the catheter by decoupling the tube and pusher member, making the adjustment, and then recoupling the tube and pusher member. The apparatus is sterilized and preferably is disposed within a closed, sterilized container (not shown) which is configured to be opened in a sterile environment such as an operating room or catheter lab.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An apparatus for subcutaneously delivering a material, comprising:
    an elongate delivery tube having a chamber enclosing a malleable fibrous hemostatic material therewithin;
    an elongate catheter extending longitudinally through the delivery tube, the chamber being defined between the catheter and the delivery tube;
    an elongate pusher member having a distal portion configured to slidably extend through at least a portion of the delivery tube chamber so as to push at least a portion of the material out of the delivery tube, the pusher member having a surface with at least one protuberance disposed proximal a distal end of the pusher member and distal a proximal end of the pusher member so that the surface extends both proximally and distally of the protuberance, the pusher member protuberance having a protuberance length along the elongate pusher member;
    a flexible locking member configured to fit at least partially around the pusher member and adapted to expand in a transverse direction when subjected to generally longitudinal compression, the flexible locking member having a longitudinal length that is greater than the protuberance length;
    wherein the flexible locking member is disposed adjacent the pusher member protuberance so that when the locking member is subjected to generally longitudinal compression, the locking member expands transversely to engage the pusher member protuberance and the pusher member surface adjacent the protuberance to increase friction between the pusher member and the locking member so that the pusher member is restrained from moving relative to the locking member.

2. The apparatus of claim 1, wherein the flexible locking member is configured to engage a proximal end of the delivery tube.

3. The apparatus of claim 2 additionally comprising a locking cap configured to selectively compress the flexible locking member between the cap and the proximal end of the delivery tube.

4. The apparatus of claim 3, wherein the locking cap is selectively engageable with the delivery tube.

5. The apparatus of claim 1, wherein the locking member is substantially ring-shaped.

6. The apparatus of claim 1, wherein the protuberance comprises an annular ring projecting from a surface of the pusher member.

7. The apparatus of claim 1, wherein the protuberance comprises at least one bump projecting from a surface of the pusher member.

8. The apparatus of claim 1, wherein a surface of the pusher member comprises a pit formed therein, and the protuberance projects from the pit.

9. The apparatus of claim 1, wherein the protuberance extends outwardly between about 0.05-0.3 mm.

10. The apparatus of claim 1, wherein the protuberance extends outwardly between about 0.1-0.2 mm.

11. The apparatus of claim 1, wherein the material is hydrophilic.

12. The apparatus of claim 11, wherein the material comprises a chitosan fleece.

13. The apparatus of claim 12, wherein the material comprises a chitosan fleece and a starch.

14. The apparatus of claim 11, wherein the material comprises chitosan.

15. The apparatus of claim 1, wherein the delivery tube comprises a plurality of elongate tube members configured to move radially relative to one another between an engaged closed position and an open position.

16. The apparatus of claim 15, wherein the tube members are flexible, and additionally comprising an elastically expandable collar disposed about the tube members, the collar being biased to hold the tube members in the closed position.

17. The apparatus of claim 16, wherein the collar is slidable over the delivery tube.

18. The apparatus of claim 1, wherein the catheter comprises a hole formed through a side wall of the catheter, and the delivery tube is arranged on the catheter so that a distal end of the tube is proximal the side hole.

19. The apparatus of claim 18, wherein the distal end of the delivery tube is between about 5-1.5 mm from the catheter side hole.

20. The apparatus of claim 18, wherein the distal end of the delivery tube is arranged a distance from the side hole at least three times the thickness of the blood vessel wall.

21. An apparatus for subcutaneously delivering a material, comprising:
an elongate delivery tube having a chamber enclosing a malleable fibrous hemostatic material therewithin, a distal portion of the delivery tube having a smaller diameter than a proximal portion of the delivery tube;
an elongate catheter extending through the delivery tube, the chamber being defined as space between the catheter and the delivery tube, the distal portion of the delivery tube engaging the catheter;
an elongate pusher member having a surface with at least one protuberance, and additionally comprising a distal portion configured to slidably extend through at least a portion of the delivery tube so as to push at least a portion of the material out of the delivery tube, a portion of the pusher member having a diameter less than the proximal portion of the delivery tube but greater than the distal portion of the delivery tube so that when the pusher is moved distally relative to the delivery tube, the pusher member portion engages an inner surface of the distal portion of the delivery tube and deforms the delivery tube, the pusher member portion being disposed within the delivery tube chamber proximal of the hemostatic material so that the hemostatic material is enclosed between the pusher member portion, delivery tube and catheter;
a flexible locking member configured to fit at least partially around the pusher member portion and adapted to expand in a transverse direction when subjected to generally longitudinal compression;
wherein the flexible locking member is disposed adjacent the protuberance on the pusher member portion so that when the locking member is subjected to generally longitudinal compression, the locking member expands transversely to engage the pusher member protuberance and the pusher member surface adjacent the protuberance so as to increase friction between the pusher member and the locking member so that the pusher member is restrained from moving relative to the locking member, and wherein the locking member simultaneously engages the pusher member and the delivery tube.

22. The apparatus of claim 21, wherein the delivery tube comprises a plurality of elongate segments having side edges, the elongate segments being coupled together along their side edges to define the delivery tube.

23. The apparatus of claim 22, wherein the inner surface of the delivery tube tapers toward a distal end of the delivery tube.

24. The apparatus of claim 23, wherein when the pusher member is advanced distally relative to the tube, a distal end of the pusher member engages the tapered delivery tube inner surface so as to at least partially open the tube.

25. The apparatus of claim 22 additionally comprising an elastically expandable collar disposed about the delivery tube segments distal of the proximal end of the delivery tube and distal of the position of the pusher member portion that is within the delivery tube, wherein the collar is biased to hold the tube segments coupled together.

26. The apparatus of claim 25, wherein the collar is slidable over the delivery tube.

27. The apparatus of claim 22, wherein a distal portion of the pusher member is configured to contact a segment of the delivery tube at a location between about ⅔ and ¾ of the distance from the proximal end to the distal end of the segment.

28. The apparatus of claim 21, wherein the flexible locking member is configured to engage a proximal end of the delivery tube.

29. The apparatus of claim 28 additionally comprising a locking cap configured to selectively compress the flexible locking member between the cap and the proximal end of the delivery tube.

30. The apparatus of claim 29, wherein the locking cap is selectively engageable with the delivery tube.

31. An apparatus for subcutaneously delivering a material, comprising:
an elongate delivery tube having a chamber enclosing a malleable fibrous hemostatic material therewithin;
an elongate catheter extending longitudinally through the delivery tube, the chamber being defined between the catheter and the deliver, tube;
an elongate pusher member having a distal portion configured to slidably extend through at least a portion of the delivery tube chamber so as to push at least a portion of the material out of the delivery tube, the pusher member having a surface with at least one protuberance disposed proximal a distal end of the pusher member and distal a proximal end of the pusher member so that the surface extends both proximally and distally of the protuberance;

a flexible locking member configured to fit at least partially around the pusher member and adapted to expand in a transverse direction when subjected to generally longitudinal compressions;

wherein the flexible locking member is disposed adjacent the pusher member protuberance so that when the locking member is subjected to generally longitudinal compression, the locking member expands transversely to simultaneously engage the pusher member protuberance and the pusher member surface adjacent the protuberance to increase friction between the pusher member and the locking member so that the gusher member is restrained from moving relative to the locking member.

32. The apparatus of claim 31, wherein the pusher member protuberance has a length along the elongate pusher member, and the flexible locking member has a longitudinal length, and the locking member longitudinal length is greater than the protuberance length.

33. The apparatus of claim 31, wherein the protuberance comprises an annular ring projecting from a surface of the pusher member.

34. The apparatus of claim 31, wherein the protuberance comprises at least one bump projecting from a surface of the pusher member.

35. The apparatus of claim 31, wherein the material comprises chitosan.

36. The apparatus of claim 31, wherein the delivery tube comprises a plurality of elongate tube members configured to move radially relative to one another between an engaged closed position and an open position.

37. The apparatus of claim 36, wherein the tube members are flexible, and additionally comprising an elastically expandable collar disposed about the tube members, the collar being biased to hold the tube members in the closed position.

38. The apparatus of claim 37, wherein the collar is slidable over the delivery tube.

\* \* \* \* \*

UNITED STATES PATENT AND TRADEMARK OFFICE
CERTIFICATE OF CORRECTION

PATENT NO.       : 8,012,167 B2
APPLICATION NO.  : 10/919939
DATED            : September 6, 2011
INVENTOR(S)      : Zhu et al.

Page 1 of 1

It is certified that error appears in the above-identified patent and that said Letters Patent is hereby corrected as shown below:

In column 6, line 25, delete "in it" and insert --in its-- therefore.

In column 15, line 52, delete "310," and insert --310-- therefore.

In column 16, line 15, delete "354" and insert --354.-- therefore.

In column 20, line 24, delete ""'"." and insert --"'"-- therefore.

In column 21, line 60, delete "350f'," and insert --350f'',-- therefore.

In column 22, line 6, delete "350f'," and insert --350f'',-- therefore.

In column 22, line 9, delete "350f'," and insert --350f'',-- therefore.

In column 22, line 50, delete "310'" and insert --310''-- therefore.

In column 23, line 11, delete "337'" and insert --337''-- therefore.

In column 23, line 22, delete "350f'," and insert --350f'',-- therefore.

In column 23, line 22, delete "350g'" and insert --350g''-- therefore.

In column 23, line 46, delete "350f'," and insert --350f'',-- therefore.

In column 29, line 3, delete "holes-460" and insert --holes 460-- therefore.

In column 29, line 57, delete "FIG." and insert --FIGS.-- therefore.

In column 32, line 58, delete "deliver" and insert --delivery-- therefore.

In column 33, line 12, delete "gusher" and insert --pusher-- therefore.

Signed and Sealed this
Third Day of April, 2012

David J. Kappos
*Director of the United States Patent and Trademark Office*